United States Patent
Edinger et al.

(10) Patent No.: US 10,077,236 B2
(45) Date of Patent: Sep. 18, 2018

(54) AZACYCLIC CONSTRAINED ANALOGS OF FTY720

(71) Applicants: The Regents of the University of California, Oakland, CA (US); The Universite de Montreal, Montreal, QC (CA)

(72) Inventors: Aimee Edinger, Irvine, CA (US); Stephen Hanessian, Irvine, CA (US)

(73) Assignees: The Regents of the University of California, Oakland, CA (US); The Université de Montréal, Montreal, Québec (CA)

( * ) Notice: Subject to any disclaimer, the term of this patent is extended or adjusted under 35 U.S.C. 154(b) by 0 days.

(21) Appl. No.: 14/903,579

(22) PCT Filed: Jul. 15, 2014

(86) PCT No.: PCT/US2014/046711
§ 371 (c)(1),
(2) Date: Jan. 7, 2016

(87) PCT Pub. No.: WO2015/009731
PCT Pub. Date: Jan. 22, 2015

(65) Prior Publication Data
US 2016/0159739 A1    Jun. 9, 2016

Related U.S. Application Data

(60) Provisional application No. 61/846,506, filed on Jul. 15, 2013.

(51) Int. Cl.
*C07D 207/12* (2006.01)
*C07F 9/572* (2006.01)

(52) U.S. Cl.
CPC ............ *C07D 207/12* (2013.01); *C07F 9/572* (2013.01); *C07F 9/5722* (2013.01)

(58) Field of Classification Search
CPC .............................. C07D 207/00; C07F 9/572
USPC ........................................................ 548/400
See application file for complete search history.

(56) References Cited

U.S. PATENT DOCUMENTS

| | | | |
|---|---|---|---|
| 3,687,808 A | 8/1972 | Clercq et al. | |
| 4,845,205 A | 7/1989 | Huynh et al. | |
| 5,034,506 A | 7/1991 | Summerton et al. | |
| 5,130,302 A | 7/1992 | Spielvogel et al. | |
| 5,134,066 A | 7/1992 | Rogers et al. | |
| 5,166,315 A | 11/1992 | Summerton et al. | |
| 5,175,273 A | 12/1992 | Bischofberger et al. | |
| 5,185,444 A | 2/1993 | Summerton et al. | |
| 5,367,066 A | 11/1994 | Urdea et al. | |
| 5,432,272 A | 7/1995 | Benner et al. | |
| 5,434,257 A | 7/1995 | Matteucci et al. | |
| 5,457,187 A | 10/1995 | Gmeiner et al. | |
| 5,457,191 A | 10/1995 | Andrews et al. | |
| 5,459,255 A | 10/1995 | Manoharan et al. | |
| 5,484,908 A | 1/1996 | Froehler et al. | |
| 5,502,177 A | 3/1996 | Matteucci et al. | |
| 5,525,711 A | 6/1996 | Hawkins et al. | |
| 5,552,540 A | 9/1996 | Haralambidis | |
| 5,587,469 A | 12/1996 | Manoharan et al. | |
| 5,594,121 A | 1/1997 | Froehler et al. | |
| 5,596,091 A | 1/1997 | Switzer | |
| 5,614,617 A | 3/1997 | Sanghvi et al. | |
| 5,645,985 A | 7/1997 | Froehler et al. | |
| 5,681,941 A | 10/1997 | Cook et al. | |
| 5,698,685 A | 12/1997 | Summerton et al. | |
| 5,750,692 A | 5/1998 | Cook et al. | |
| 5,763,588 A | 6/1998 | Matteucci et al. | |
| 5,808,027 A | 9/1998 | Manoharan et al. | |
| 5,811,534 A | 9/1998 | Cook et al. | |
| 5,830,653 A | 11/1998 | Froehler et al. | |
| 5,859,221 A | 1/1999 | Kawasaki et al. | |
| 5,948,903 A | 9/1999 | Cook et al. | |
| 6,005,087 A | 12/1999 | Cook et al. | |
| 6,005,096 A | 12/1999 | Matteucci et al. | |
| 6,166,199 A | 12/2000 | Manoharan et al. | |
| 6,268,490 B1 | 7/2001 | Imanishi et al. | |
| 6,525,191 B1 | 2/2003 | Ramasamy et al. | |
| 6,531,584 B1 | 3/2003 | Cook et al. | |

(Continued)

FOREIGN PATENT DOCUMENTS

| | | |
|---|---|---|
| CA | 2627502 A1 | 5/2007 |
| EP | 2058301 A1 | 5/2009 |

(Continued)

OTHER PUBLICATIONS

International Preliminary Report on Patentability for International Application PCT/US2014/046711, dated Jan 19, 2016, dated Jan 28, 2016, 7 Pgs.
International Search Report and Written Opinion for International Application PCT/US2014/046711, completed Nov 26, 2014, dated Dec 30, 2014, 10 Pgs.
Azuma et al., "Induction of Apoptosis in Human Bladder Cancer Cells In Vitro and In Vivo Caused by FTY720 Treatment", The Journal of Urology, Jun. 2003, vol. 169, pp. 2372-2377.
Azuma et al, "Marked Prevention of Tumor Growth and Metastasis by a Novel Immunosuppressive Agent, FTY720, in Mouse Breast Cancer Models", Cancer Research, Mar. 1, 2002, vol. 62, pp. 1410-1419.

(Continued)

*Primary Examiner* — Yong Chu
(74) *Attorney, Agent, or Firm* — KPPB LLP

(57) ABSTRACT

Small molecules comprised of azacyclic constrained analogs of FTY720 are provided. Formulations and medicaments are also provided that are directed to the treatment of disease, such as, for example, leukemia, and other diseases. Therapeutics are also provided containing a therapeutically effective dose of one or more small molecule compounds, present either as pharmaceutically effective salt or in pure form, including, but not limited to, formulations for oral, intravenous, or intramuscular administration.

10 Claims, 41 Drawing Sheets

(56) References Cited

U.S. PATENT DOCUMENTS

| | | | |
|---|---|---|---|
| 6,670,461 B1 | 12/2003 | Wengel et al. | |
| 6,770,748 B2 | 8/2004 | Imanishi et al. | |
| 6,794,499 B2 | 9/2004 | Wengel et al. | |
| 7,034,133 B2 | 4/2006 | Wengel et al. | |
| 7,053,207 B2 | 5/2006 | Wengel | |
| 7,399,845 B2 | 7/2008 | Swayze et al. | |
| 7,427,672 B2 | 9/2008 | Imanishi et al. | |
| 7,547,684 B2 | 6/2009 | Seth et al. | |
| 7,569,686 B1 | 8/2009 | Bhat et al. | |
| 7,572,582 B2 | 8/2009 | Wengel et al. | |
| 7,638,637 B2 * | 12/2009 | Lynch | C07F 9/65062 548/205 |
| 7,666,854 B2 | 2/2010 | Seth et al. | |
| 7,696,345 B2 | 4/2010 | Allerson et al. | |
| 7,741,457 B2 | 6/2010 | Swayze et al. | |
| 7,750,131 B2 | 7/2010 | Seth et al. | |
| 7,772,406 B2 | 8/2010 | Morimoto et al. | |
| 7,875,733 B2 | 1/2011 | Bhat et al. | |
| 7,939,677 B2 | 5/2011 | Bhat et al. | |
| 7,968,733 B2 | 6/2011 | Suzuki et al. | |
| 8,022,193 B2 | 9/2011 | Swayze et al. | |
| 8,030,467 B2 | 10/2011 | Seth et al. | |
| 8,080,644 B2 | 12/2011 | Wengel et al. | |
| 8,088,746 B2 | 1/2012 | Seth et al. | |
| 8,088,904 B2 | 1/2012 | Prakash et al. | |
| 8,124,745 B2 | 2/2012 | Allerson et al. | |
| 8,153,365 B2 | 4/2012 | Wengel et al. | |
| 8,268,980 B2 | 9/2012 | Seth et al. | |
| 8,278,283 B2 | 10/2012 | Seth et al. | |
| 8,278,425 B2 | 10/2012 | Prakash et al. | |
| 8,278,426 B2 | 10/2012 | Seth et al. | |
| 8,309,768 B2 | 11/2012 | Chen et al. | |
| 8,440,803 B2 | 5/2013 | Prakash et al. | |
| 8,501,805 B2 | 8/2013 | Seth et al. | |
| 8,530,640 B2 | 9/2013 | Seth et al. | |
| 8,546,556 B2 | 10/2013 | Seth et al. | |
| RE44,779 E | 2/2014 | Obika et al. | |
| 8,796,437 B2 | 8/2014 | Prakash et al. | |
| 9,005,906 B2 | 4/2015 | Prakash et al. | |
| 9,012,421 B2 | 4/2015 | Migawa et al. | |
| 9,115,054 B2 | 8/2015 | Dhar et al. | |
| 2003/0158403 A1 | 8/2003 | Manoharan et al. | |
| 2003/0175906 A1 | 9/2003 | Manoharan et al. | |
| 2005/0256056 A1 | 11/2005 | North et al. | |
| 2006/0019900 A1 | 1/2006 | Lam et al. | |
| 2008/0039618 A1 | 2/2008 | Allerson et al. | |
| 2010/0022655 A1 | 1/2010 | Byrd et al. | |
| 2010/0120858 A1 * | 5/2010 | Caprathe | C07D 211/22 514/318 |
| 2013/0123366 A1 | 5/2013 | Byrd et al. | |
| 2013/0203836 A1 | 8/2013 | Rajeev et al. | |
| 2015/0191727 A1 | 7/2015 | Migawa et al. | |

FOREIGN PATENT DOCUMENTS

| | | |
|---|---|---|
| EP | 3022176 A2 | 5/2016 |
| FR | 2968556 A1 | 6/2012 |
| JP | 2016529236 A | 9/2016 |
| WO | 1999014226 A2 | 3/1999 |
| WO | 2004106356 A1 | 12/2004 |
| WO | 2007134181 A2 | 11/2007 |
| WO | 2008016674 A1 | 2/2008 |
| WO | 2008079382 A1 | 7/2008 |
| WO | 2008097819 A2 | 8/2008 |
| WO | 2009053481 A1 | 4/2009 |
| WO | 2009106599 A2 | 9/2009 |
| WO | 2011133876 A2 | 10/2011 |
| WO | 2012080641 A1 | 6/2012 |
| WO | 2014179620 A1 | 11/2014 |
| WO | 2015009731 A2 | 1/2015 |
| WO | 2015009731 A3 | 3/2015 |
| WO | 2015106128 A2 | 7/2015 |
| WO | 2017053990 A1 | 3/2017 |

OTHER PUBLICATIONS

Brinkmann, "FTY720 (fingolimod) in Multiple Sclerosis: therapeutic effects in the immune and the central nervous system", British Journal of Pharmacology, 2009, vol. 158, pp. 1173-1182.

Chua et al, "FTY720, a fungus metabolite, inhibits in vivo growth of androgen-independent prostate cancer", Int. J. Cancer, 2005, vol. 117, pp. 1039-1048.

Clemens et al, "Synthesis of 4(5)-phenylimidazole-based analogues of sphingosine-1-phosphate and FTY720: Discovery of potent S1P1 receptors agonists", Bioorganic & Medicinal Chemistry Letters, 2005, vol. 15, pp. 3568-3572.

Davis et al, "Sphingosine 1-Phosphate Analogs as Receipt Antagonists", The Journal of Biological Chemistry, 2005, vol. 280, No. 11, pp. 9833-9841.

Deng et al, "Protein phosphatase 2A inactivates Bc12's antiapoptotic function by dephosphorylation and up-regulation of Bc12-p53 binding", Blood, Jan. 8, 2009, vol. 113, No. 2, pp. 422-428.

Forrest et al, "Immune Cell Regulation and Cardiovascular Effects of sphingosine 1-Phosphate Receptor Agonists in Rodents Are Mediated via Distinct Receptor Subtypes", The Journal of Pharmacology and Experimental Therapeutics, Jan. 26, 2004, vol. 309, No. 2, pp. 758-768.

Fransson et al., "Design, Synthesis, and Antileukemic Activity of Stereochemically Defined Constrained Analogues of FTY720 (Gilenya)", ACS Med. Chern. Lett., 4(10): 969-973, 2013. 17-21,23,24,28-31 [retrieved on Nov. 26, 2014]. Retrieved from the Internet.<URL:http://pubs.acs.org/doi/abs/10.1 021/ml4002425>.

Gauchot et al, "Asymmetric Aldol Reaction Catalyzed by the Anion of an Ionic Liquid", Journal of Organic Chemistry, 2012, vol. 77, pp. 4917-4923.

Hanessian et al, "Constrained Azacyclic analogues of the immunomodulatory agent FTY720 as molecular probes for sphingosine 1-phosphate receptors", Bioorganic & Medicinal Chemistry Letters, 2007, vol. 17, pp. 491-494.

Kim et al, "Synthesis of (3R)-Carboxy Pyrrolidine (a β-Proline Analogue) and its Oligomer", Bioorganic & Medicinal Chemistry Letters, 2000, vol. 10, pp. 2417-2419.

Kiuchi et al, "Synthesis and Immunosuppressive Activity of 2-Substituted 2-Aminopropane-1,3-diols and 2-Aminoethanols[1,2]", J. Med. Chem. 2000, vol. 43, pp. 2946-2961.

Koyrakh et al, "The Heart Rate Decrease Caused by Acute RTY720 Administration is Mediated by the G Protein-Gated Potassium Channel $I_{KACh}$", American Journal of Transplantation, 2005, vol. 5, pp. 529-536.

Kucznierz et al, "Tetrahydro-isoquioline-Based Factor Xa Inhibitors", J. Med. Chem., 1998, vol. 41, pp. 4983-4994.

Lee et al, "FTY720: A Promising Agent for Treatment of Metastatic Hepatocellular Carcinoma", Clin. Cancer Res., Dec. 1, 2005, vol. 11, No. 23, pp. 8458-8466.

Lim et al, "(r)-FTY720 methyl ether is a specific sphingosine kinase 2 inhibitor: Effect on sphingosine kinase 2 expression in HEK293 cells and actin rearrangement and survival of MCF-7 breast cancer cells", Cellular Signalling, 2011, vol. 23, pp. 1590-1595.

Mitsumori et al, "Direct Asymmetric anti-Mannich-Type Reactions Catalyzed by a Designed Amino Acid", J. Am. Chem. Soc., 2006, vol. 128, pp. 1040-1041.

Neviani et al, "FTY720, a new alternative for treating blast crisis chromic myelogenous leukemia and Philadelphia chromosome-positive acute lymphocytic leukemia", The Journal of Clinical Investigation, Sep. 2007, vol. 117, No. 9, pp. 2408-2421.

Reed, "Bcl-2-family proteins and hematologic malignancies: history and future prospects", Blood, Apr. 1, 2008, vol. 111, No. 7, pp. 3322-3330.

Rosen et al, "Design, Synthesis, and Properties of (4S)-7-(4-Amino-2-substituted-pyrrolidin-1-yl)quinolone-3-carboxulic Acids", J. Med. Chem., 1988, vol. 31, pp. 1598-1611.

Sanna et al, "Sphingosine 1-Phosphate (S1P) Receptor Subtypes $S1P_1$ and $S1P_3$, Respectively, Regulate Lymphocyte Recirculation and Heart Rate", The Journal of Biological Chemistry, Apr. 2, 2004, vol. 279, No. 14, pp. 13839-13848.

Sun et al, "A Photoreactive Analogue of the Immunosuppressant FTY720", J. Org. Chem., 2006, vol. 71, pp. 2200-2202.

(56) References Cited

OTHER PUBLICATIONS

Tigyi et al, "FTY720 S-ene-phosphonate is a novel pan-antagonist of the S1P receptors that inhibits lymphocyte egress", FASEB Journal, Apr. 2010, vol. 24, No. 1, Supplement, 2 pgs. (Abstract).
Toumi et al, "Total Synthesis of Paliurine F", Angew. Chem. Int. Ed., 2007, vol. 46, pp. 572-575.
Valentine et al, "(S)-FTY720-Vinylphosphonate, an Analogue of the Immunosuppressive Agent FTY720, Is a Pan-antagonist of Sphingosine 1-Phosphate GPCR Signaling and Inhibits Autotaxin Activity", Cell Signal, Oct. 2010, vol. 22, No. 10, pp. 1543-1553.
Watanabe et al, "Design and Stereoselective Synthesis of Four Peptide Nucleic Acid Monomers with Cyclic Structures in Backbone", Journal of Heterocyclic Chemistry, 2011, vol. 48, pp. 1132-1139.
Watts et al, "Structure-Reactivity Studies of Simple 4-Hydroxyprolinamide Organocatalysts in the Asymmetric Michael Addition Reaction of Aldehydes to Nitroolefins", Adv. Synth. Catal., 2012, vol. 354, pp. 1035-1042.
Zhang et al, "Rationally designed 4-phenoxy substituted prolinamide phenols organocatalyst for the direct aldol reaction in water", Tetrahedron Letters, 2009, vol. 50, pp. 1173-1176.
Zhu et al, "Asymmetric Synthesis of Conformationally Constrained Fingolimod Analogues—Discovery of an Orally Active Sphingosine 1-Phosphate Receptor Type-1 Agonist and Receptor Type-3 Antagonist", J. Med. Chem., 2007, vol. 50, pp. 6428-6435.
Extended European Search Report for European Application No. 14825876.7, Search completed Feb. 22, 2017, dated Mar. 2, 2017, 9 Pgs.
Lamontagne, K. et al., Antagonism of Sphingosine-1-Phosphate Receptors by FTY720 Inhibits Angiogenesis and Tumor Vascularization, Cancer Res., Jan. 1, 2006, vol. 66, p. 221-231.
Rosales, K. R. et al., Sphingolipid-based drugs selectively kill cancer cells by down-regulating nutrient transporter proteins, Biochem. J., Jul. 18, 2011, vol. 439, p. 299-311.
International Search Report and Written Opinion for International Application No. PCT/US2016/053815, completed Nov. 11, 2016, dated Dec. 27, 2016, 8 Pgs.
Azuma, Haruhito et al., "Induction of Apoptosis in Human Bladder Cancer Cells in Vitro and in Vivo Caused by FTY720 Treatment", The Journal of Urology, vol. 169, Jun. 2003, pp. 2372-2377.
Barraclough et al., "Synthesis of kainoid analogues", Tetrahedron, vol. 51, Issue 14, Apr. 3, 1995, pp. 4195-4212, https://doi.org/10.1016/0040-4020(95)00135-U.
Bauer, D. E. et al., "Cytokine stimulation of aerobic glycolysis in hematopoietic cells exceeds proliferative demand", FASEB Journal, vol. 18, No. 11, Aug. 2004, pp. 1303-1305, published online Jun. 4, 2004, https://doi.org/10.1096/fj.03-1001fje.
Bird, Damian K. et al., "Metabolic Mapping of MCF10A Human Breast Cells via Multiphoton Fluorescence Lifetime Imaging of the Coenzyme NADH", Cancer Research, Oct. 2005, vol. 65, Issue 19, pp. 8766-8773, DOI: 10.1158/0008-5472.CAN-04-3922.
Birsoy, Kivanc et al., "Metabolic determinants of cancer cell sensitivity to glucose limitation and biguanides", Nature, vol. 508, Apr. 3, 2014, pp. 108-112, doi:10.1038/nature13110, first published Mar. 16, 2014.
Braasch et al., "Novel Antisense and Peptide Nucleic Acid Strategies for Controlling Gene Expression", Biochemistry, 2002, vol. 41, No. 14, pp. 4503-4510, DOI: 10.1021/bi0122112, Online Publication Date Mar. 9, 2002.
Camm, J. et al., "Cardiac and vascular effects of fingolimod: Mechanistic basis and clinical implications", American Heart Journal, Jul. 11, 2014, vol. 168, No. 5, pp. 632-644, DOI: 10.1016/j.ahj.2014.06.028.
Chabaud et al., "Stereoselective synthesis of (3S,4S)-tert-butyl-N-Boc-3-ethyl-4-hydroxy-l-prolinate and (3S,4R)-tert-butyl-N-Boc-3-ethyl-4-hydroxy-l-prolinate", Tetrahedron, vol. 61, Issue 15, Apr. 11, 2005, pp. 3725-3731, https://doi.org/10.1016/j.tet.2005.02.006.
Chalfant et al., "The structural requirements for ceramide activation of serine-threonine protein phosphatases", The Journal of Lipid Research, vol. 45, Mar. 2004, pp. 496-506, doi: 10.1194/jlr.M300347-JLR200, First Published on Dec. 1, 2003.
Chen et al., "Azacyclic FTY720 Analogues That Limit Nutrient Transporter Expression but Lack S1P Receptor Activity and Negative Chronotropic Effects Offer a Novel and Effective Strategy to Kill Cancer Cells in Vivo", ACS Chemical Biology, Feb. 19, 2016, vol. 11, No. 2, pp. 409-414, Published online Dec. 14, 2015. doi: 10.1021/acschembio.5b00761.
Chen et al., "Crucial role of p53-dependent cellular senescence in suppression of Pten-deficient tumorigenesis", Nature, Aug. 4, 2005, vol. 436, No. 7051, pp. 725-730, doi:10.1038/nature03918.
Chung, N. et al., "Phytosphingosine as a Specific Inhibitor of Growth and Nutrient Import in Saccharomyces cerevisiae", The Journal of Biological Chemistry, Sep. 21, 2001, vol. 276, pp. 35614-35621, First Published on Jul. 23, 2001, doi: 10.1074/jbc.M105653200.
Clemens, Jeremy, "Synthesis of 4(5)-phenylimidazole-based analogues of sphingosine-1-phosphate and FTY720: Discovery of potent S1P1 receptor agonists", Bioorganic & Medicinal Chemistry Letters, vol. 15, 2005, pp. 3568-3572.
Cohen, J. A., "Mechanisms of fingolimod's efficacy and adverse effects in multiple sclerosis", Ann. Neurol., vol. 69, Issue 5, May 2011, pp. 759-777, https://doi.org/10.1002/ana.22426.
Commisso, C. et al., "Macropinocytosis of protein is an amino acid supply route in Ras-transformed cells", Nature, vol. 497, May 30, 2013, pp. 633-637, doi:10.1038/nature12138.
Digman, M. A. et al., "The Phasor Approach to Fluorescence Lifetime Imaging Analysis", Biophysical Journal, vol. 94, Issue 2, Jan. 15, 2008, pp. L14-L16, https://doi.org/10.1529/biophysj.107.120154.
Dong, X. et al., "PI(3,5)P2 controls membrane trafficking by direct activation of mucolipin Ca2 in the endolysosome", Nature Communications, vol. 1, Article 38, 2010, 11 pages, first published Jul. 13, 2010, doi:10.1038/ncomms1037.
Dorn et al., "Synthesis, Characterization, and Properties of the Polyphosphinoboranes [RPH-BH2]n (R=Ph, iBu, p-nBuC6H4, p-dodecylC6H4): Inorganic Polymers with a Phosphorus-Boron Backbone", Macromolecules, 2003, vol. 36, No. 2, pp. 291-297, DOI: 10.1021/ma021447q, Online Publication Date Dec. 19, 2002.
Feun, L. G. et al., "Arginine deprivation in cancer therapy", Current Opinion in Clinical Nutrition & Metabolic Care, Jan. 2015, vol. 18, Issue 1, pp. 78-82, doi: 10.1097/MCO.0000000000000122.
Fransson, Rebecca et al., "Design, Synthesis, and Antileukemic Activity of Stereochemically Defined Constrained Analogues of FTY720 (Gilenya)", ACS Medical Chemistry Letters, vol. 4, No. 10, 2013, pp. 969-973, DOI: 10.1021/ml4002425, first published Aug. 21, 2013.
Freier et al., "The ups and downs of nucleic acid duplex stability: Structure-stability studies on chemically-modified DNA:RNA duplexes", Nucleic Acids Research, vol. 25, Issue 22, Nov. 1, 1997, pp. 4429-4443, https://doi.org/10.1093/nar/25.22.4429.
Frieden et al., "Expanding the design horizon of antisense oligonucleotides with alpha-L-LNA", Nucleic Acids Research, vol. 31, Issue 21, Nov. 1, 2003, pp. 6365-6372, https://doi.org/10.1093/nar/gkg820.
Guenther, G. G. et al., "Ceramide starves cells to death by downregulating nutrient transporter proteins", PNAS, Nov. 11, 2008. vol. 105, No. 45, pp. 17402-17407, https://doi.org/10.1073/pnas.0802781105.
Hanessian, Stephen et al., "Constrained azacyclic analogues of the immunomodulatory agent FTY720 as molecular probes for sphingosine 1-phosphate receptors", Bioorganic & Medicinal Chemistry Letters, vol. 17, 2007, pp. 491-494.
Hanessian et al., "Synthesis of a Conformationally Constrained Analog of N-Acetylmuramyl Dipeptide (MDP)", Synlett, 1991, Issue 4, pp. 222-224, DOI: 10.1055/s-1991-20684.
Hu et al., "A facile new procedure for the deprotection of allyl ethers under mild conditions", Canadian Journal of Chemistry, 2000, vol. 78, No. 6, pp. 838-845, https://doi.org/10.1139/v00-073.
Huwiler et al., "Stimulation by extracellular ATP and UTP of the mitogen-activated protein kinase cascade and proliferation of rat renal mesangial cells", Br J Pharmacol, Dec. 1994, vol. 113, No. 4, pp. 1455-1463.

(56) References Cited

OTHER PUBLICATIONS

Jain, M. et al., "Metabolite Profiling Identifies a Key Role for Glycine in Rapid Cancer Cell Proliferation", Science, May 25, 2012, vol. 336, Issue 6084, pp. 1040-1044, DOI: 10.1126/science.1218595.
Jefferies, H. B. et al., "A selective PIKfyve inhibitor blocks PtdIns(3,5)P2 production and disrupts endomembrane transport and retroviral budding", EMBO reports, 2008, vol. 9, pp. 164-170, first published online Jan. 11, 2008, DOI 10.1038/sj.embor.7401155.
Kabanov et al., "A new class of antivirals: antisense oligonucleotides combined with a hydrophobic substituent effectively inhibit influenza virus reproduction and synthesis of virus-specific proteins in MDCK cells", FEBS Letters, vol. 259, Issue 2, Jan. 1, 1990, pp. 327-330.
Kanai, Fumihiko et al., "The PX domains of p47phox and p40phox bind to lipid products of PI(3)K", Nature Cell Biology, vol. 3, Jul. 2001, pp. 675-678, doi:10.1038/35083070.
Kerr, M. C. et al., "Inhibition of the PtdIns(5) kinase PIKfyve disrupts intracellular replication of Salmonella", The EMBO Journal, 2010, vol. 29, pp. 1331-1347, first published online Published online Mar. 18, 2010, DOI 10.1038/emboj.2010.28.
Kiuchi, Masatoshi , "Synthesis and Immunosuppressive Activity of 2-Substituted 2-Aminopropane-1,3-diols and 2-Aminoethanolsl,2", J. Med. Chem., 2000, vol. 43, No. 15, pp. 2946-2961, DOI: 10.1021/jm000173z, Published Online Jul. 11, 2000.
Kono, M et al., "Sphingosine-1-phosphate receptor 1 reporter mice reveal receptor activation sites in vivo", J Clin Invest., May 1, 2014, vol. 124, No. 5, pp. 2076-2086, Published online Mar. 25, 2014, doi: 10.1172/JCI71194.
Lee, Terence, "FTY720: A Promising Agent for Treatment of Metastatic Hepatocellular Carcinoma", Clinical Cancer Research, Dec. 2005, vol. 11, Issue 23, pp. 8458-8466, DOI: 10.1158/1078-0432.CCR-05-0447.
Letsinger et al., "Cholesteryl-conjugated oligonucleotides: synthesis, properties, and activity as inhibitors of replication of human immunodeficiency virus in cell culture", PNAS, Sep. 1, 1989, vol. 86, No. 17, pp. 6553-6556.
Leumann, "DNA Analogues: From Supramolecular Principles to Biological Properties", Bioorganic & Medicinal Chemistry, vol. 10, Issue 4, Apr. 2002, pp. 841-854.
Lim, Keng G., "(R)-FTY720 methyl ether is a specific sphingosine kinase 2 inhibitor: Effect on sphingosine kinase 2 expression in HEK 293 cells and actin rearrangement and survival of MCF-7 breast cancer cells", Cellular Signalling, vol. 23, Issue 10, Oct. 2011, pp. 1590-1595, https://doi.org/10.1016/j.cellsig.2011.05.010.
Maddocks, O. D. K. et al., "Serine starvation induces stress and p53-dependentmetabolic remodelling in cancer cells", Nature, vol. 493, Jan. 24, 2013, pp. 542-546, first published Dec. 16, 2012, doi:10.1038/nature11743.
McCartney, Amber J. et al., "Phosphatidylinositol 3,5-bisphosphate: Low abundance, high significance", Prospects & Overviews, vol. 36, Issue 1, Jan. 2014, pp. 52-64, https://doi.org/10.1002/bies.201300012, First Published Oct. 28, 2013.
McCracken, A. N. et al., "Nutrient transporters: the Achilles' heel of anabolism", Trends in Endocrinology & Metabolism, vol. 24, Issue 4, Apr. 2013, pp. 200-208, https://doi.org/10.1016/j.tem.2013.01.002.
Nishina et al., "Chimeric Antisense Oligonucleotide Conjugated to α-Tocopherol", Molecular Therapy—Nucleic Acids, vol. 4, 2015, e220, 10 pages, https://doi.org/10.1038/mtna.2014.72.
Nishina et al., "Efficient in Vivo Delivery of siRNA to the Liver by Conjugation of α-Tocopherol", Molecular Therapy, vol. 16, Issue 4, Apr. 2008, pp. 734-740, https://doi.org/10.1038/mt.2008.14.
Palm, W. et al., "The Utilization of Extracellular Proteins as Nutrients Is Suppressed by mTORC1", Cell, vol. 162, Issue 2, Jul. 16, 2015, pp. 259-270, https://doi.org/10.1016/j.cell.2015.06.017.
Pate, K. T. et al., "Wnt signaling directs a metabolic program of glycolysis and angiogenesis in colon cancer", The EMBO Journal, 2014, vol. 33, pp. 1454-1473, first published online Published online May 13, 2014, DOI 10.15252/embj.201488598.
Pchejetski, D. et al., "FTY720 (Fingolimod) Sensitizes Prostate Cancer Cells to Radiotherapy by Inhibition of Sphingosine Kinase-1", Cancer Research, Nov. 2010, vol. 70, Issue 21, pp. 8651-8661, DOI: 10.1158/0008-5472.CAN-10-1388.
Pieters, R. et al., "L-Asparaginase treatment in acute lymphoblastic leukemia", Cancer, vol. 117, Issue 2, Jan. 15, 2011, pp. 238-249, First published Sep. 7, 2010, https://doi.org/10.1002/cncr.25489.
Romero, Rosales K. et al., "Sphingolipid-based drugs selectively kill cancer cells by down-regulating nutrient transporter proteins", Biochemical Journal, Oct. 15, 2011, vol. 439, No. 2, pp. 299-311, DOI: 10.1042/BJ20110853.
Rutherford, Anna C. et al., "The mammalian phosphatidylinositol 3-phosphate 5-kinase (PIKfyve) regulates endosome-to-TGN retrograde transport", Journal of Cell Science, vol. 119, Issue 19, 2006, pp. 3944-3957, http://dx.doi.org/10.1242/jcs.03153.
Schwarzenböck et al., "Choline PET and PET/CT in Primary Diagnosis and Staging of Prostate Cancer", Theranostics, 2012, vol. 2, No. 3, pp. 318-330, published online Mar. 15, 2012, doi: 10.7150/thno.4008.
Stingari, C. et al., "In Vivo Single-Cell Detection of Metabolic Oscillations in Stem Cells", Cell Reports, vol. 10, Issue 1, Jan. 6, 2015, pp. 1-7, https://doi.org/10.1016/j.celrep.2014.12.007.
Stingari, C. et al., "Metabolic trajectory of cellular differentiation in small intestine by Phasor Fluorescence Lifetime Microscopy of NADH", Scientific Reports, vol. 2, Article 568, 2012, 9 pages, first published Aug. 10, 2012, doi:10.1038/srep00568.
Stringari, Chiara et al., "Phasor approach to fluorescence lifetime microscopy distinguishes different metabolic states of germ cells in a live tissue", PNAS, Aug. 16, 2011, vol. 108, No. 33, pp. 13582-13587, https://doi.org/10.1073/pnas.1108161108.
Suhalim et al., "Characterization of Cholesterol Crystals in Atherosclerotic Plaques Using Stimulated Raman Scattering and Second-Harmonic Generation Microscopy", Biophysical Journal, vol. 102, Issue 8, Apr. 18, 2012, pp. 1988-1995, https://doi.org/10.1016/j.bpj.2012.03.016.
Sun, Chaode et al., "A Photoreactive Analogue of the Immunosuppressant FTY720", J. Org. Chem., 2006, vol. 71, No. 5, pp. 2200-2202, DOI: 10.1021/jo0526237, Publication Online Feb. 9, 2006.
Tuveson et al., "Endogenous oncogenic K-rasG12D stimulates proliferation and widespread neoplastic and developmental defects", Cancer Cell, vol. 5, Issue 4, Apr. 2004, pp. 375-387, https://doi.org/10.1016/S1535-6108(04)00085-6.
Valentine, William J. et al., "(S)-FTY720-Vinylphosphonate, an analogue of the immunosuppressive agent FTY720, is a pan-antagonist of sphingosine 1-phosphate GPCR signaling and inhibits autotaxin activity", Cellular Signalling, vol. 22, Issue 10, Oct. 2010, pp. 1543-1553, https://doi.org/10.1016/j.cellsig.2010.05.023.
Van Huis et al., "Exploration of 4,4-disubstituted pyrrolidine-1,2-dicarboxamides as potent, orally active Factor Xa inhibitors with extended duration of action", Bioorganic & Medicinal Chemistry, vol. 17, Issue 6, Mar. 15, 2009, pp. 2501-2511, https://doi.org/10.1016/j.bmc.2009.01.063.
Vicinanza, M. et al., "PI(5)P Regulates Autophagosome Biogenesis", Molecular Cell, vol. 57, Issue 2, Jan. 22, 2015, pp. 219-234, https://doi.org/10.1016/j.molcel.2014.12.007.
Wang, Wuyang et al., "Up-regulation of lysosomal TRPML1 channels is essential for lysosomal adaptation to nutrient starvation", PNAS, Mar. 17, 2015, vol. 112, No. 11, pp. E1373-E1381; published online Mar. 2, 2015, https://doi.org/10.1073/pnas.1419669112.
Welsch, C. A. et al., "Genetic, Biochemical, and Transcriptional Responses of Saccharomyces cerevisiae to the Novel Immunomodulator FTY720 Largely Mimic Those of the Natural Sphingolipid Phytosphingosine", The Journal of Biological Chemistry, Aug. 27, 2004, vol. 279, pp. 36720-36731, First Published on Jun. 9, 2004, doi: 10.1074/jbc.M406179200.
White, E., "Exploiting the bad eating habits of Ras-driven cancers", Genes & Dev., 2013, vol. 27, pp. 2065-2071, doi: 10.1101/gad.228122.113.
Wu et al., "Lipid metabolism in prostate cancer", Am J Clin Exp Urol., 2014, vol. 2, No. 2, pp. 111-120, Published Online Jul. 15, 2014.

(56) References Cited

OTHER PUBLICATIONS

Zhang, Y. et al., "Modulation of synaptic function by VAC14, a protein that regulates the phosphoinositides PI(3,5)p2 and PI(5)P", The EMBO Journal, 2012, vol. 31, pp. 3442-3456, Published online Jul. 27, 2012, DOI 10.1038/emboj.2012.200.

Zhu, Ran et al., "Asymmetric Synthesis of Conformationally Constrained Fingolimod Analogues—Discovery of an Orally Active Sphingosine 1-Phosphate Receptor Type-1 Agonist and Receptor Type-3 Antagonist", J. Med. Chem., vol. 50, No. 25, 2007, pp. 6428-6435, DOI: 10.1021/jm7010172, published online Nov. 10, 2007.

Zolov, S. N. et al., "In vivo, Pikfyve generates PI(3,5)P2, which serves as both a signaling lipid and the major precursor for PI5P", PNAS, Oct. 23, 2012, vol. 109, No. 43, pp. 17472-17477, https://doi.org/10.1073/pnas.1203106109.

\* cited by examiner

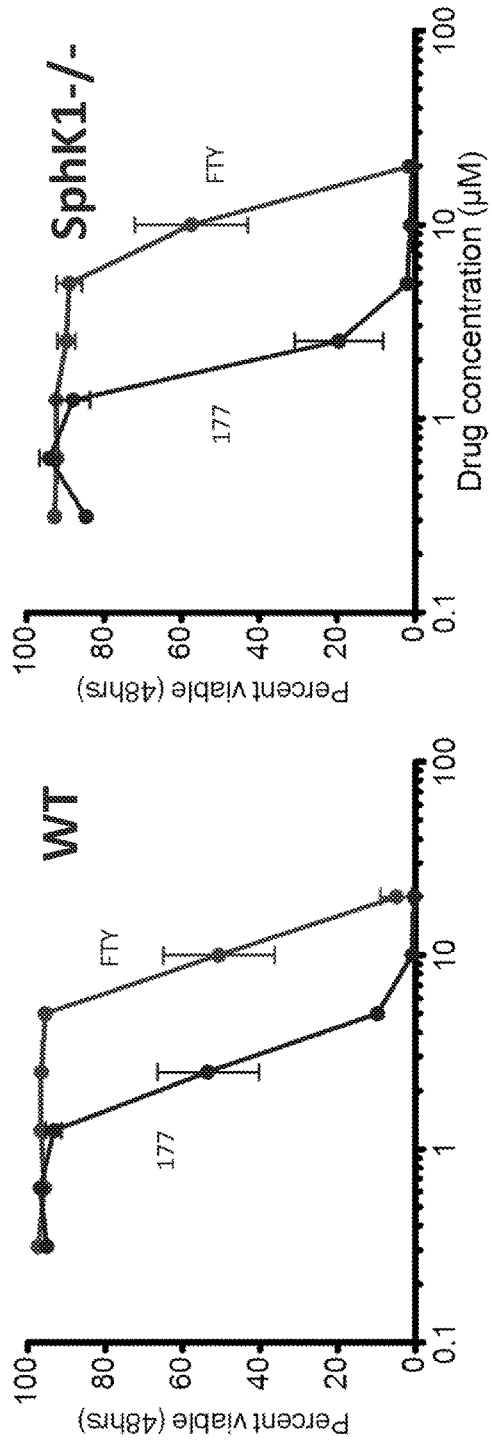
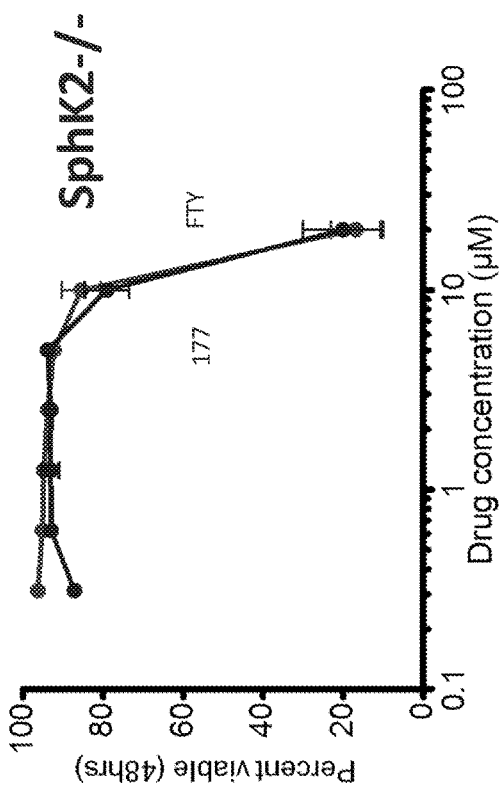
FIG. 10h
FIG. 10i
FIG. 10j

AZACYCLIC CONSTRAINED ANALOGS OF FTY720

STATEMENT REGARDING FEDERALLY SPONSORED RESEARCH OR DEVELOPMENT

This invention was made with Governmental support under Grant Nos. T32CA009054 awarded by the National Cancer Institute, W81XWH-11-1-0535 awarded by the Department of Defense, and R01 GM089919 awarded by the National Institute of Health, the National Institute of General Medical Sciences. The government has certain rights in the invention

FIELD OF THE INVENTION

The invention is generally directed to azacyclic constrained analogs of FTY720, medicaments formed from these analogs, and methods for the treatment of disorders using such therapeutics.

BACKGROUND

Sphingosine-1 phosphate receptors (S1P) are found on the surface of many cell types. S1P receptors are activated by binding sphingosine-1 phosphate. There are five types of S1P receptors, each of which triggers distinct signal transduction pathways. S1P binding to S1P receptors may activate different cellular functions, including cell proliferation and differentiation, cell survival, cell invasion, lymphocyte trafficking, and cell migration.

FTY720 is an immunosuppressant prodrug that functions by antagonizing S1P receptors. In its active, phosphorylated state, FTY720 binds four of the five S1P receptors. FTY720 binding to S1P1 causes receptor activation and subsequent down-regulation trapping lymphocytes in secondary lymphoid organs. Currently, FTY720 is marketed to treat relapsing-remitting multiple sclerosis (MS). Previous publications describe broad classes of FTY720 analogs for use in selectively binding S1P receptors.

SUMMARY OF THE INVENTION

In many embodiments the invention is directed to small molecules in the nature of azacyclic constrained analogs of FTY720, medicaments formed from these small molecules, and methods for the treatment of disorders using such therapeutics are disclosed.

In some embodiments, aspects of the invention are directed to compounds having the following molecular formula:

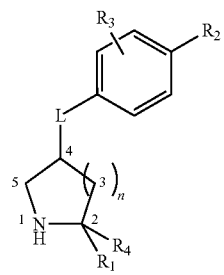

wherein:
$R_1$ is an optional functional group selected from an alkyl chain, $(CH_2)_nOH$, CHOH-alkyl, CHOH-alkyne, and $(CH_2)_nOMe$;
$R_2$ is an aliphatic chain ($C_6$-$C_{10}$);
$R_3$ is a mono-, di-, tri- or quad-aromatic substituent comprising hydrogen, halogen, alkyl, alkoxy, azide ($N_3$), ether, $NO_2$, or cyanide (CN);
$R_4$ is an optional alcohol ($CH_2OH$) with $R_1$;
L is O—$CH_2$;
Me is an alkyl, alkene or alkyne;
n is an independently selected whole integer selected from 1 to 3; and
wherein the phenyl can be moved along the $R_2$ or $R_3$ carbon chain.

In some such embodiments, the compound stimulates PP2A activity.

In other such embodiments, the stereochemistry of the compound is selected from the group consisting of S at position 2 and R at position 4, R at position 2 and S at position 4, R at position 2 and R at position 4, and S at position 2 and S at position 4.

In still other such embodiments, the functional groups attached to the pyrrolidine group are in a cis relative orientation.

In yet other such embodiments, the functional groups attached to the pyrrolidine group are in a trans relative orientation.

In still yet other such embodiments $R_1$ is an alkyl chain having 1 to 6 carbons.

In still yet other such embodiments, the compound is in the form of a salt. In some such embodiments the salt is a pharmaceutically acceptable salt.

In still yet other such embodiments, the compound is phosphorylated. In some such embodiments the compound is phosphorylated at any hydroxymethyl group.

In still yet other such embodiments, the compound shows reduced activity against binding S1P receptors when compared to FTY720. In some such embodiments, the compound shows reduced activity against binding S1P1 and S1P3 receptors when compared to FTY720. In some embodiments, the compound has activity in down-regulating cellular nutrient transport.

In still yet other such embodiments, $R_2$ is $C_8H_{17}$ and $R_1$ is $CH_2OH$.

In still yet other embodiments, $R_1$ is a phosphate or phosphonate, such as, for example, $(CH_2)_nPO(OH)_2$ and esters thereof, CH=CHPO(OH)$_2$ and esters thereof, $(CH_2CH_2)_nPO(OH)_2$ and esters thereof, and $(CH_2)_nOPO(OH)_2$ and esters thereof.

In other embodiments, aspects of the invention are directed to a medicament for the treatment of a disorder including: a pharmaceutical formulation containing a therapeutically effective amount of one or more azacyclic constrained FTY720 analog small molecule compounds.

In some such embodiments, the medicament is directed toward the treatment of a disorder selected from the group consisting of cancer, leukemia, diabetes and obesity.

In other such embodiments, the medicament is formulated for a form of administration selected from the group consisting of oral, parenteral, and transdermal.

In still other such embodiments, the compound stimulates PP2A activity.

In yet other such embodiments, the compound shows reduced activity against binding S1P receptors when compared to FTY720.

In still yet other such embodiments, the compound shows reduced activity against binding S1P1 and S1P3 receptors when compared to FTY720.

In still other embodiments, aspects of the invention are drawn to a method of treating disease in a patient including:
diagnosing a patient having a disorder susceptible to treatment at least in part by cellular nutrient down-regulation; and
administering a therapeutic amount of one or more azacyclic constrained FTY720 analog small molecule compounds effective in down-regulating cellular nutrient transport.

BRIEF DESCRIPTION OF THE DRAWINGS

The description and claims will be more fully understood with reference to the following figures and data graphs, which are presented as exemplary embodiments of the invention and should not be construed as a complete recitation of the scope of the invention.

FIGS. 3a to 3l provide reaction pathways for the production of therapeutic small molecule analogs in accordance with various embodiments of the invention.

DETAILED DESCRIPTION

Turning now to the drawings and data, small molecules capable of treating disorders, including cancer, from a variety of therapeutic mechanisms including triggering cellular nutrient transporter down-regulation, medicaments formed from these small molecules, and methods for the treatment of disorders using such therapeutics are disclosed. In some embodiments, the small molecules are azacyclic constrained analogs of FTY720. Additional embodiments of the small molecules are o-benzyl pyrrolidines. Embodiments can exist in a pure compound form or in the form of pharmaceutically effective salts. Some embodiments inhibit cellular nutrient transport by stimulating PP2A activity. In other embodiments, formulations and medicaments are provided that are directed to the treatment of disease. In some such embodiments these formulations and medicaments target cancers, such as, for example, leukemia, and potentially other diseases. Therapeutic embodiments contain a therapeutically effective dose of one or more small molecule compounds, present either as pharmaceutically effective salt or in pure form. Embodiments allow for various formulations, including, but not limited to, formulations for oral, intravenous, or intramuscular administration. Other additional embodiments provide treatment regimes for disorders using therapeutic amounts of the small molecules. In some treatment embodiments the small molecules, delivery systems and dosage regimes are directed to the treatment of cancers, such as, for example, leukemia and potentially other diseases, including diseases in which nutrient transport down-regulation is therapeutically effective.

Definitions

For the purposes of this description, the following definitions are used, unless otherwise described.

"Sphingosine-1 phosphate (SIP)" is formed in cells in response to diverse stimuli and plays an important role in cell signaling.

"SIP receptor" is any receptor that binds molecules including, but not limited to, S1P, FTY720, and any analogs of FTY720 or S1P. This class of receptors includes any of the known G-protein coupled types of S1P receptors.

"Nutrient transport" refers to a cell's capacity to regulate the import and export of metabolically relevant chemical compounds including but not limited to amino acids, glucose, and iron.

"PP2A" is a serine/threonine phosphatase that plays a role in inactivating signal transduction pathways, antagonizes the action of Bcl-2 family members including Bcl-2 and Bad, and in regulating many other cellular processes.

Figure 1:
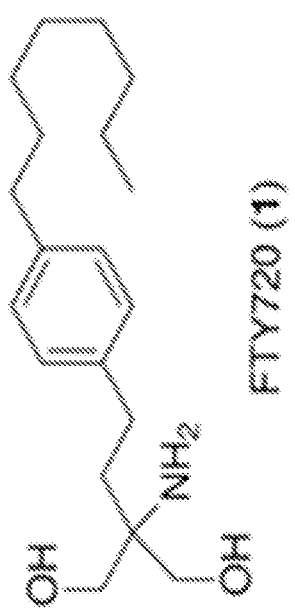
FIG. 1 provides a molecular structure of FTY720.

"FTY720" (2-Amino-2-[2-(4-octylphenyl)ethyl]propane 1,3-diol hydrochloride), shown diagrammatically in FIG. 1, is a synthetic immunomodulatory agent bearing an aminodiol functionality on an aromatic moiety bearing a hydrophobic aliphatic chain. It is presently marketed under the trade name Gilenya™ for the treatment of relapsing-remitting multiple sclerosis.

"Selective" refers to a compound ligand directed toward a specific receptor site. At the binding site, the compound can act to agonize or antagonize the target molecule. This can be done directly or indirectly by affecting a step in a signal transduction pathway that regulates the activity of a specific target protein.

The terms "phosphate precursor" and "phosphate precursor analog" refer to substituent moieties in invention compounds that may be directly phosphorylated in vivo.

"Phosphate derivative" refers to substituent moieties in invention compounds that contain a phosphate or phosphate ester group.

"Prodrug" refers to a compound that becomes biologically active in vivo only after phosphorylation.

Terms Of Art

"Acyl" means a —R—C=O group.

"Acyl phosphate" means an acyl group bonded to a phosphate, $RCO_2PO_3^{2-}$.

"Alcohol" means a compound with an —OH group bonded to a saturated, alkane-like compound, (ROH).

"Alkyl" refers to the partial structure that remains when a hydrogen atom is removed from an alkane.

"Alkane" means a compound of carbon and hydrogen that contains only single bonds.

"Alkene" refers to a hydrocarbon that contains a carbon-carbon double bond, $R_2C=CR_2$.

"Alkyne" refers to a hydrocarbon structure that contains a carbon-carbon triple bond.

"Alkoxy" refers to a portion of a molecular structure featuring an alkyl group bonded to an oxygen atom.

"Aryl" refers to any functional group or substituent derived from an aromatic ring.

"Amine" molecules are compounds containing one or more organic substituents bonded to a nitrogen atom, $RNH_2$, $R_2NH$, or $R_3N$.

"Amino acid" refers to a difunctional compound with an amino group on the carbon atom next to the carboxyl group, $RCH(NH_2)CO_2H$.

"Azide" refers to $N_3$

"Cyanide" refers to CN.

"Ester" is a compound containing the —$CO_2R$ functional group.

"Ether" refers to a compound that has two organic substituents bonded to the same oxygen atom, i.e., R—O—R'.

"Halogen" or "halo" means fluoro (F), chloro (Cl), bromo (Br), or iodo (I).

"Hydrocarbon" means an organic chemical compound that consists entirely of the elements carbon (C) and hydrogen (H).

"Phosphate", "phosphonate", or "PO" means a compound containing the elements phosphorous (P) and oxygen (O).

"R" in the molecular formula above and throughout are meant to indicate any suitable organic molecule.

Introduction

FTY720 is a well-known immunosuppressant, and has been the subject of intensive research. When employed as an immunosuppressant, FTY720 is a pro-drug. In vivo phosphorylation leads specifically to the pro-S-phosphate ester isomer. Once phosphorylated, FTY720 acts as a functional antagonist binding to S1P receptors, which stimulates lymphocytic migration to secondary lymphoid tissues causing circulating lymphocytes to be sequestered. In other words, FTY720 suppresses the immune system by taking immune cells out of circulation.

In recent years, scientists have begun to propose FTY720 for use as an anticancer agent. Suggested approaches include: (1) designing FTY720 with selective activity toward specific S1P receptors; and (2) the use of FTY720 to promote PP2A activation, resulting in down-regulation of the oncogenic Bcl-2 family proteins. (See, e.g., Coffin, A. et al. WO 2008/097819; and Byrd, J. C. et al., US 2013/0123366, the disclosures of which are incorporated herein by reference.) For example, some believe that engineering FTY720 analogs directed to a specific subset of S1P receptors can mitigate the harsh side effects associated with high doses of FTY720. (See, e.g., WO 2008/097819, cited above.) In particular, in an effort to study the stereochemistry of phosphorylation, a number of synthetic analogs of FTY720 that focus mainly on the polar subunit have been generated and the biological activities of the resulting phosphate esters reported. These studies particularly focused on finding the appendages that would be optimal for activity at S1P receptors. (See, e.g., Clemens, J. J., et al., *Bioorg. Med. Chem. Lett.* 2005, 15, 3568-3572; Hanessian, S. et al., *Bioorg. Med. Chem. Lett.* 2007, 17, 491-494; Davis, M. D. et al., *J. Biol. Chem.* 2005, 280, 9833-9841; Zhu, R. et al., *J. Med. Chem.* 2007, 50, 6428-6435; Forrest, M. et al., *J. Pharmacol. Exp. Ther.* 2004, 309, 758-768.; Valentine, W. J. et al., *Cell. Signal.* 2010, 22, 1543-1553; Lim, K. G. et al., *Cell Signal.* 2011, 23, 1590-1595; Sun, C. & Bittman, R., *J. Org. Chem.* 2006, 71, 2200-2202; and Kiuchi, M. et al., *J. Med. Chem.* 2000, 43, 2946-2961, the disclosures of each of which are incorporated herein by reference.)

In contrast, others believed that FTY720 itself, not any particular analog, can be used to treat leukemia by stimulating the activity of PP2A, a serine/threonine phosphatase, despite the molecule's inherent activity to S1P receptors. (See, e.g., US 2013/0123366, cited above.) PP2A and other phosphatases play important roles in inactivating signal transduction pathways and antagonizing Bcl-2 family proteins. (See, e.g., See Deng et al., *Blood*, 113(2): 422-8 (2009), the disclosure of which is incorporated herein by reference.) In many cancers where there is uncontrollable cellular proliferation, phosphatase activity is reduced and Bcl-2 family proteins have an anti-apoptotic effect. (See, e.g., Reed, J. C., *Blood* 111(7): 3322-30, the disclosure of which is incorporated herein by reference.) So in theory, by administering FTY720 to up-regulate PP2A phosphatase and down regulate Bcl-2, researchers propose to mitigate oncogenic cellular proliferation. (See, US 2013/0123366, cited above.) Though up-regulation of PP2A is the principal mechanism underlying this treatment strategy, inherent to any use of FTY720 is activation of S1P receptors. (See, e.g., Brinkmann, V., *J. Pharmacol.* 2009, 158, 1173-1182; and Tigyi, G. et al., *FASEB J.*, Apr. 24, 2010, Meeting Abstract Supplement 1b/100, the disclosures of which are incorporated herein by reference.) Thus, though investigators employ different variations of the FTY720 molecule, activation of S1P receptors is inherent to both proposed anticancer treatments.

Unfortunately, administering the requisite amount of FTY720 needed for anticancer treatment has a significant downside. At the dose used to treat MS, FTY720 has been shown to be well tolerated, however, the elevated doses of FTY720 required for effective and selective anti-cancer treatment have been shown to cause bradycardia secondary to the activation of S1P1 and S1P3, a potentially lethal and therefore dose-limiting toxicity. (See, e.g., Lee, T. K. et al., *Clin. Cancer Res.* 2005, 11, 8458-8466; Azuma, H. et al., *Cancer Res.* 2002, 62, 1410-1419; Chua, C. W. et al., *Int. J. Cancer* 2005, 117, 1039-1048; Azuma, H. et al., *J. Urol.* 2003, 169, 2372-2377; Neviani, P. et al., *J. Clin. Invest.* 2007, 117, 2408-2421. Sanna, M. G., et al., *J. Biol. Chem.* 2004, 279, 13839-13848; and Koyrakh, L., et al., *Am. J. Transplant.* 2005, 5, 529-536, the disclosures of which are incorporated herein by reference.) So, despite the potential for use as an anticancer therapeutic, currently known FTY720-related compounds are dose-limited due to S1P receptor binding, making them untenable for anticancer use.

It has now been discovered that the relevant anticancer activity of FTY720 is separable from its S1P receptor activity. Indeed, it is now proposed that the high doses of FTY720 required for anti-cancer treatment stems not exclusively from S1P receptor effects, but at least in part from inhibition of nutrient transport. Accordingly, in sharp contrast to previous studies, safe and effective anticancer agents based on azacyclic constrained analogs of FTY720 that do not implicate FTY720's S1P receptor-related, dose-limiting toxicity are presented. Rather, the azacyclic constrained FTY720 analog embodiments, therapeutics and treatments proposed, treat cancer and other disorders at least in part by blocking nutrient transport, thereby starving—and killing— the diseased cells. Additionally, these compounds have the potential to up-regulate PP2A activity, which has additional anti-oncogenic and anti-proliferative effects. In sum, the azacyclic constrained analogs of FTY720 described herein employ several mechanisms to fight cancer without the lethal effects inherent to approaches taken by others in the field, and which make the use of FTY720 as an anticancer agent effectively untenable. Accordingly, presented below are embodiments of small molecule azacyclic constrained analogs of FTY720, therapeutics based on such small molecules, and treatment regimes incorporating such therapeutics for use in treating cancer and other disorders.

Inventive Molecules

Figure 2A:
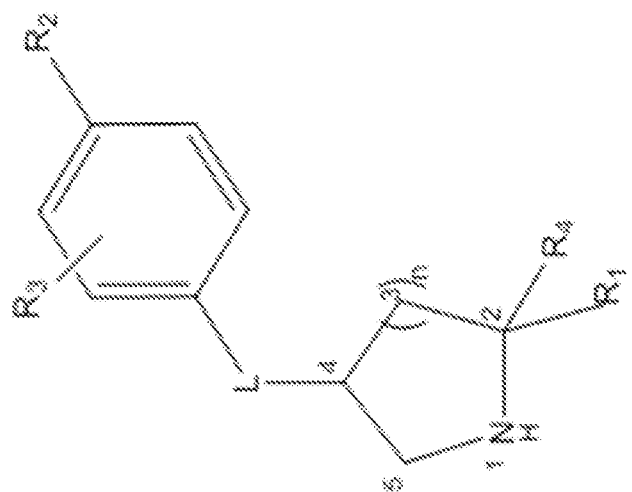
FIGS. 2a to 2e provide molecular structures of therapeutic small molecule analogs in accordance with embodiments of the invention.
Figure 2B:
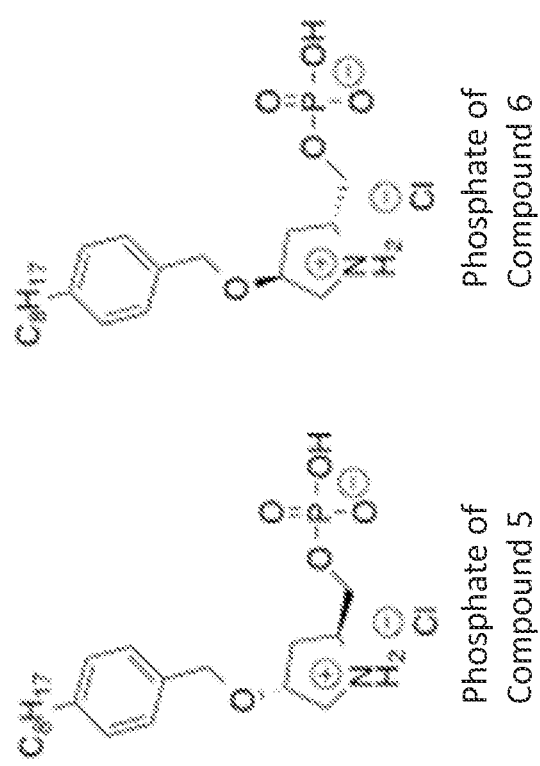
Figure 2C:
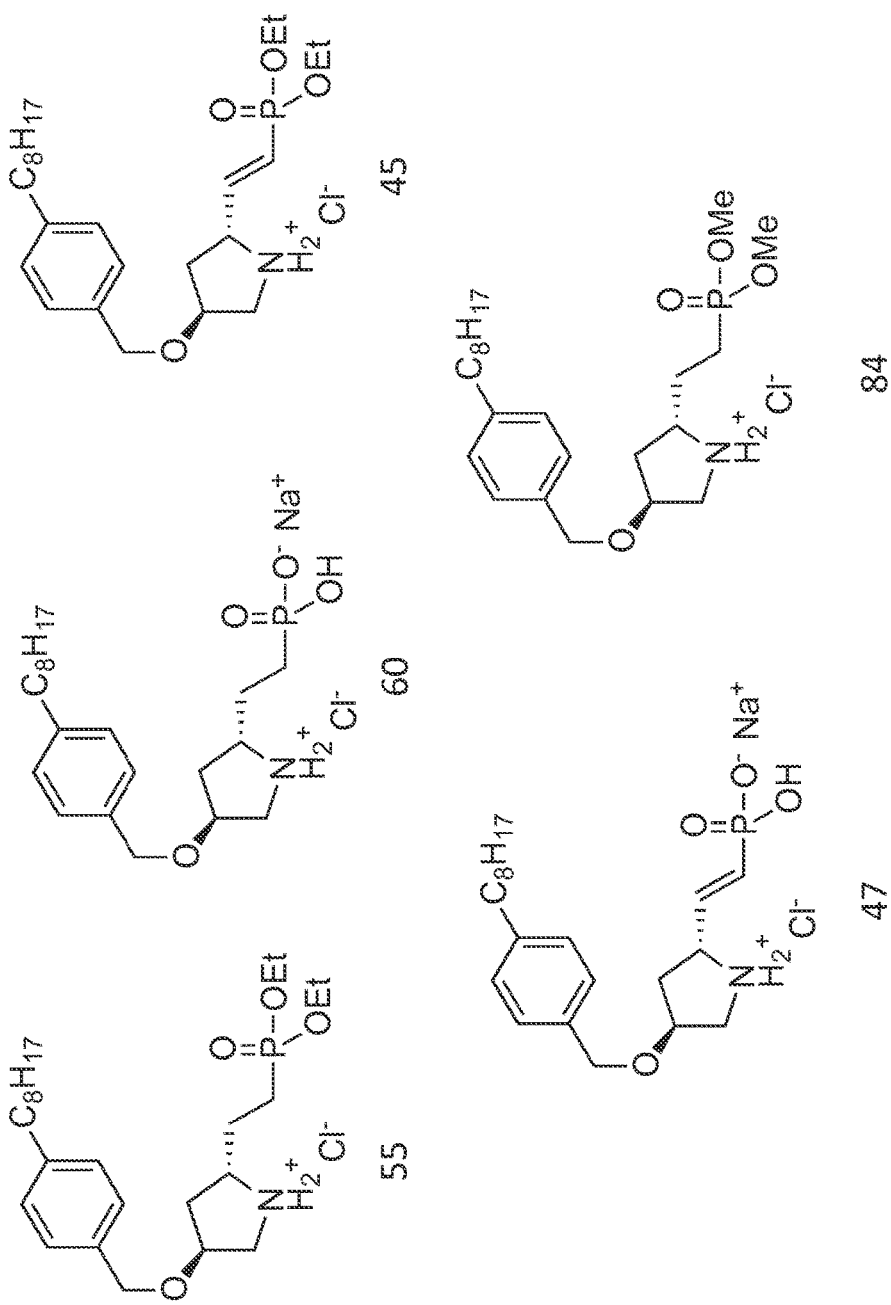
Figure 2D:
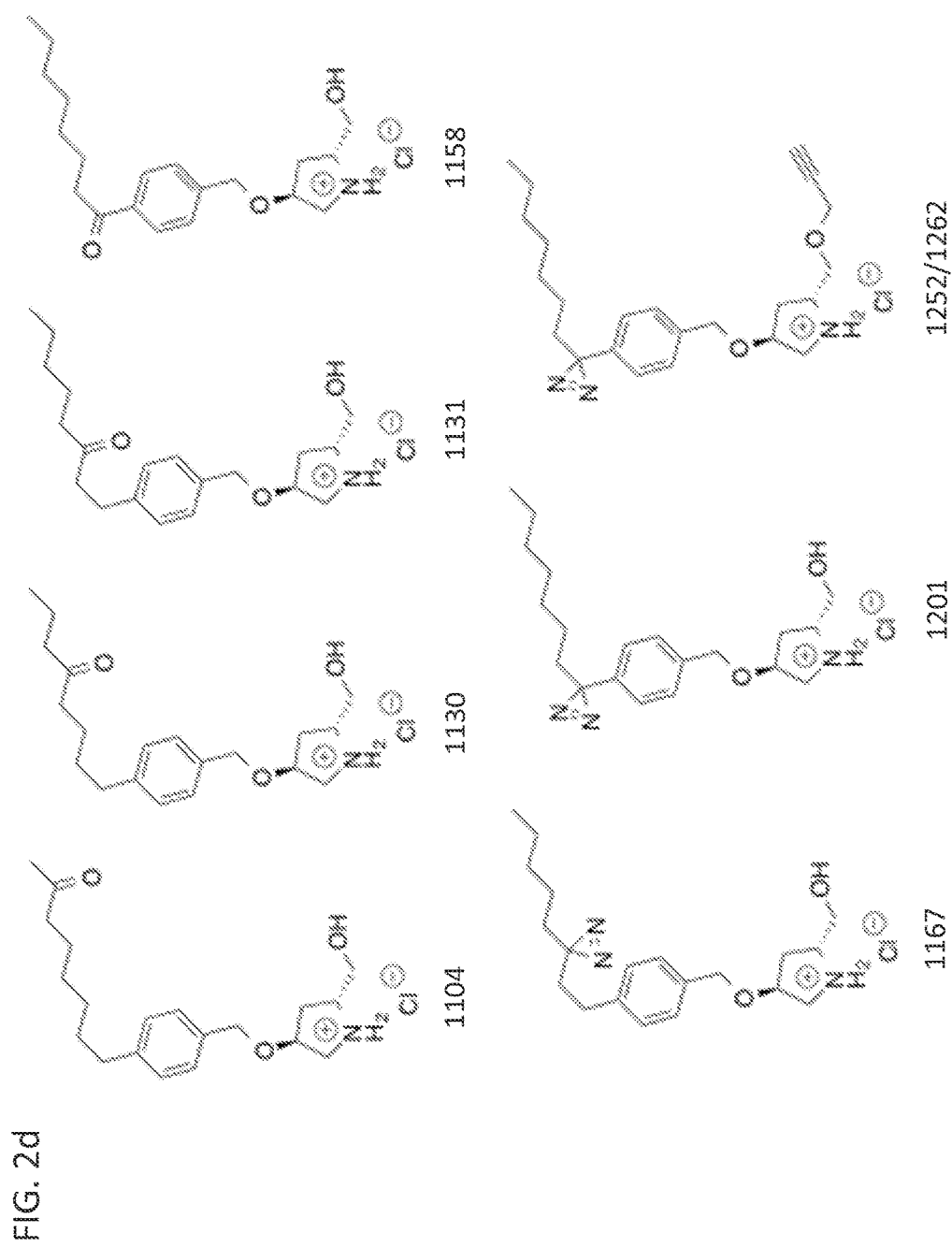

Compounds in accordance with embodiments of the invention are based on O-benzyl pyrrolidines. The chemical structure of FTY720 is illustrated in FIG. 1. A chemical compound in accordance with embodiments of the invention is illustrated in FIG. 2 and pictured below. Embodiments comprise the molecule as illustrated in FIG. 2a, phosphates of such molecules as illustrated in FIG. 2b, phosphonates of such molecules as illustrated in FIG. 2c, or a pharmaceutically acceptable salt thereof, wherein:

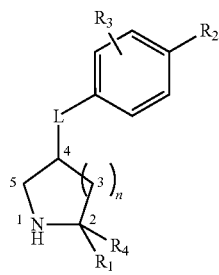

$R_1$ is an optional functional group selected from an alkyl chain, $(CH_2)_nOH$, CHOH-alkyl, CHOH-alkyne, $(CH_2)_nOMe$, $(CH_2)_nPO(OH)_2$ and esters thereof, $CH=CHPO(OH)_2$ and esters thereof, $(CH_2CH_2)_nPO(OH)_2$ and esters thereof, and $(CH_2)_nOPO(OH)_2$ and esters thereof;

$R_2$ is an aliphatic chain $(C_6-C_{10})$;

$R_3$ is a mono-, di-, tri- or quad-aromatic substituent comprising hydrogen, halogen, alkyl, alkoxy, azide $(N_3)$, ether, $NO_2$, or cyanide (CN);

$R_4$ is an optional alcohol $(CH_2OH)$ with $R_1$;

L is $O-CH_2$;

Me is an alkyl, alkene or alkyne;

n is an independently selected integer selected from 1, 2, or 3; and wherein the phenyl can be moved along the $R_2$ or $R_3$ carbon chain.

Figure 2E:
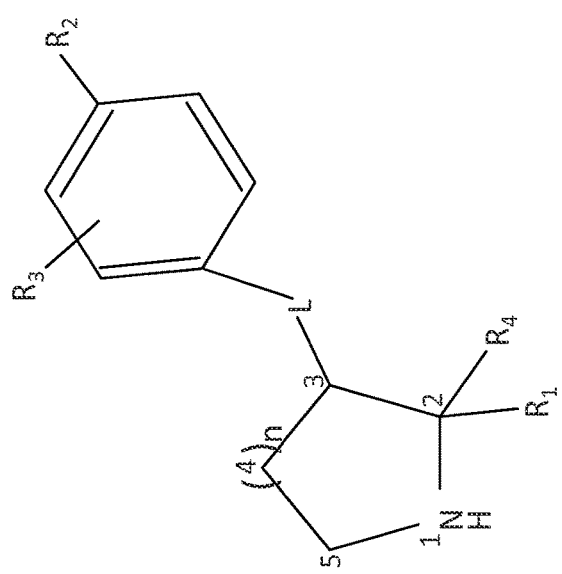

In further embodiments the O-benzyl group can be moved to position 3 or 4, where the position not occupied by the O-benzyl group is now H (i.e., $CH_2$), as shown in FIG. 2e, and reproduced below.

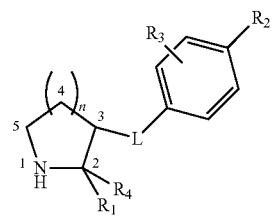

In additional embodiments, alkyl, $CH_2OH$, or $(CH_2)_nOH$ groups can be added to position 5.

In still other embodiments, the $R_2$ and $R_3$ substituents can have different combinations around the phenyl ring with regard to their position.

In still other embodiments, the $R_1$ may be an alkyl having 1 to 6 carbons.

It will be understood that compounds in this invention may exist as stereoisomers, including phosphate, phosphonates, enantiomers, diastereomers, cis, trans, syn, anti, solvates (including hydrates), tautomers, and mixtures thereof, are contemplated in the compounds of the present invention. (See, e.g., FIGS. 2b to 2c, 4a, 5a, 6a and 7a, for example.)

In many embodiments where the compound is a phosphate or phosphonate, $R_1$ may be, for example, $(CH_2)_nPO(OH)_2$ and esters thereof, $CH=CHPO(OH)_2$ and esters thereof, $(CH_2CH_2)_nPO(OH)_2$ and esters thereof, and $(CH_2)_nOPO(OH)_2$ and esters thereof.

The claimed invention can also be included in/relate to pharmaceutically acceptable salts. A "pharmaceutically acceptable salt" retains the desirable biological activity of the compound without undesired toxicological effects. Salts can be salts with a suitable acid, including, but not limited to, hydrochloric acid, hydrobromic acid, sulfuric acid, phosphoric acid, nitric acid and the like; acetic acid, oxalic acid, tartaric acid, succinic acid, malic acid, benzoic acid, pamoic acid, alginic acid, methanesulfonic acid, naphthalenesulphonic acid, and the like. Also, incorporated cations can include ammonium, sodium, potassium, lithium, zinc, copper, barium, bismuth, calcium, and the like; or organic cations such as tetraalkylammonium and trialkylammonium cations. Also useful are combinations of acidic and cationic salts. Included are salts of other acids and/or cations, such as salts with trifluoroacetic acid, chloroacetic acid, and trichloroacetic acid.

Other azacyclic constrained FTY720 analogs, as well as modified azacyclic constrained FTY720 analogs, suitable for practice of the present invention will be apparent to the skilled practitioner, and include any O-benzyl pyrrolidine compound that may employ several mechanisms including the inhibition or down-regulation of nutrient transport and/or the up-regulation of PP2A activity, without inducing toxic S1P receptor activity, even if not structurally identical to the compounds shown above.

Formulations

In embodiments, the small molecule azacyclic constrained FTY720 analogs are formulated into a therapeutic medicament for treatment of disorders, such as, for example, cancers susceptible to the inhibition of nutrient transport, or to PP2A activation. In such embodiments, the modes of administration for the therapeutics include, but are not limited to, oral, transdermal, transmucosal (e.g., sublingual, nasal, vaginal or rectal), or parenteral (e.g., subcutaneous, intramuscular, intravenous, bolus or continuous infusion). The actual amount of drug needed will depend on factors such as the size, age and severity of disease in the afflicted individual. The actual amount of drug needed will also depend on the effective inhibitory concentration ranges of the various azacyclic constrained analogs of FTY720. Different analogs have different effective inhibitory concentration ranges, as shown and described in greater detail in FIGS. 5 to 7, below.

Embodiments of therapeutics may be administered at dosages and for periods of time effective to reduce, ameliorate or eliminate the symptoms of diseases or pathological conditions susceptible to such treatment, such as, for example, cancers like leukemia. Other indications for use may include type-2 diabetes and obesity. For example, in embodiments where regulation of nutrient uptake is implicated, using various embodiments of the FTY720 small molecule compound may be used to restrict caloric uptake and/or extend lifespan. Dose regimens may be adjusted for purposes of improving the therapeutic or prophylactic response of the compound. For example, several divided doses may be administered daily, one dose, or cyclic administration of the compounds to achieve the desired therapeutic result. A single azacyclic constrained FTY720 analog small molecule compound may be administered, or combinations of various azacyclic constrained FTY720 analog small molecule compounds may also be administered.

It is also possible to add agents that improve the solubility of these compounds. For example, the claimed compounds can be formulated with one or more adjuvants and/or pharmaceutically acceptable carriers according to the selected route of administration. For oral applications, gelatin, flavoring agents, or coating material can be added. In general, for solutions or emulsions, carriers may include aqueous or alcoholic/aqueous solutions, emulsions or suspensions, including saline and buffered media. Parenteral vehicles can include sodium chloride and potassium chloride, among others. In addition, intravenous vehicles can include fluid and nutrient replenishers, electrolyte replenishers and the like.

Preservatives and other additives, like antimicrobial, antioxidant, chelating agents, and inert gases, can also be present. (See generally, Remington's Pharmaceutical Sciences, 16th Edition, Mack, (1980), the disclosure of which is incorporated herein by reference.)

Exemplary Embodiments

Biological data supports the use of the aforementioned azacyclic constrained analogs of FTY720 in a variety of embodiments to treat disease (cancer, obesity, diabetes). Above, are described embodiments incorporating small molecule compounds, medicaments, and as part of treatment regimes. Previous studies have established that chemical modifications to the flexible aminodiol portion of FTY720 influence the selective binding to S1P receptors. (Clemens, J. J. et al., cited above.) It is noted that embodiments of azacyclic constrained analogs of FTY720 in accordance with the disclosure kill cells at least in part by starvation with reduced activity toward the binding of the S1P receptors, thereby avoiding lethal side effects, like bradycardia. Accordingly, embodiments using these compounds to treat various diseases avoid the pitfalls associated with prior approaches. As will be discussed, data supports the proposition that small molecule azacyclic constrained FTY720 analog embodiments according to the disclosure are superior to existing FTY720-related molecules and related treatment methods.

The expected therapeutic efficacy of the azacyclic constrained FTY720 analog small molecule embodiments stems from its demonstrated biological activity in preliminary studies using Sup-B15 leukemia cells. As discussed below, minor chemical and structural modifications, including changes to stereochemistry, O-benzyl chain position, loss of phosphorylation sites, and length of aliphatic chain, have a slight effect on FTY720 small molecule analog activity, but all analogs still show therapeutic advantages over the FTY720 control.

Materials and Methods

Synthesis: Embodiments include enantiomerically pure and stereochemically diverse O-substituted benzyl ethers of pyrrolidines starting with appropriately substituted 2- and 4-hydroxy D- or L-prolines. Some listed embodiments of the azacyclic constrained FTY720 analog small molecule compound originate from similar reactions. For compounds 5, 6, 7, 8, 13, 14, and 15 molecular precursors can be purchased in place of carrying out the full synthesis reaction. The aforementioned precursors are all known compounds and spectral data were in agreement with the proposed structures and matched those in literature. Compounds 5 and 6 begin with different stereoisomers of (2R,4S)-1-Boc-2-(tert-butyldimethylsilyloxymethyl)-4-hydroxypyrrolidine (6d, from FIG. 3b) (versus (2S,4R) for compound 5). Remaining steps are routine, with the exception of final step, which is broken up into two steps for compound 6 because this generates a precursor for compounds 14 and 15. (See FIG. 3a & b.)

Figure 3A:
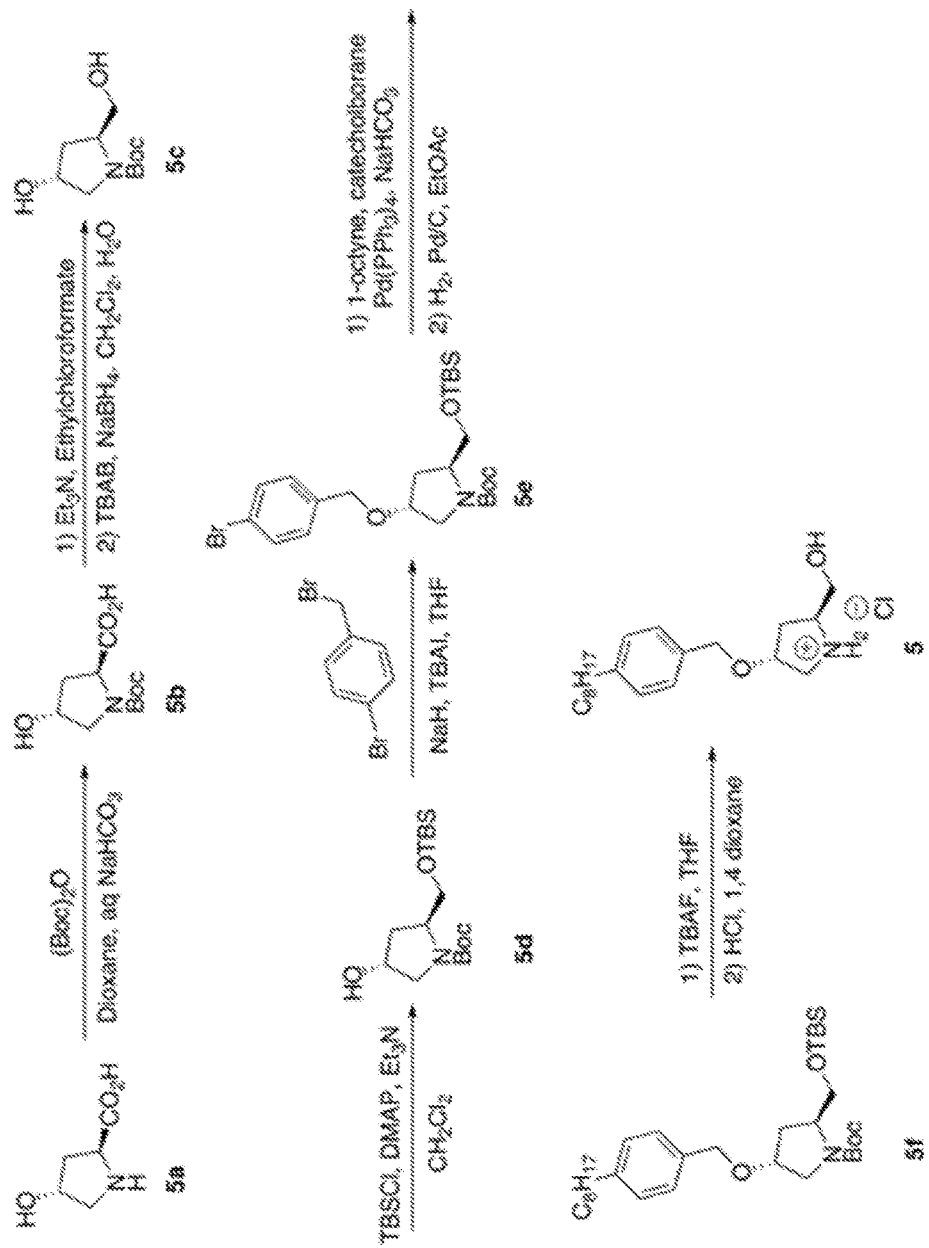

For compound 5, as illustrated in FIG. 3a, the synthesis of compound 5 is a six step process. However, compounds 5b, 5c, and 5d are all known compounds consistent with the precursors mentioned above. As such, relevant synthesis reactions begin with compound 5e. To synthesize compound 5e ((2S,4R)-1-Boc-4-(4-bromobenzyl)oxy)-2-(tert-butyldimethylsilyloxymethyl)-hydroxypyrrolidine), compound 5d (495 mg, 1.5 mmol) is dissolved in dry THF (10 mL), purged with Argon and cooled to 0° C. before NaH (60% in mineral oil, 180 mg, 4.5 mmol). The mixture is stirred for 30 minutes before adding 4-bromobenzyl bromide. Following, the reaction is quenched with water, diluted with EtOAc and washed with water and brine, dried over $MgSO_4$ and filtrated. Solvent is removed under reduced pressure and the residue purified by flash chromatography. This yields compound 5e, or (2S,4R)-1-Boc-4-(4-bromobenzyl)oxy)-2-(tert-butyldimethylsilyloxymethyl)-4-hydroxypyrrolidine. (FIG. 3a).

Next, in a two-step reaction, a solution of 1-octyne (44 µL, 0.3 mmol) and catecholborane (1.0M in THF, 0.3 mL, 0.3 mmol) was refluxed at 70° C. for 2 hours under Argon atmosphere. The reaction mixture was allowed to cool down to room temperature. A solution of 5e (100 mg, 0.2 mmol) in DME (2 mL) was added to the reaction mixture followed by $Pd(PPh_3)_4$ (6.9 mg, 0.006 mmol) and 1N aqueous solution of $NaHCO_3$ (2 mL). The reaction mixture is refluxed with vigorous stirring overnight. The mixture is then cooled to room temperature and a brine solution added. The mixture is extracted 3 times with $Et_2O$ and the combined organic layers were dried over $Na_2SO_4$ and filtrated. The solvent is removed over reduced pressure and the residue is purified by flash chromatography (hexane: EtOAc, 9:1) to give a colorless oil (36 mg, 34%). This oil is then dissolved in EtOAc and Pd/C (10%) is added. The air is pumped out of the flask and replaced by $H_2$. Upon completion as indicated by TLC, the reaction is stopped and the mixture filtered through a pipette with cotton and Celite. The solvent is removed under reduced pressure to give hydrogenation product compound 5f. (29 mg, 83%) as a colorless oil. Finally, to synthesize compound 5 from compound 5f, TBAF (1.0 M in THF, 95 µL, 0.095 mmol) is added to a solution of compound 5f (29 mg, 0.054 mmol) in dry THF (1.3 mL). The reaction is then stirred in room temperature for 3 hours. When no more starting material was visible on TLC, the reaction mixture is quenched with saturated solution of $NaHCO_3$ and triple extracted with $CH_2Cl_2$. Then, the organic layers are combined, dried over $Na_2SO_4$ and filtered. The solvent is removed under reduced pressure and the residue purified by flash chromatography (hexane: EtOAc, 6:4) to give the alcohol (20 mg, 88%) as a colorless oil. The alcohol is next dissolved in a 4.0 M HCl solution in dioxane (1.2 mL) and the mixture is stirred in room temperature overnight. In embodiments related to compound 5, MS and TLC analysis of the crude mixture shows only the desired compound. The solvent is evaporated and the residue is dissolved in pure dioxane and the solvent is again evaporated. The procedure is repeated until pH of the solution was 7. The residue is washed with ice cooled $Et_2O$, which is discarded and compound 5 (18 mg, 100%) was obtained as a white solid.

Figure 3B:
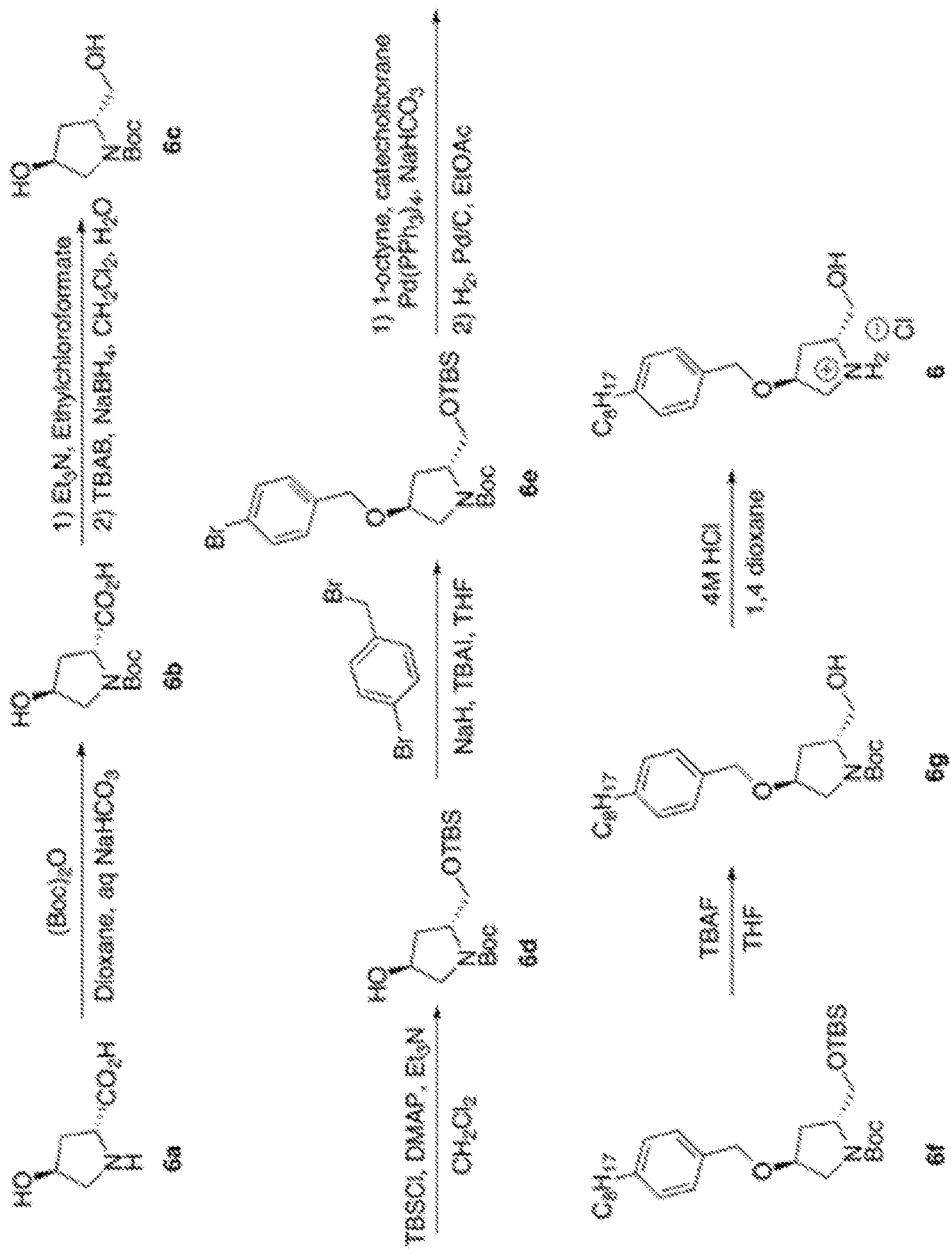

For compound 6, as illustrated in FIG. 3b, synthesis reactions track the reactions for compound 6. As for compound 5, precursors are available for compound 6c, 6c, and 6d. To synthesize compound 6e ((2R,4S)-1-Boc-4-((4-bromobenzyl)oxy)-2-(tert-butyldimethylsilyloxymethyl)-4-hydroxypyrrolidine), follow the procedure detailed by Zhang et al. (Zhang, S. et al., *Tetrahedron Lett.* 2009, 50, 1173-1176, the disclosure of which is incorporated herein by reference.) Next, in a two-step reaction, a solution of 1 . . . octyne (3.1 mL, 21.0 mmol) and catecholborane (1.0 M in THF, 21.0 mL, 21.0 mmol) is refluxed at 70° C. for 2 hours under Argon atmosphere. The reaction mixture is allowed to cool down to room temperature. A solution of 6e (3.5 g, 7.0 mmol) in DME (80.0 mL) is added to the reaction mixture followed by $Pd(PPh_3)_4$ (243.0 mg, 0.21 mmol) and 1N aqueous solution of $NaHCO_3$ (60 mL). The reaction mixture is refluxed with vigorous stirring overnight. The mixture was cooled down to room temperature and a brine solution was added. The mixture is extracted three times with $Et_2O$ and the combined organic layers were dried over $Na_2SO_4$ and filtrated. The solvent is removed under reduced pressure and the residue is purified by flash chromatography (hexane: EtOAc, 12:1 to 9:1) to give a slight yellow oil. This oil is then dissolved in EtOAc (140 mL) and Pd/C (10%, 745.0 mg, 0.7 mmol) was added. The air is pumped out of the flask and replaced by $H_2$. Upon completion as indicated by TLC, the reaction is stopped and the reaction mixture is filtered through cotton and Celite. The solvent is removed under reduced pressure to give hydrogenation product 6f (3.25 g, 87% over two steps) as a slight yellow oil. Next, to remove TBS from compound 6f, it is reacted with TBAF and THF, yielding 6g, obtained as a slight yellow oil. Finally, compound 6g (1.0 g, 2.4 mmol) is dissolved in a 4.0 M HCl solution in dioxane (60.0 mL, 240 mmol) and the mixture is stirred in room temperature overnight. MS and TLC analysis shows only the desired compound. The solvent is evaporated and the residue is dissolved in pure dioxane and the solvent was evaporated again. The procedure is repeated until the pH of the solution was 7. The residue is purified by flash chromatography (EtOH: $CH_2Cl_2$, 1:9 to 1:4) to give compound 6 (759 mg, 90%) as a white solid.

Figure 3C:
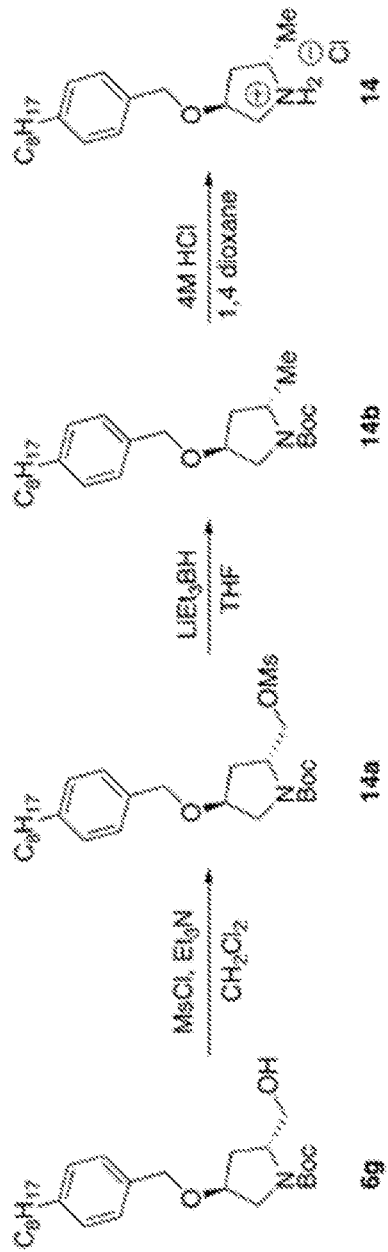

For compounds 14 and 15, compound 6g ((2R,4S)-1-Boc-4-((4-octenylbenzyl)oxy) prolinol) was used as a precursor. As illustrated in FIG. 3c, synthesis of compound 14 involves three steps. First, compound 6g (100 mg, 0.238 mmol) is dissolved in $CH_2Cl_2$ (0.8 mL) and $Et_3N$ (66 µL, 0.476 mmol) is added. Then, the solution is cooled to 0° C. before MsCl (28 µL, 0.357 mmol) is added and the solution is run over night. The reaction mixture is poured into water and extracted with EtOAc. The combined organic phases are dried over $MgSO_4$, filtered and concentrated under reduced pressure. The residue is purified by flash chromatography (hexane: EtOAc, 3:1) to give compound 14a (112 mg, 95%) as a slight yellow oil. Second, to synthesize compound 14b, $LiBHEt_3$ (1 M solution in THF, 0.644 mL, 0.644 mmol) is slowly added to an ice-cold solution of compound 14a (80 mg, 0.161 mmol) in THF (0.16 mL). The solution warms to room temperature. After 2 hours of stirring, no more starting material should be visible on TLC. The reaction is then quenched with water and poured into EtOAc. The water phase and the EtOAc phase are separated and the water phase was extracted with EtOAc. The combined organic phases were washed with brine, dried over $MgSO_4$, filtered and concentrated under reduced pressure. The residue is purified by flash chromatography (hexane: EtOAc, 16:1) to give compound 14b (60 mg, 92%) as a slight yellow oil. Third, and finally, to complete synthesis of compound 14, compound 14b (28 mg, 0.069 mmol) is dissolved in 4 M HCl in dioxane (1.73 mL, 6.9 mmol) and stirred overnight. TLC analysis of the crude mixture should show only the desired compound. The solvent is evaporated and the residue dissolved in pure dioxane and evaporated again. The residue is purified by flash chromatography (EtOH:$CH_2CH_2$, 1:10) to give 14b (20.1 mg, 85%) as a white solid.

Compound 15 is synthesized in a single 2-step reaction where compound 6g is the chemical precursor. To synthesize compound 15 ((2R,4S)-2-(methoxymethyl)-4-((4-octylbenzyl)oxy)-pyrrolidine hydrochloride salt), compound 6g (50 mg, 0.12 mmol) is dissolved in dry THF (1 mL), purged with Argon and cooled to 0° C. before NaH (60% in mineral oil, 9.6 mg, 0.24 mmol) is added. To this reaction mixture, MeI (15 µL, 0.24 mmol) is added and the reaction is allowed to warm to room temperature and run over night. Afterwards, the reaction is quenched with saturated solution of $NH_4Cl$, diluted with EtOAc and the two phases are separated. The water phase is extracted twice with EtOAc and the combined organic phases are dried over $MgSO_4$, filtrate. The solvent is then removed under reduced pressure and the residue is purified by flash chromatography (hexane: EtOAc, 9:1) to give the methylated alcohol (36 mg, 69%) as a colorless oil. The methylated alcohol (35 mg, 0.08 mmol) is then dissolved in 4 M HCl in dioxane (2.4 mL) and stirred overnight. TLC analysis of the crude mixture shows only the desired compound. The solvent was evaporated and the residue was dissolved in pure dioxane and the solvent was evaporated again. The residue was purified by flash chromatography (EtOH:$CH_2CH_2$, 1:9) to give 15 (26 mg, 88%) as a slightly yellow solid.

Figure 3D:
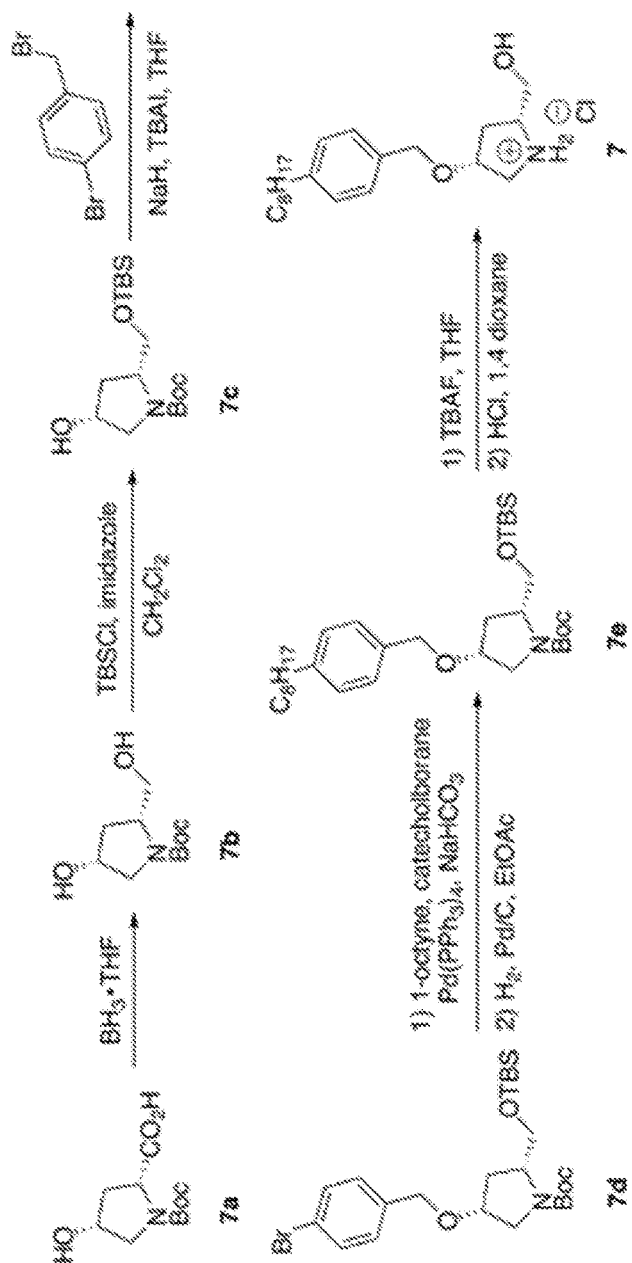

As illustrated in FIG. 3d, synthesis of compound 7 requires several steps, many of which can be eliminated by using known molecular precursors. In particular, synthesis can occur using compound 7b or compound 7c as precursors. Both are known compounds and spectral data are in agreement with the proposed structures and matched those reported in the literature. (See Watanabe, A et al., *J. Heterocyclic Chem.* 2011, 48, 1132-1139, the disclosure of which is incorporated herein by reference.) Starting with compound 7c, compound 7d is obtained as a colorless oil. Next, compound 7e is obtained over two steps (enumerated in FIG. 3d) from compound 7d. Finally, compound 7 was obtained as a yellow solid/oil from compound 7e.

Figure 3E:
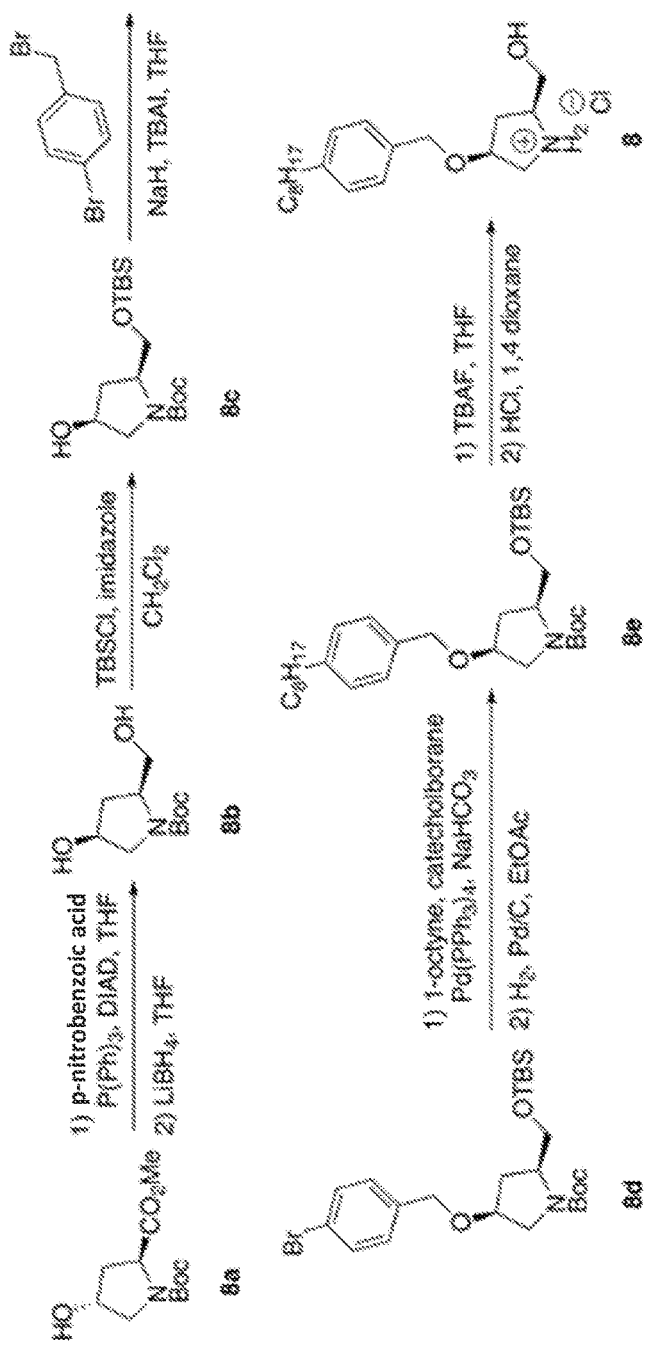

As illustrated in FIG. 3e compound 8 can be synthesized according to the procedure for synthesizing compounds 5 and 7. Compounds 8b and 8c are known compounds and special data were in agreement with the proposed structures and matched those reported in the literature. (See Watanabe, J. Heterocyclic Chem. 2011, 48, 1132-1139., the disclosure of which is incorporated herein by reference.) Compound 8d was obtained as a colorless oil from 8c. Compound 8e was obtained as a colorless oil from 8d. Compound 8 is a salt, obtained as a yellow oil over two steps from 8e.

Synthesis of compounds 9-12 (2,3-substituted pyrrolidine analogs) is discussed below. Compounds 10, 11, and 12 are derived from compound 9 ((2R,3S)-2-(hydroxymethyl)-3-((4-octylbenzyl)oxy)-pyrrolidine hydrochloride salt).

Figure 3F:
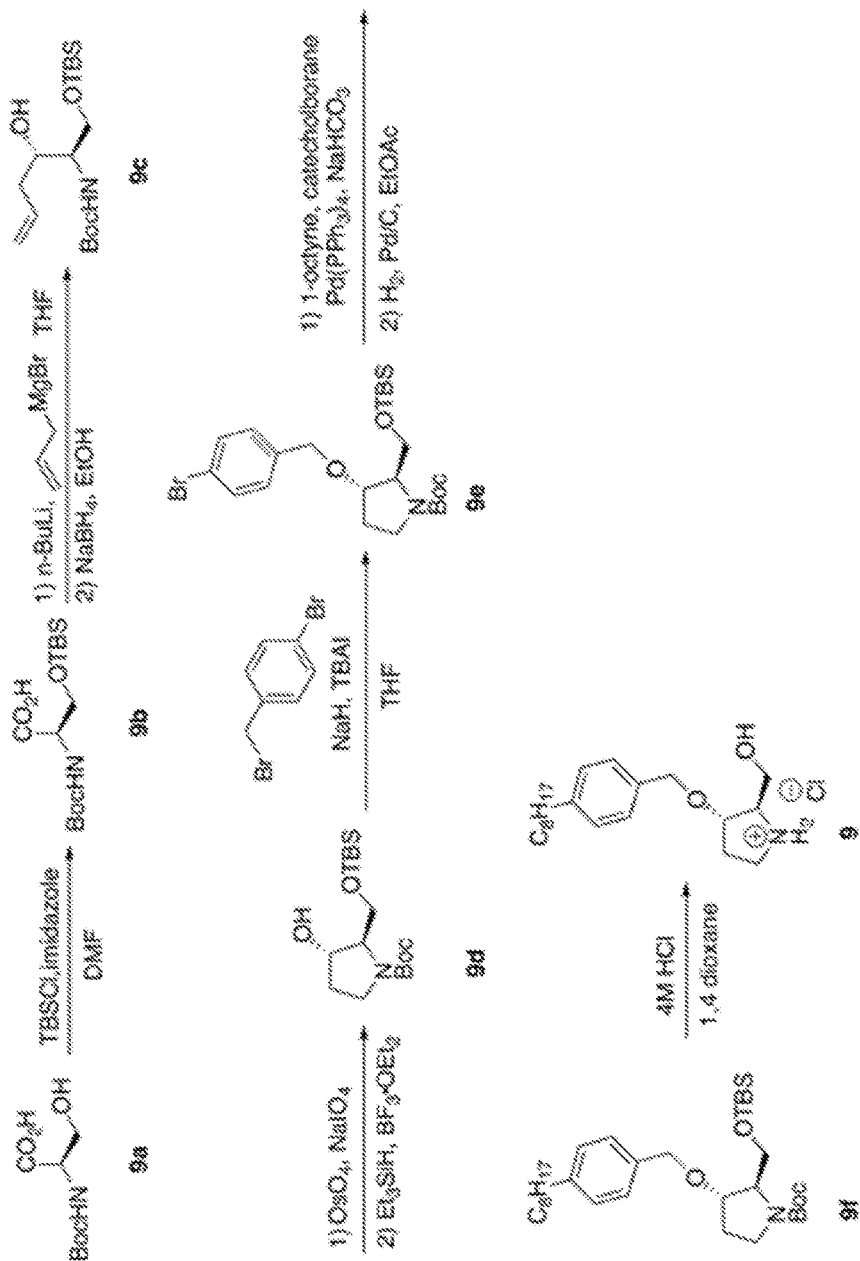

As illustrated in FIG. 3f, synthesis of compound 9 involves several intermediate reactions. Precursors to compound 9 (including compound 9d) are produced according to the procedure described by Evano et al. (See Toumi, M., et al., Angew. Chem. Int. Ed. 2007, 46, 572-575, the disclosure of which is incorporated herein by reference). Compound 9e is obtained as a slight yellow oil from compound 9d. Next, compound 9f was obtained as a slight yellow oil from compound 9e. Compound 9 is obtained as a yellow solid from compound 9f.

Figure 3G:
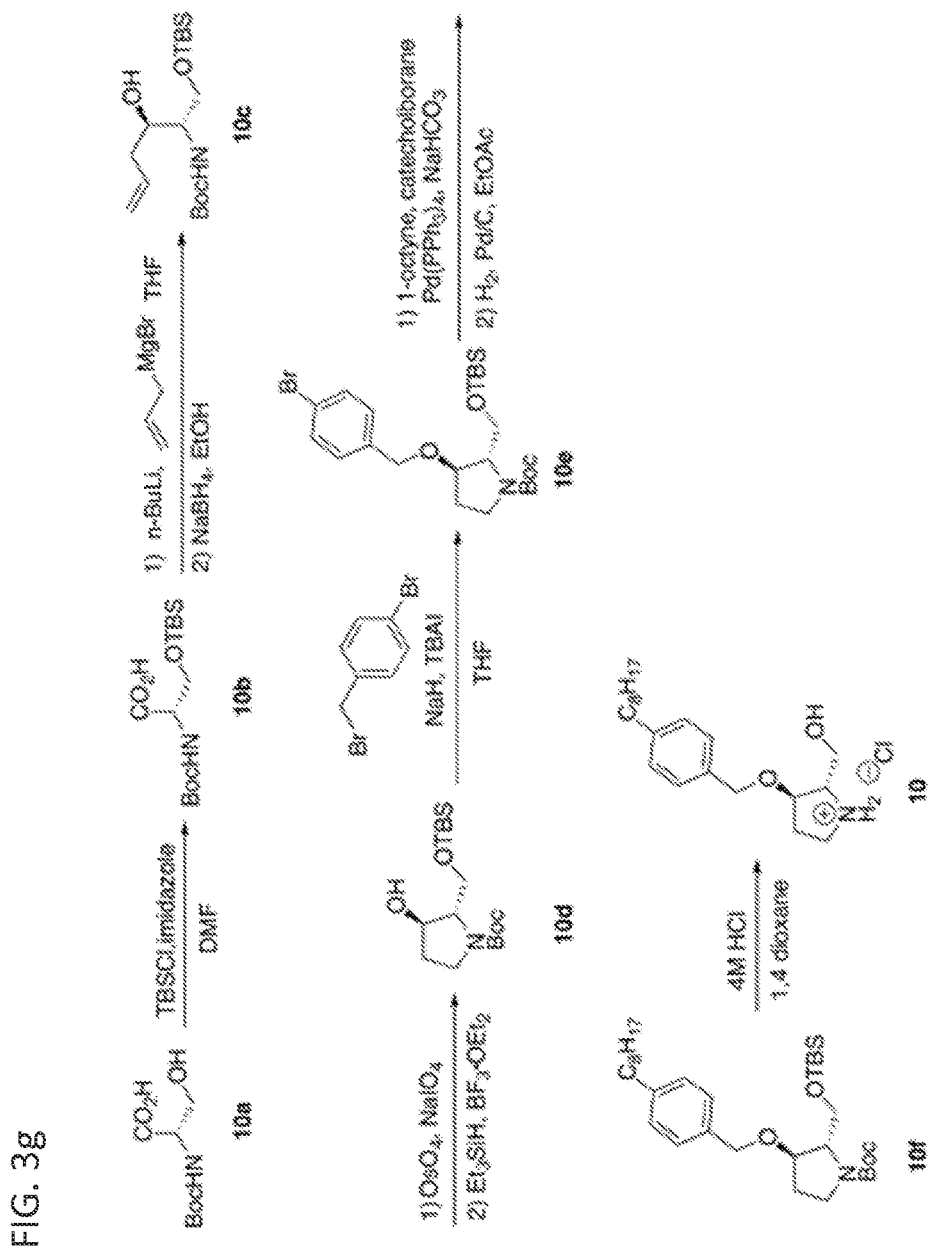

As illustrated in FIG. 3g, to synthesize compound 10, the process is almost identical to that in compound 9, albeit with a precursor of a different stereochemical conformation.

Figure 3H:
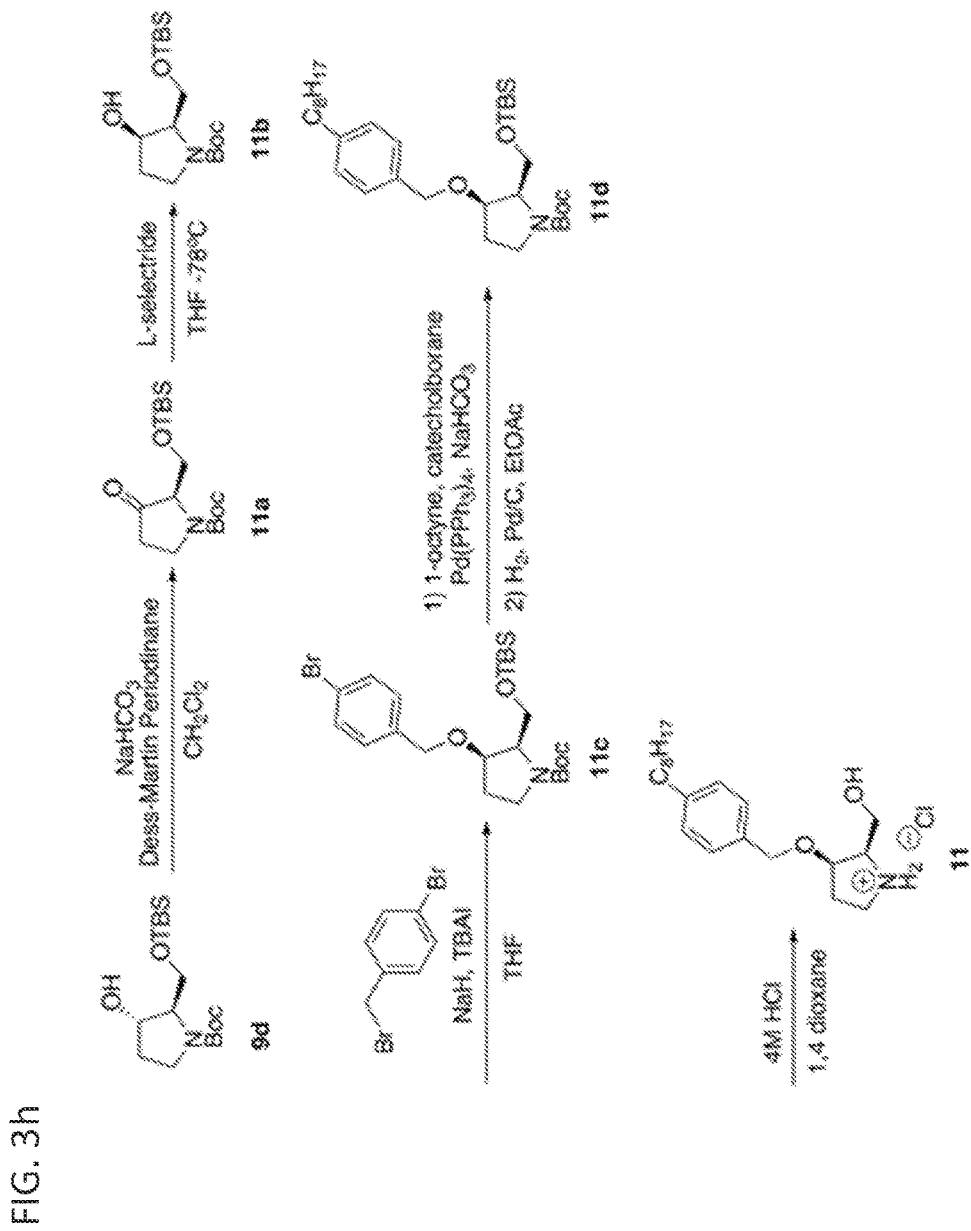

As is illustrated in FIG. 3h, synthesis of compound 11 is a several step process. It implicates compound 9d, as produced by the Evano et al. process discussed above. As illustrated in FIG. 3h, to synthesize 11a, NaHCO$_3$ (134 mg, 1.60 mmol) is added to a CH$_2$Cl$_2$ (1.0 mL) of compound 9d (70 mg, 0.21 mmol) at room temperature, followed by addition of Dess-Martin periodinane (134 mg, 0.32 mmol). The resulting mixture is stirred for 1.5 h, until no more starting material is observed by TLC. A saturated solution of Na$_2$S$_2$O$_3$ is then added to the mixture, the organic layer is separated and the aqueous layer is extracted with CH$_2$Cl$_2$. The combined organic layers are washed with brine, dried over MgSO$_4$, filtered and concentrated under reduced pressure. The residue is purified by flash chromatography (hexane: EtOAc, 12:1 to 8:1) to give compound 11a (64 mg, 92%) as a slight yellow oil. Next, compound 11 is synthesized by adding L-selectride (1 M in THF, 0.27 mL, 0.27 mmol) to THF (1.8 mL) of compound 11a (60 mg, 0.18 mmol) at 78° C. The resulting solution is stirred for 1 h at this temperature, no more starting material was observed by TLC. A saturated solution of NH$_4$Cl is then added to the solution, the organic layer is separated and the aqueous layer extracted with EtOAc. The combined organic layers are washed with brine, dried over MgSO$_4$, filtered and concentrated under reduced pressure. The residue is purified by flash chromatography (hexane: EtOAc, 5:1) to give compound 11 b (45 mg, 75%) as a colorless oil. Compound 11c was obtained as a colorless oil from compound 11 b. Compound 11d was obtained as a slight yellow oil over two steps from 11c. Compound 11 was obtained as a yellow solid from compound 11d.

Figure 3I:
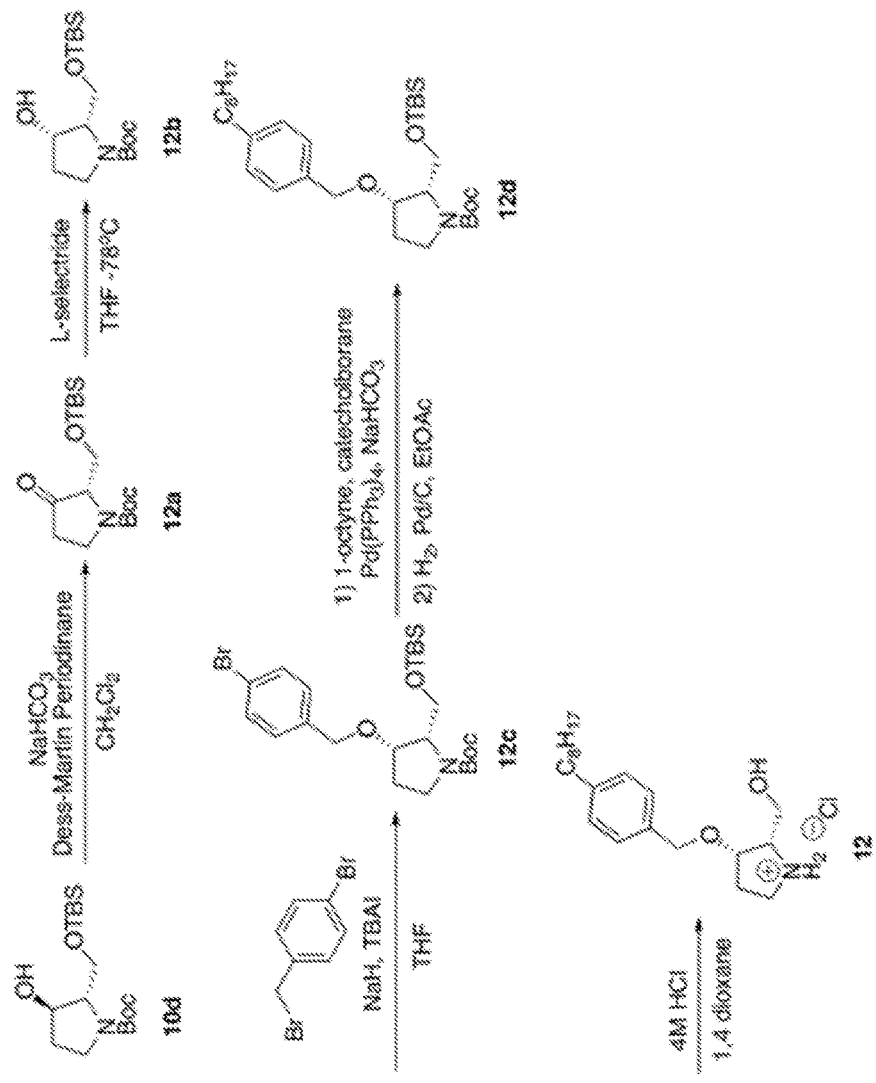

As is illustrated in FIG. 3i, synthesis of compound 12 is mostly the same as for compound 11. The only difference is that the process uses initially compound 10d, instead of 9d. Compound 10d is a stereoisomer of compound 9d.

Figure 3J:
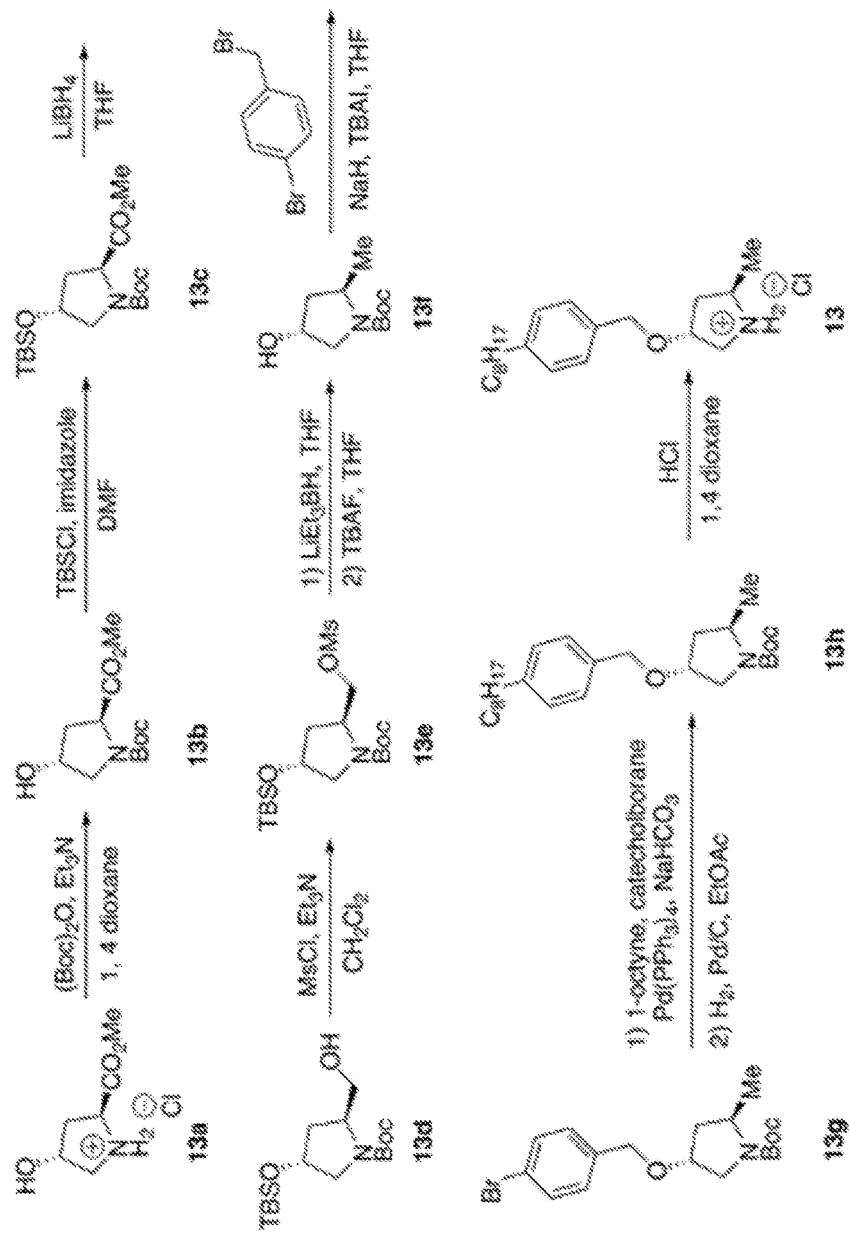

As illustrated in FIG. 3j, synthesis of compound 13 is a multistep process. For compound 13, several precursors can be used. Known precursors include compounds 13b-f. For these, compounds and spectral data is in agreement with the proposed structures and matches those reported in the literature. (See Gauchot, V. et al., J. Org. Chem. 2012, 77, 4917-4923; Watts, J. et al., Adv. Synth. Catal. 2012, 354, 1035-1042; Rosen, T et al., J. Med. Chem. 1988, 31, 1598-1611; Mitsumori, S. et al., J. Am. Chem. Soc. 2006, 128, 1040-1041, the disclosure of which is incorporated herein by reference.) Starting with compound 13f, compound 13g is obtained as a colorless oil. Next, compound 13h is obtained as a colorless oil over two steps from 13g. Finally, compound 13 is synthesized by dissolving compound 13h (100 mg, 0.25 mmol) in 4 M HCl in dioxane (6 mL) and stirring overnight. TLC analysis of the crude mixture should show only the desired compound. The solvent is evaporated and the residue is dissolved in pure dioxane and the solvent evaporated again. The residue was purified by flash chromatography (EtOH:DCM, 1:9) to give compound 13 (62 mg, 73%) as a slightly yellow solid.

Compounds 16 and 17, both 3-substituted pyrrolidine ethers, are synthesized using a similar sequence of reactions. Synthesis of compound 17 requires a precursor from compound 16.

Figure 3K:
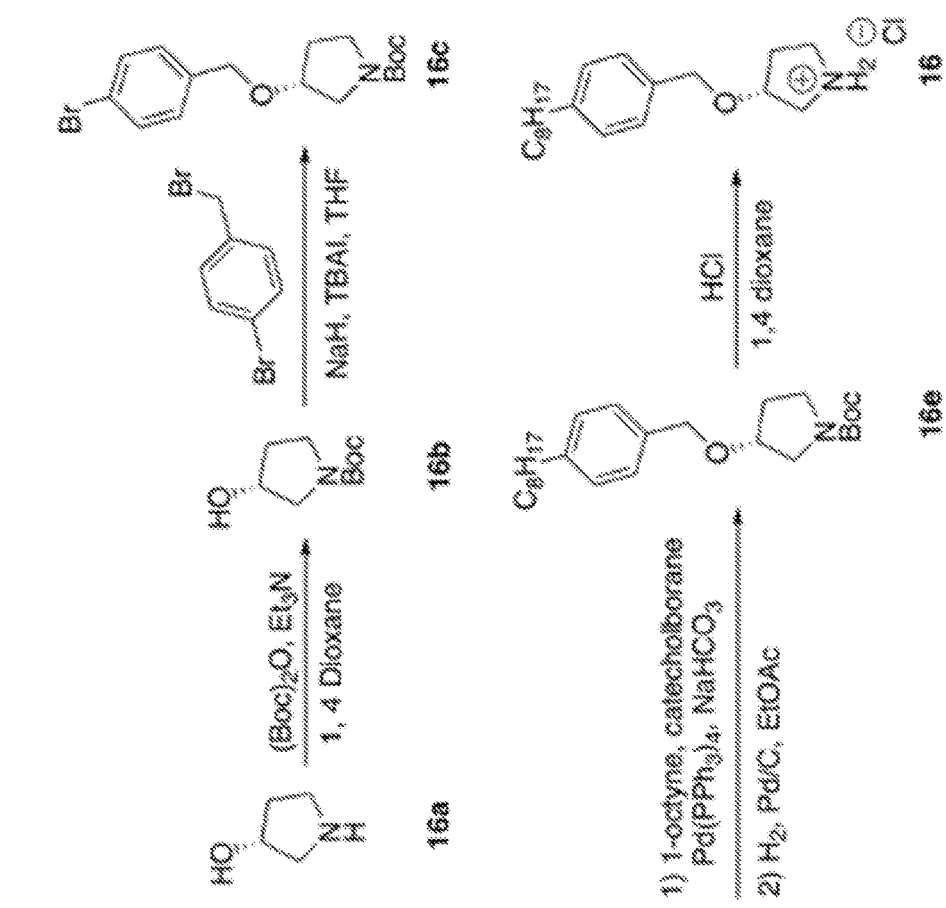
Figure 31:
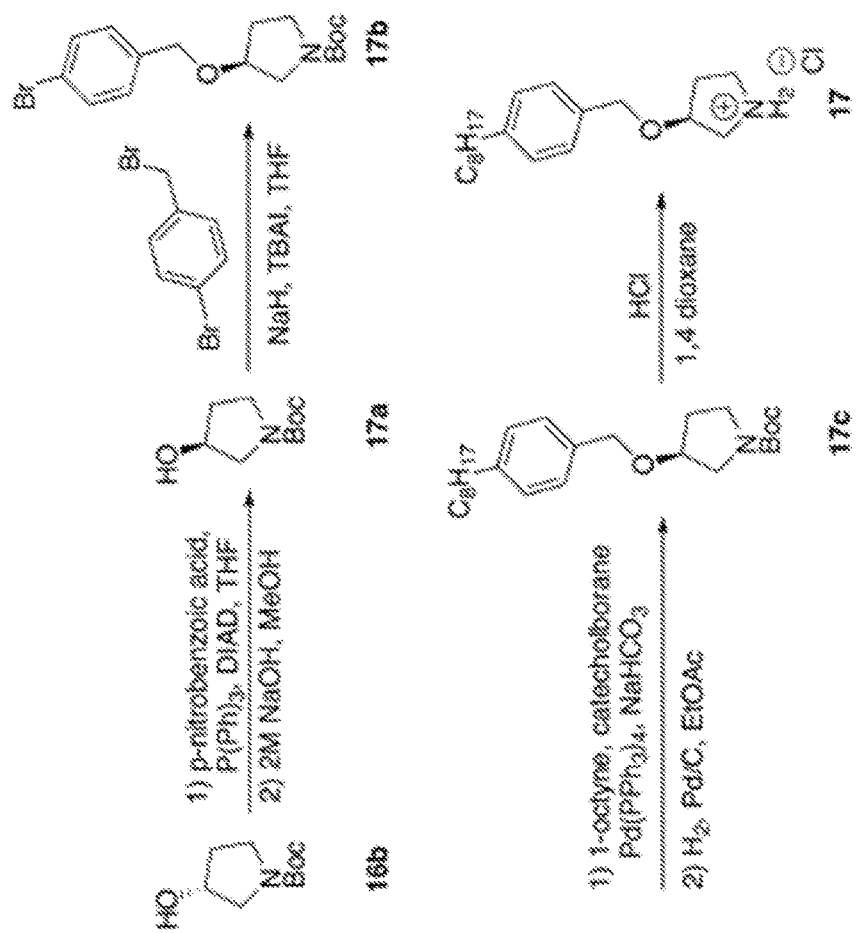

As is seen in FIG. 3k, synthesis of compound 16 is a four reaction process. First, compound 16b was obtained as a colorless oil (1.3 g, 100%) from (R)-3-Pyrrolidinol (539 mg, 6.19 mmol). Spectral data were in agreement with the proposed structures and matched those reported in the literature. (See Kucznierz, R. et. al., J. Med. Chem. 1998, 41, 4983-4994.) Compound 16c was obtained as a colorless oil from compound 16b. Compound 16e was obtained as a colorless oil over two steps from compound 16c. Finally, compound 16 was obtained as a yellow oil from compound 16e.

FIG. 3l demonstrates that synthesis of compound 17 uses compound 16b as a precursor and overall, the synthesis process is similar to that of compound 16. First, compound 17a is synthesized by dissolving compound 16b (400 mg, 2.14 mmol) in THF (8 mL). PPh3 (1.18 g, 4.49 mmol) and 4-nitrobenzoic acid (750 mg, 4.49 mmol) are sequentially added. The solution is cooled to 0° C. before DIAD (0.88 mL, 4.49 mmol) is added. The reaction is stirred at room temperature overnight. TLC should show no more starting material and the reaction mixture is diluted with EtOAc and washed with water and saturated solution of NaHCO$_3$. The organic layer is dried (MgSO$_4$) and evaporated. The residue is purified by flash chromatography (EtOAc:hexane, 2:8) to give the ester as a slightly yellow oil. The ester is then dissolved in MeOH (3.5 mL) and 2M NaOH (1.2 mL) is added. The reaction mixture is stirred in room temperature for 1 h. After completion, as indicated by TLC, the reaction mixture is diluted with EtOAc and the organic layer is washed with water, dried over MgSO$_4$, filtered and concentrated under reduced pressure. The residue is purified by flash chromatography (EtOAc:hexane, 1:1) to give compound 17a (113 mg, 47% over two steps) as a colorless oil. Spectral data are in agreement with the proposed structures and matched those reported in the literature. (See Kim, Y. J. et al., Bioorg. Med. Chem. Lett. 2000, 10, 2417-2420, the disclosure of which is incorporated herein by reference.)

Leukemia cell assays: Effects of chemical changes on ability to kill cells as observed in cell viability assays using the BCR-ABL positive human acute lymphoblastic leukemia (ALL) cell line, Sup-B15 are described. Assays using the Sup-B15 cell line were designed to determine efficacy of azacyclic constrained small molecule analogs of FTY720 in killing leukemia cells. Analogs were generated using the synthesis methods mentioned above. Sup-B15 cells were maintained at 2-3 million/mL in RPMI 1640 (by Mediatech™) supplemented with 10% fetal calf serum (by Sigma-Aldrich™), 10 mM Hepes (by Mediatech™), 55 µM β-mercaptoethanol (by Sigma-Aldrich™), 2 mM L-glutamine (by Mediatech™), and antibiotics. BV173, Nalm-6, and Blin-1 were maintained at 1-2 million/mL and CCRF-CEM at less than 500,000/mL in the same medium. BMp190 cells were created by transducing murine bone marrow cells with pMIC-p190 which expresses the p190 isoform of BCR-Abl and human CD4 from an IRES; these cells were kept at 1-2 million/mL in RPMI supplemented as above.

Flow cytometry: Much of the biological activity presented is shown through flow cytometry data. Flow cytometry data shows how many cells in culture were killed by FTY720 and analogs and levels of cell surface receptor expression. Here, $IC_{50}$ flow cytometry assays were used. In them, viability was determined at 72 hours by vital dye exclusion [propium iodide or DAPI (4',6-diamindino-2-phenylindole)]. To measure nutrient receptor expression following exposure to FTY720 and azacyclic constrained analogs of FTY720, surface 4F2hc expression was measured after 3 hours of drug treatment by staining 150,000 cells with phycoerythrin-conjugated mouse anti-human CD98 (by BD Biosciences™). Analysis was restricted to viable cells.

All samples for the disclosed sets of data were analyzed on a BD LSR II flow cytometer and data analyzed with FlowJo™ software (by Treestar™). $IC_{50}$'s were calculated and statistical tests were performed using GraphPad Prism™.

EXAMPLE 1

Stereochemistry

Figure 4A:
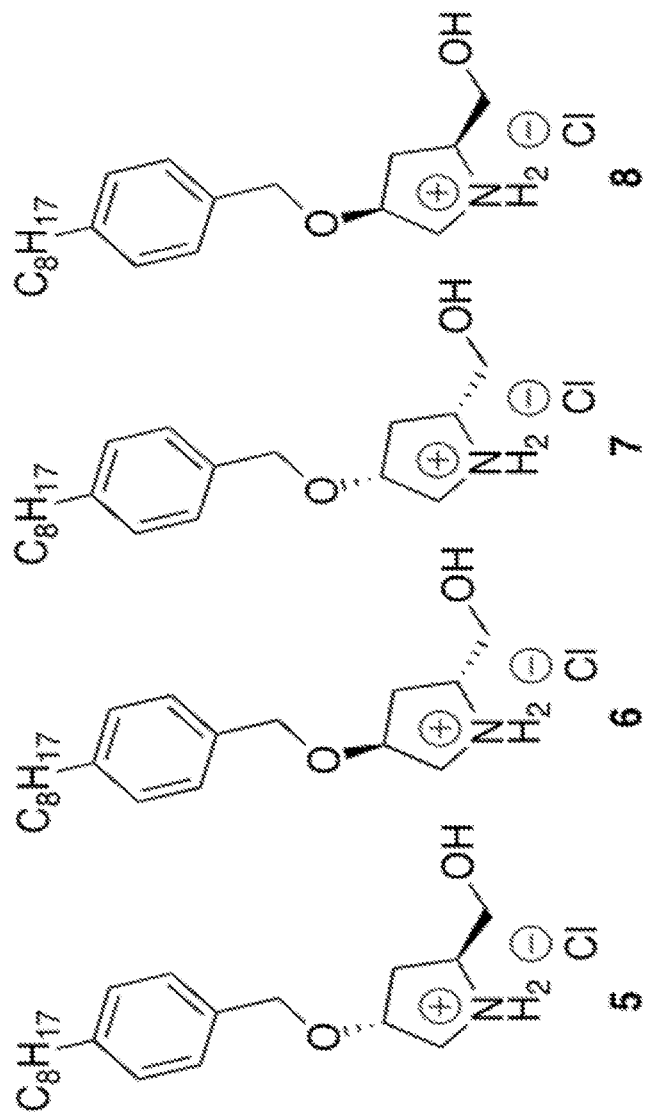
FIG. 4a provides molecular structures of therapeutic small molecule analogs in accordance with various embodiments of the invention.
Figure 4B:
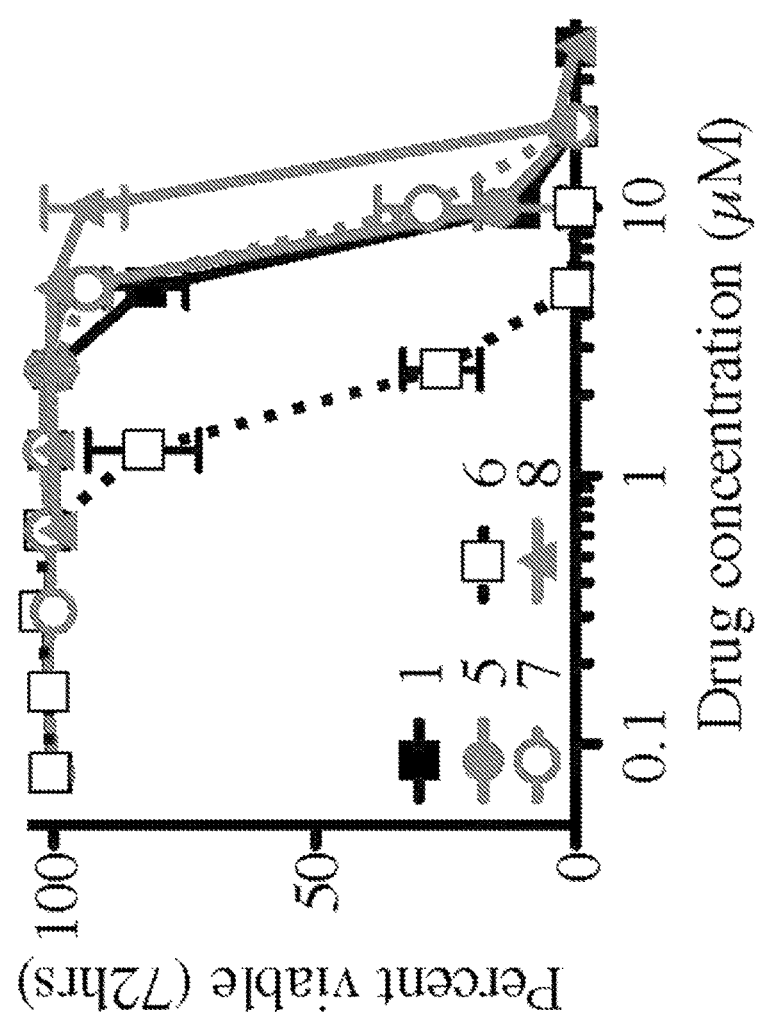
FIG. 4b provides data plots summarizing studies of the stereochemistry influence of ether relative to hydroxymethyl on the ability of embodiments of therapeutic small molecule analogs in accordance with the invention to kill leukemia cells.

In a first embodiment, cell culture assays were carried out to demonstrate the killing capabilities of different small molecule diastereomers in accordance with embodiments. In particular, compounds 5-8 (shown in FIG. 4a), provide members of a diastereomeric series, and the assays indicate that the three-dimensional orientation of the ether appendage relative to the hydroxymethyl group influence the ability of compounds to kill cancer cells. In fact, as is illustrated in FIG. 4b, even slight variations in the compound's stereochemistry can affect the potency of the small molecule analogs. In particular, certain compounds have greater killing ability than others. For example, compound 8 has an 8-fold decrease in activity relative to compound 6, and is 2-fold weaker than its enantiomer (compound 5). Indeed, compound 6 displayed activity much greater than compounds 5, 7, and 8, showing that stereochemistry can play a role in improving small molecule activity. Despite this potentially useful variability in activity, it should be noted that changes in the stereochemistry of the small molecule analog embodiments do not make the small molecule analog less effective than FTY720. In particular, all of the azacyclic constrained analogs are just as potent as the FTY720 control in killing leukemia cells. Additionally, these compounds confer the added benefit that the small molecules do not activate S1P1 or S1P3 receptors thereby avoiding the S1P receptor-related, dose-limiting toxicity associated with FTY720 and previously reported analogs (as will be described in greater detail with respect to FIGS. 10a and 10b, below). In sum, stereochemistry can either substantially increase the anti-leukemic activity of certain embodiments of the azacyclic constrained FTY720 analog, or it can play a trivial role that does not undermine the analogs overall ability to kill leukemia cells. Accordingly, modifying the stereochemistry of the analog embodiments has the potential to affect azacyclic constrained FTY720 analog efficacy, but with respect to some embodiments, and particularly SupB15 cells, does not decrease anti-cancer efficacy compared to conventional compounds.

EXAMPLE 2

O-Benzyl Chain Position

Figure 5A:
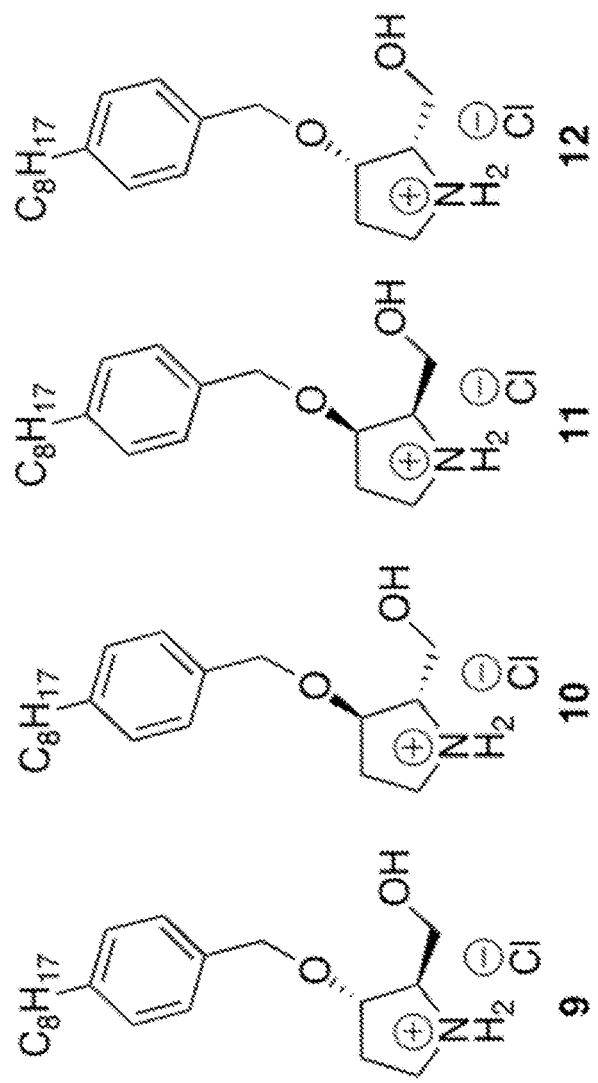
FIG. 5a provides molecular structures of therapeutic small molecule analogs in accordance with various embodiments of the invention.

In a second exemplary analysis, the position of the O-benzyl chain on the activity of the small molecule analogs was examined. In summary, this position is not shown to substantially affect the ability of embodiments to kill cells. Using the techniques discussed above, investigators synthesized diastereomeric 2-hydroxymethyl pyrrolidine 4-arylethers (FIG. 5a). These embodiments were synthesized using a precursor disclosed by Toumi, et al. (Toumi, M., et al., *Angew. Chem. Int. Ed.* 2007, 46, 572-575, the disclosure of which is incorporated herein by reference.) The procedure for obtaining compounds 10-12 is consistent with that for compound 9.

Figure 5B:
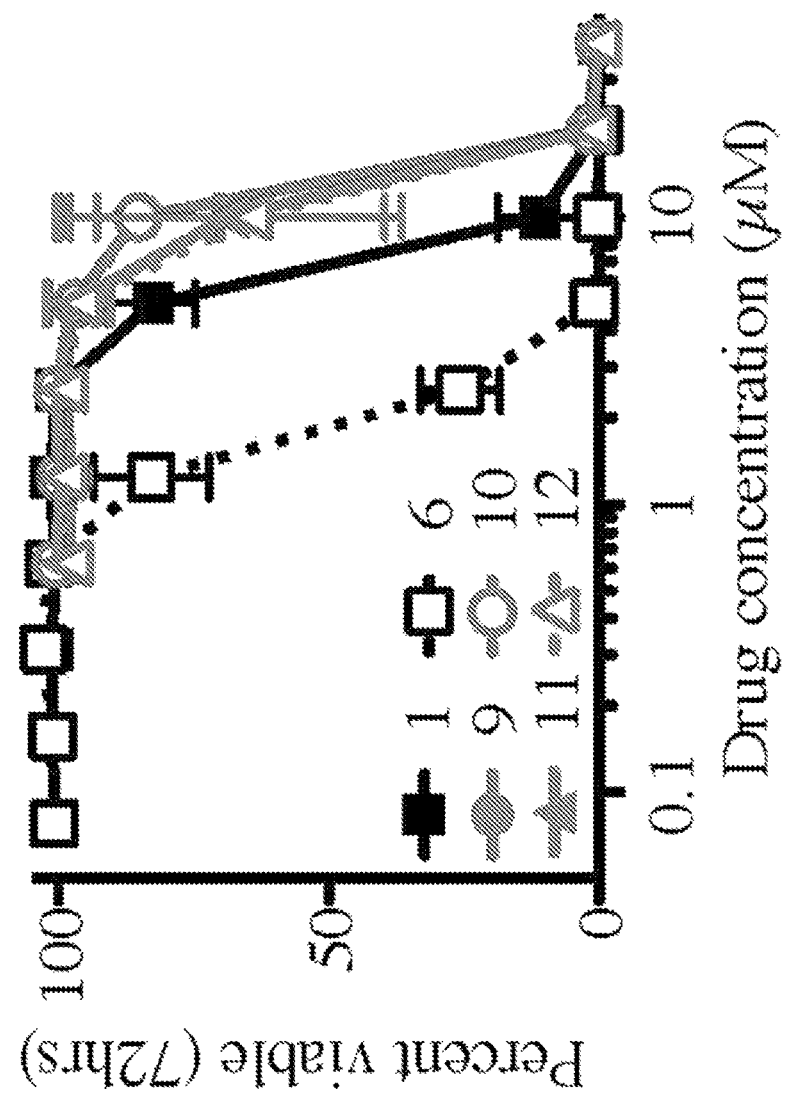
FIG. 5b provides data plots summarizing studies of the effect of pyrrolidine ring orientation on anticancer activity of embodiments of therapeutic small molecule analogs in accordance with the invention.

After synthesis of these analogs and their incorporation into Sup-B15 assays, it is shown that the position of the O-benzyl chain (position 3 versus position 4) does not completely undermine efficacy (comparing FIGS. 4b and 5b). In addition, both data plots show that molecules bearing O-benzyl at the 3 position present a therapeutic advantage over FTY720. Because these analogs have similar cancer-cell killing capabilities to the FTY720 control, yet do not trigger FTY720's S1P receptor-related, dose-limiting toxicity, they are therapeutically advantageous over the FTY720 control molecule. This increased efficacy with the ability to avoid S1P1/3 activation in animals shows that embodiments of this compound are viable therapeutic agents (see also the discussion, below, with respect to FIGS. 10a and 10b).

In addition, certain stereochemical conformations of the compound have unique therapeutic benefits. As shown in FIGS. 4b and 5b, compound 6 is unique in conferring enhanced anticancer activity relative to its diasteromeric congeners and to FTY720 in the particular leukemic cell line (Sup-B15) used in the study. This shows that, in addition to the therapeutic benefits of not activating S1P1/3, embodiments of azacyclic constrained analogs of FTY720 possess cancer-cell killing activity that is equal or superior to that of FTY720. In particular, as shown in the data plots, all of the embodiments trigger cell death with a similar potency to the more flexible parent FTY720. (In FIGS. 4b & 5b, FTY720 is plotted as compound 1.)

EXAMPLE 3

Phosphorylation

Figure 6A:
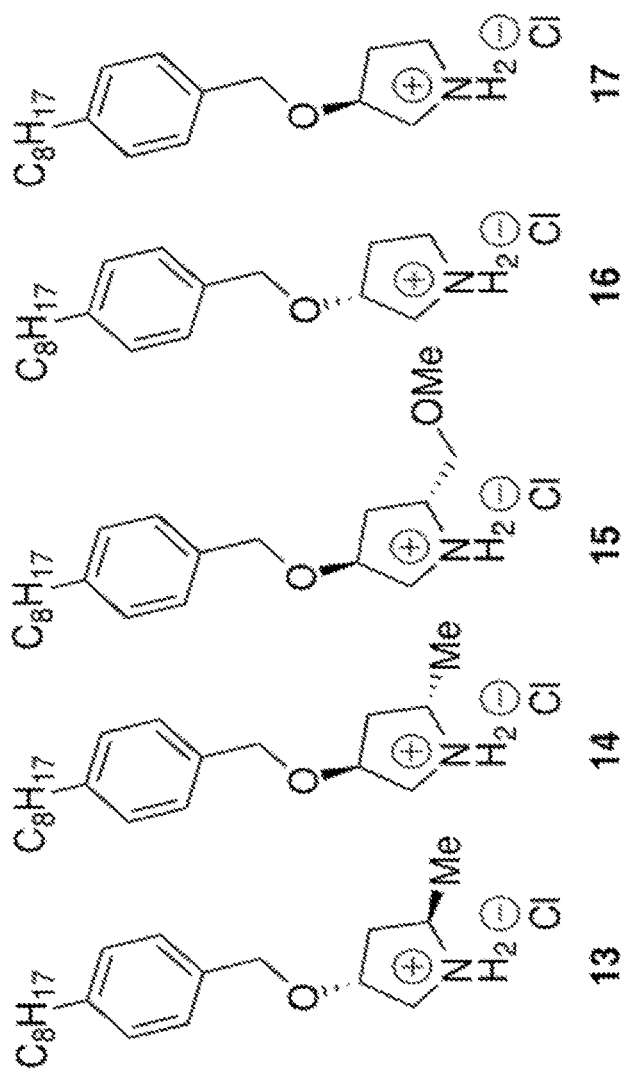
FIG. 6a provides molecular structures of therapeutic small molecule analogs in accordance with various embodiments of the invention.
Figure 6C:
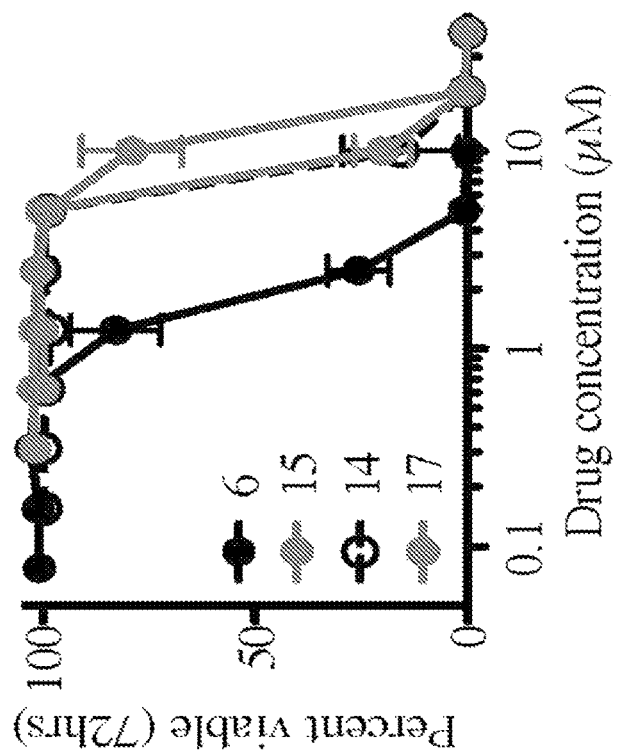
FIG. 6c provides data plots summarizing studies of the effect of the loss of phosphorylation sites on the hydroxymethyl group on the efficacy of embodiments of compound 6 therapeutic small molecule analogs in accordance with the invention.
Figure 6B:
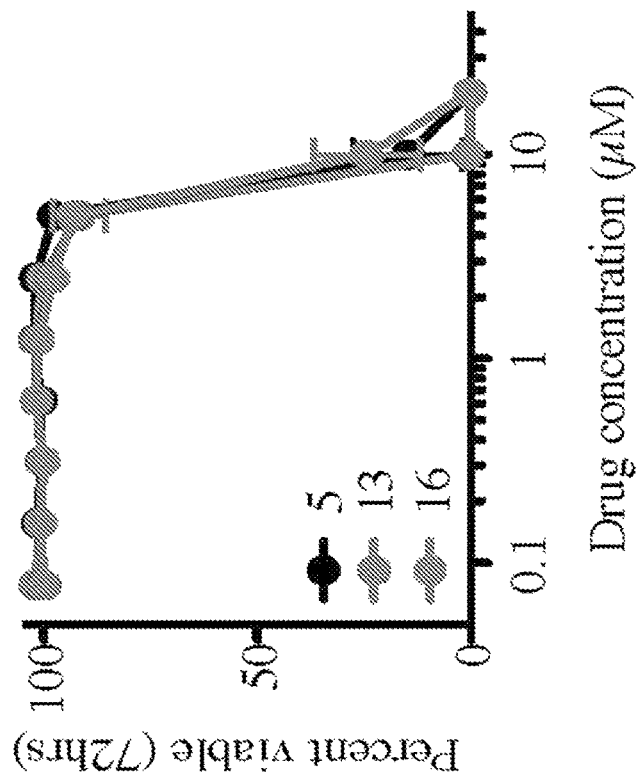
FIG. 6b provides data plots summarizing studies of the effect of the loss of phosphorylation sites on the hydroxymethyl group on the efficacy of embodiments of compound 5 therapeutic small molecule analogs in accordance with the invention.

In a third exemplary examination, loss of the phosphorylation site on the molecules is shown not to be important for the ability of FTY720 or its azacyclic constrained analogs to kill cancer cells. While the ability to interfere with S1P1 receptor signaling is critical for its immunosuppressive activity at low nanomolar doses, activation of S1P1 and S1P3 by FTY720 prevents it from being used in cancer therapy. Since the constrained analogs might also be subject to phosphorylation in the cells, a series of compounds in which the hydroxymethyl group was modified or entirely removed were studied. For example, in compounds 13 and 14, the hydroxymethyl group present in 5 and 6 respectively was replaced with a methyl group (FIG. 6a). Loss of this potential phosphorylation site had no detectable effect on the potency of 13 relative to 5 but decreased the activity of 14 relative to 6 (FIGS. 6b & 6c). Similarly, protecting the hydroxyl group as the O-methyl ether as in compound 15 reduced the potency of relative to 6. Removing the hydroxymethyl group from 5 to give the pyrrolidine 16 had only a marginal effect on activity in cell viability assays. However, the enantiomeric pyrrolidine analogue 17 exhibited a 6-fold reduction in activity relative to 6. As compounds 13-17 cannot be phosphorylated but retain the ability to kill leukemia cells, the results are consistent with a model where phosphorylation is not required for the ability of FTY720 to kill cancer cells.

In summary, the elimination of potential phosphorylation sites on compound 5 has no effect on its cancer-cell killing efficacy. For compound 6, removal of phosphorylation does have a greater effect on efficacy than for compound 5 (compare FIG. 6c to FIGS. 5b & 6b). This study demonstrates that phosphorylation may be relevant to a compound's ability to kill cancer cells when compared to the efficacy of FTY720, in some embodiments.

EXAMPLE 4

Characteristics of Aliphatic Chain

Figure 7A:
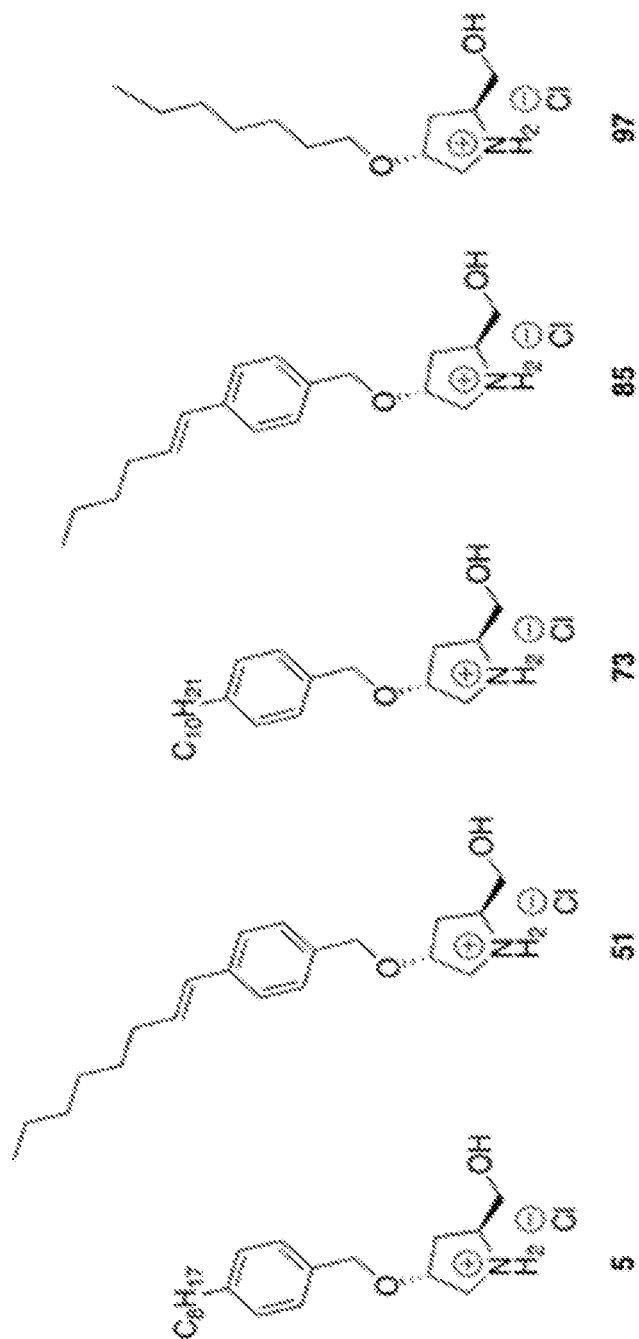
FIG. 7a provides molecular structures of therapeutic small molecule analogs in accordance with various embodiments of the invention.
Figure 7B:
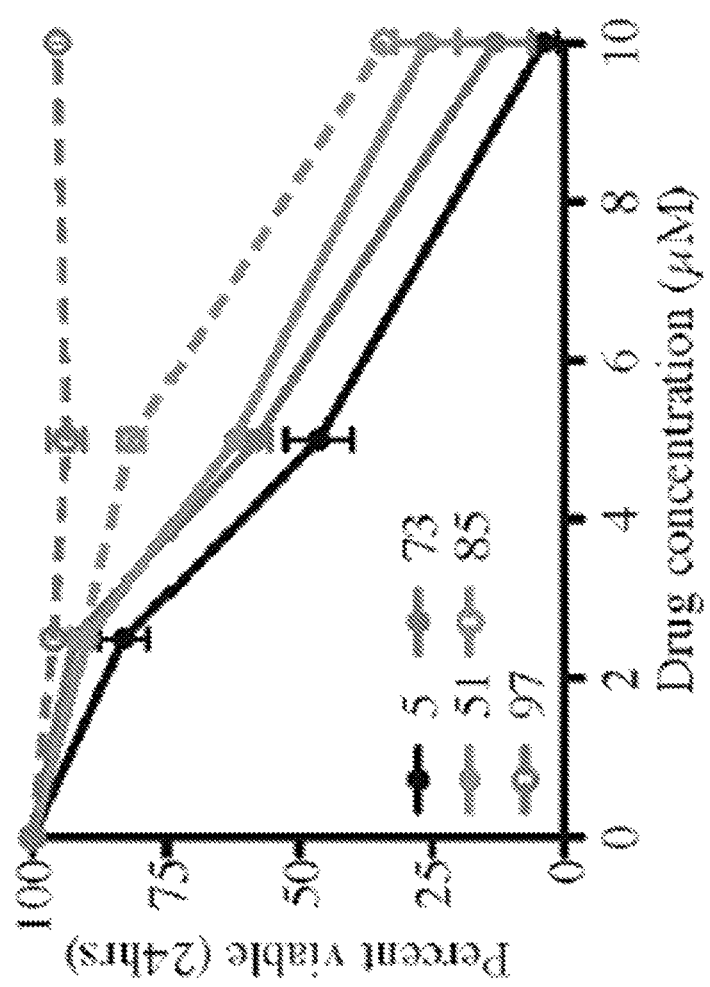
FIG. 7b provides data plots summarizing studies of the effect of the length of aliphatic chains on the efficacy of anticancer activity of embodiments of therapeutic small molecule analogs in accordance with the invention.

In a fourth exemplary study the effect on activity of the nature and length of the aliphatic chain on the phenyl was examined. As shown in FIGS. 7a and 7b, the nature and length of the aliphatic chain is critical to the activity of the analog embodiments. In particular, as shown in FIG. 7b, analogs of compound 5 with shorter and longer chains, or with a simple heptyl chain are less active, as are MOM ethers. This demonstrates the importance of constraining the claimed length of the aliphatic chain to between six and ten carbons in the analog embodiments.

EXAMPLE 5

Effects on Nutrient Transporter Expression

Figure 8:
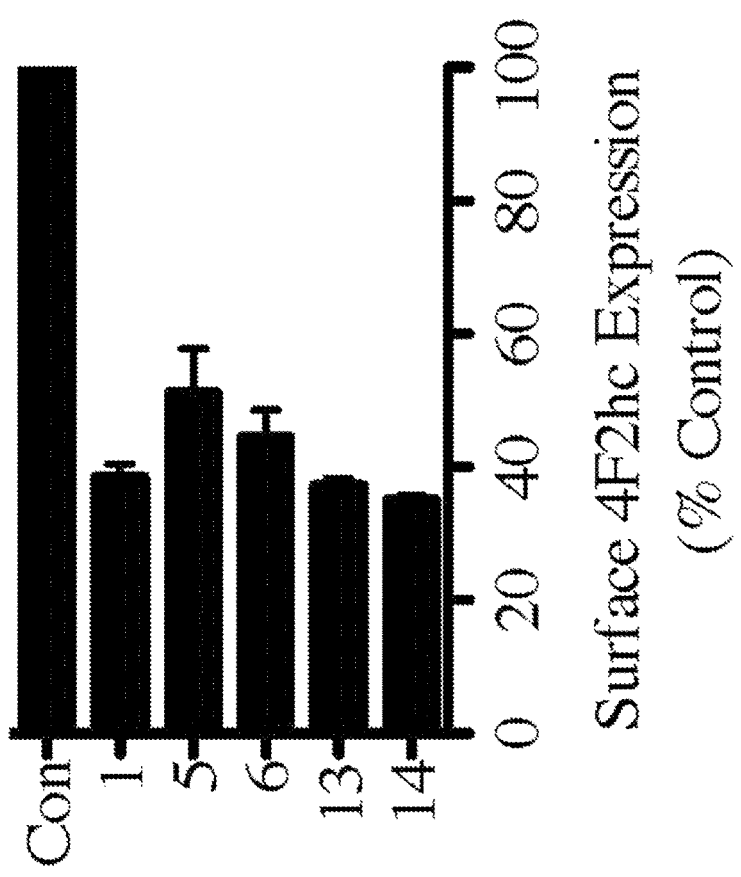
FIG. 8 provides data plots summarizing studies of the ability of embodiments of therapeutic small molecule analogs in accordance with the invention to trigger nutrient transporter loss in Sup-B15 leukemia cells.

In a fifth exemplary study the efficacy of the azacyclic constrained FTY720 analog embodiments at triggering the loss of nutrient transporters in cancer cells was examined. As shown in FIG. 8, the small molecule analogs described herein provoke a loss in nutrient transporter in cancer cells irrespective of stereochemical conformation or phosphorylation when used at 10 µM. Additionally, the compounds are shown to be at least as effective as the proven immunosuppressant FTY720. This shows that the described azacyclic constrained analogs of FTY720 will be effective as a therapeutic designed to inhibit nutrient transport in cancer cells while avoiding S1P receptor binding, thus providing a family of compounds capable of providing a therapeutically effective medicament without triggering the side-effects found with S1P active molecules such as FTY720 and its conventional analogs.

EXAMPLE 6

Cell Viability Assays

Having observed an increased potency of compound 6 relative to its diastereoisomers 5, 7 and 8, it was also necessary to determine whether this differential activity was also seen in other cancer cell lines. Cell viability assays were used to compare the activity of the constrained analogs and FTY720 in an additional BCR-ABL positive ALL cell line, BV173. As shown in Table 1, below, in this cell line, compound 6 was again more active than its stereoisomers 5, 7 and 8. Interestingly, compound 6 was also 10-fold more active than compound 5 in murine bone marrow transformed by introduction of the BCR-ABL fusion protein p190. Nalm-6, Blin-1, and CCRF-CEM are also ALL cell lines but do not express the oncogenic BCR-ABL fusion protein. In these three human leukemia cell lines, 6 no longer exhibited increased potency relative to other compounds in the series. The effect of compound 6 and its diastereoisomeric congeners on the prostate cancer cell lines PC3 and DU145 was also determined. Compounds 5 and 6 induced cell death to a similar extent, and the potency of the constrained analogs was slightly reduced relative to FTY720.

TABLE 1

Mean IC50 (in µM +/− SEM) of analogs in cell viability assays in a range of human cancer cell lines and BCR-Abl-expressing murine bone marrow (BM).

|   | SupB15 Ph+ ALL | BM- p190 | BV173 Ph+ ALL | CCRF- CEM Ph− ALL | Nalm-6 Ph− ALL | Blin-1 Ph− ALL | PC3 prostate | DU145 prostate |
|---|---|---|---|---|---|---|---|---|
| 1 | 6.8 ± 0.7 | 3.3 ± 0.2 | 6.3 ± 0.4 | 6.8 ± 0.3 | 9.6 ± 1.9 | 5.5 ± 0.1 | 9.8 ± 0.9 | 6.5 ± 0.9 |
| 5 | 7.7 ± 0.8 | 5.7 ± 1.1* | 10.4 ± 0.7*** | 11.0 ± 1.3*** | 15.0 ± 2.1 | 7.5 ± 0.1*** | 14.3 ± 1.2* | 10.8 ± 0.4* |
| 6 | 2.0 ± 0.2*** | 0.5 ± 0.1*** | 3.8 ± 0.4** | 8.2 ± 0.7 | 13.5 ± 2.4 | 6.9 ± 0.3** | 13.5 ± 2.6 | 15.1 ± 1.0** |
| 7 | 8.3 ± 0.8 | 4.0 ± 0.4 | 9.7 ± 1.0** | 8.1 ± 1.4 | | | | |
| 8 | 16.7 ± 2.4*** | 8.4 ± 1.5** | 13.8 ± 0.8*** | 11.6 ± 1.1*** | | | | |

Viability was measured by vital dye exclusion and flow cytometry at 72 h. When compared to FTY720 using a t test (two-tailed):
*p < 0.05;
**p < 0.01;
***p < 0.001.

From these findings, it is possible to conclude that the enhanced potency of 6 over its diastereoisomers is a characteristic associated with hematologic but not prostate cancers and may be linked to expression of the BCR-ABL fusion protein. BCR-ABL dependent signaling drives the survival and proliferation of chronic myelogenous leukemias and a subset of ALLs. Thus, embodiments of the analog compounds with activity against BCR-ABL positive leukemias could have particular clinical utility.

EXAMPLE 7

Characteristics of Compound 6

Figure 9B:
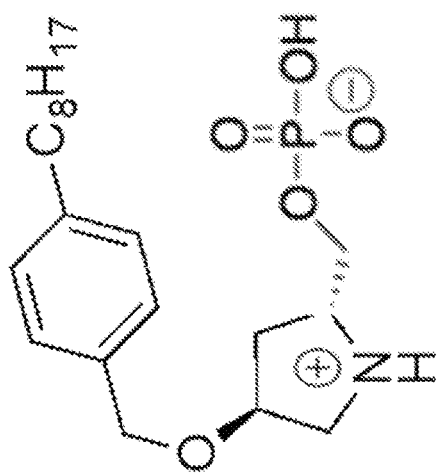
FIGS. 9a and 9b provide a molecular structure of compound 6 and its phosphate in accordance with the invention.
Figure 9A:
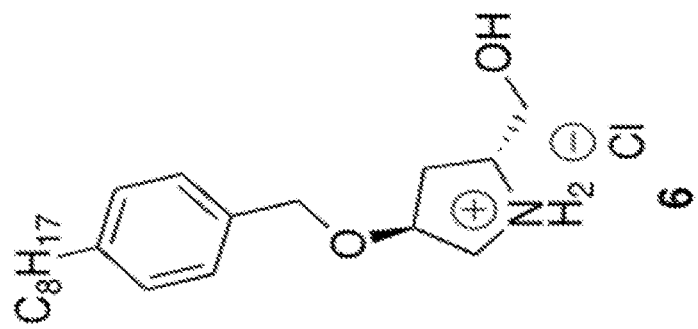
Figure 10A:
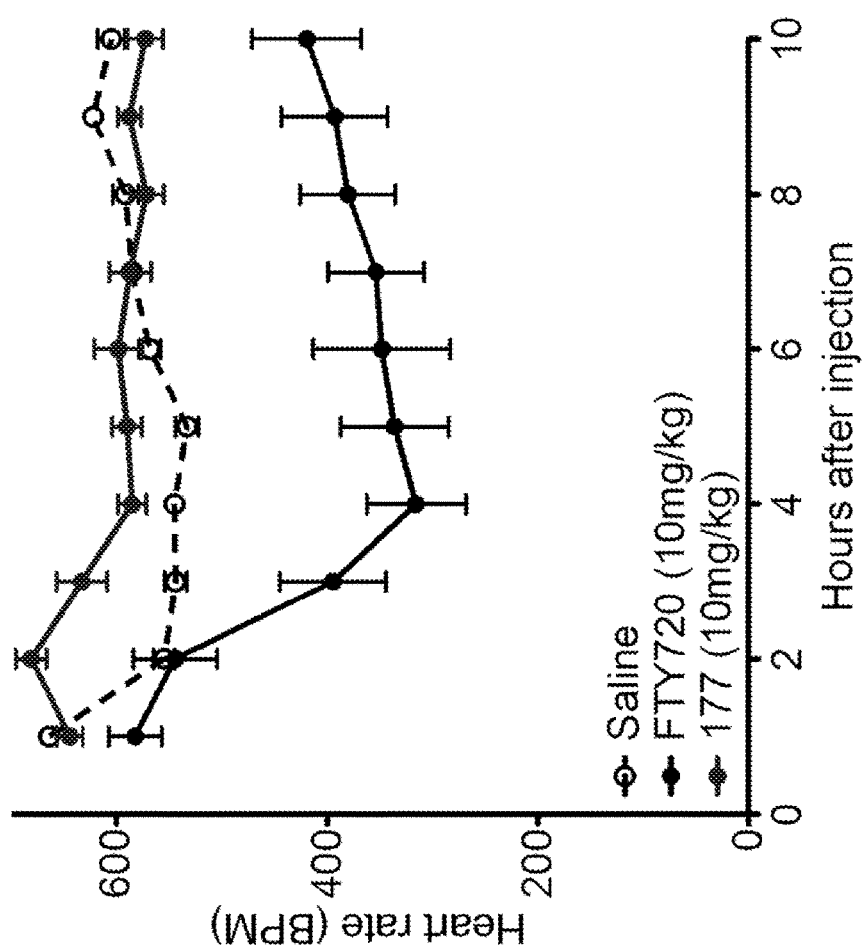
FIGS. 10a to 10o provide data plots providing the results of studies on the efficacy and activity of an exemplary therapeutic small molecule analog in accordance with the invention.
Figure 10B:
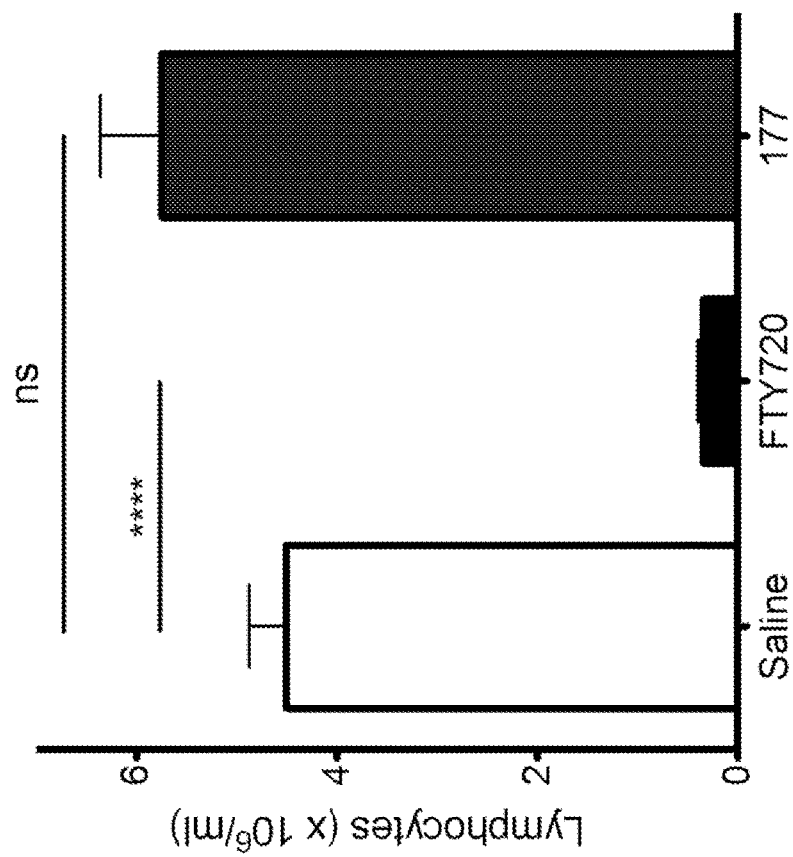
Figure 10C:
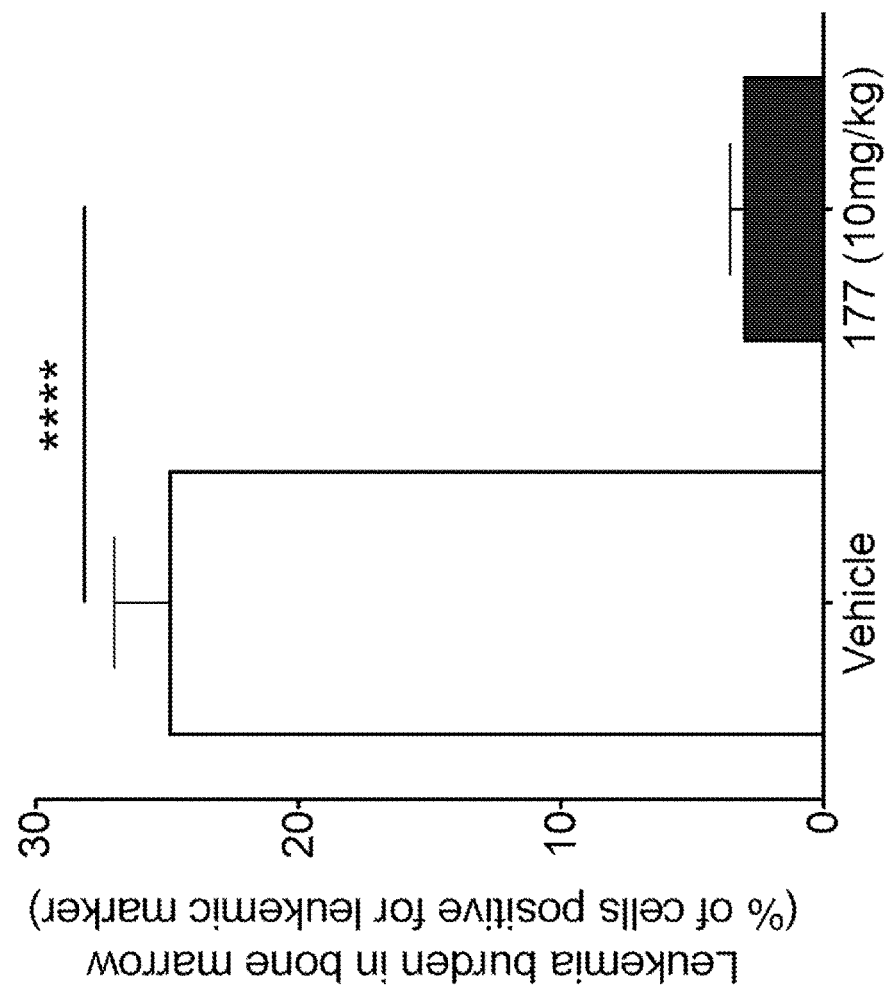
Figure 10D:
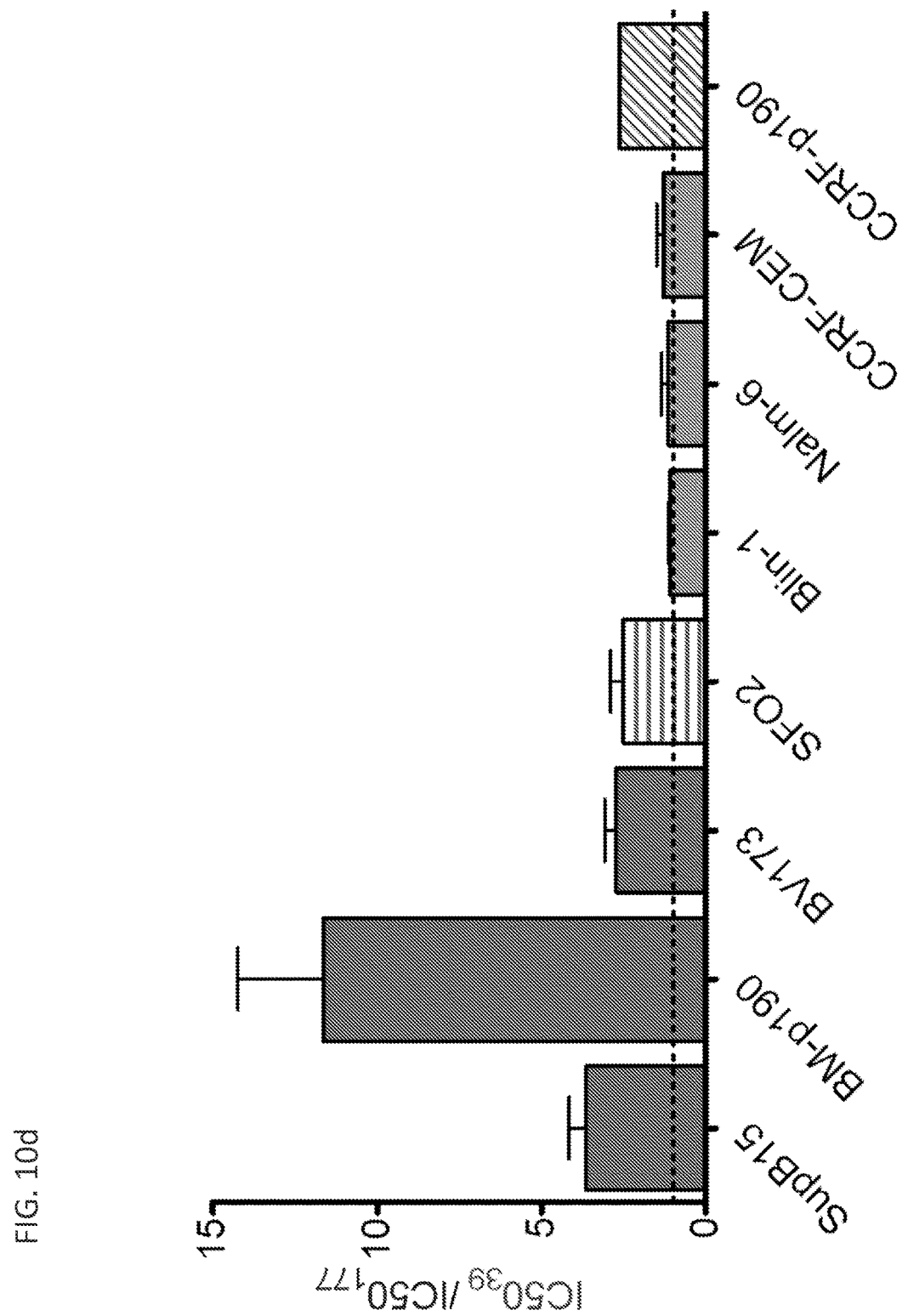

Based on its promising activity, an examination was undertaken of a compound 6 and its related phosphate. (The molecular formula for this compound and its phosphate are shown in FIGS. 9a and 9b.) A summary of the results are provided, below, along with a number of correlated data graphs (FIGS. 10a to 10o). (Note, in FIGS. 10a to 10o, compound 6 is labeled with the number "177", its phosphate is labeled with the number "1062", and its enantiomer is labeled "39".

As previously discussed, FTY720 itself cannot be used in cancer patients because phosphorylation of FTY720 by SphKs makes FTY720-P, which acts at S1P receptors to cause bradycardia and immunosuppression (on-target effect for primary use). As shown in FIG. 10a, telemetry was used to measure mouse heart rate for 24 h after administration of anti-cancer dose of FTY720 and a dramatic drop in heart rate is observed. In addition, as shown in FIG. 10b, FTY720 also causes lymphocyte sequestration, as measured by the number of circulating lymphocytes 12 h after dosage. However, compound 6, according to embodiments of the invention does not cause immunosuppression (FIG. 10b), nor does it decrease heart rate at the same doses. (Note, both single doses of 10 mg/kg and multiple doses at 30 mg/kg of compound 6 and its phosphate were administered in this study with similar results.)

Since compound 6 worked so well in the leukemia cell line, an examination of its effectiveness in vivo in a SupB15 model was undertaken. After 21 days of treatment with 10 mg/kg of compound 6 (i.p.) a dramatic reduction in the leukemic burden in the bone marrow as observed, as shown in FIG. 10c. Similar results were obtained when compound 6 was administered orally at 30 mg/kg SID.

Another difference between compound 6 and FTY720 or the enantiomer of compound 6, is that compound 6 has a specific and very high activity to BCR-Abl+ leukemias compared to other cell types. This trend is shown in FIG. 10d by calculating the ratio of 1050 for compound 6 (also called 177) and its enantiomer compound 5 (also called 39). If the drugs are similarly effective a ratio near 1 would be expected, and if compound 6 works better (has a lower 1050), a ratio greater than one as with SupB15s would be expected. As shown in the graph, it is found that compound 6 worked better than it enantiomer (ratio greater than 1) in 2 Ph+ ALL lines and in BM transduced with BCR-ABL p190 fusion, while 3 Ph− ALL lines all have a ratio close to 1. Next a non-sensitive line (CCRF) was transduced with p190 and it was found that it becomes sensitized to compound 6. Finally, it is seen that the Ph+ALL primary patient sample has a ratio greater than 1. This data supports a role for Abl or a downstream target in the gain of function of compound 6. In particular, cells that lack Abl kinase or that express only a form of Abl that is unable to translocate to the nucleus are resistant to treatment by compound 6, suggesting that the nuclear functions of Abl may play a role in the increased potency of compound 6 relative to its enantiomer, and that BCR-Abl expression is sufficient to confer enhanced sensitivity to compound 6 over its enantiomer.

Another conclusion that can be drawn from this study is that compound 6 retains enhanced activity over it enantiomer in cells that lack the pro-apoptotic proteins Bax and Bak suggesting that the enhanced activity of compound 6 relative to its enantiomer does not involve the activation of these proteins. Compound 6 and its enantiomer do not activate sphingosine-1-phosphate receptors when added to CHO cells expressing the receptors. When the pure phosphates are added to these CHO cells, multiple S1P receptors are activated when the phosphates are present at 1-10 uM. There is no enantiomer-selectivity in the activation of S1P receptors.

Figure 10E:
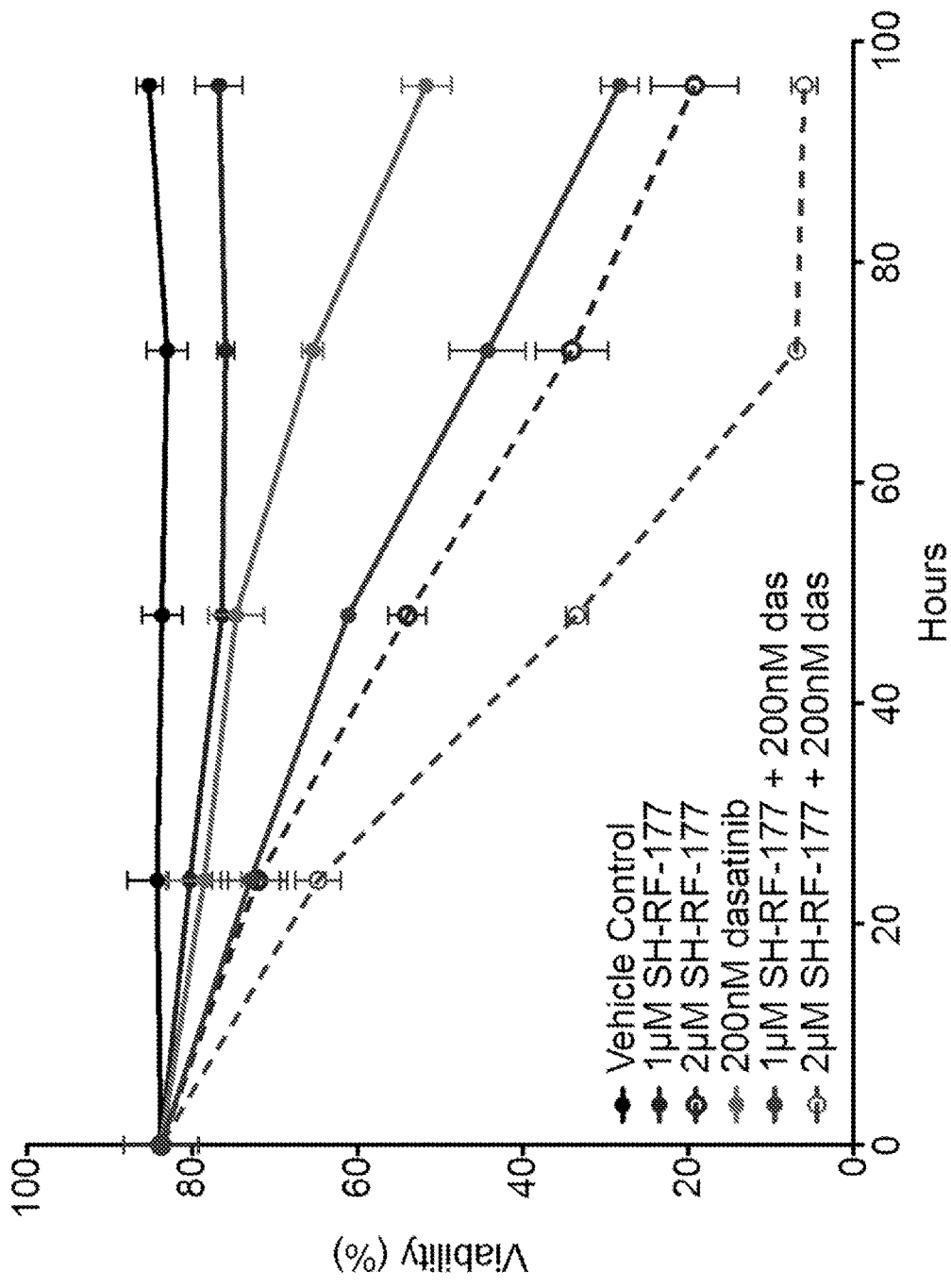
Figure 10F:
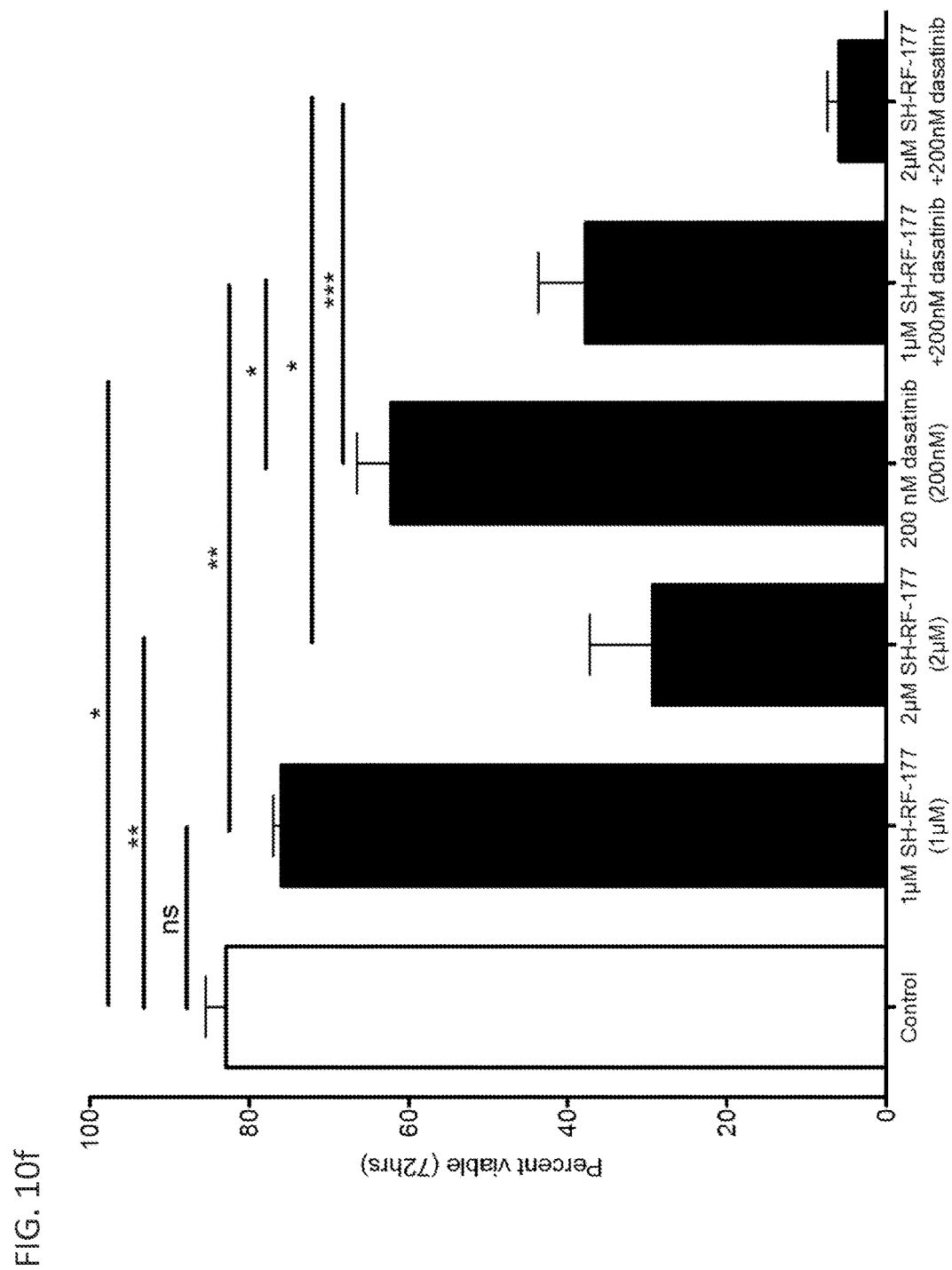
Figure 10G:
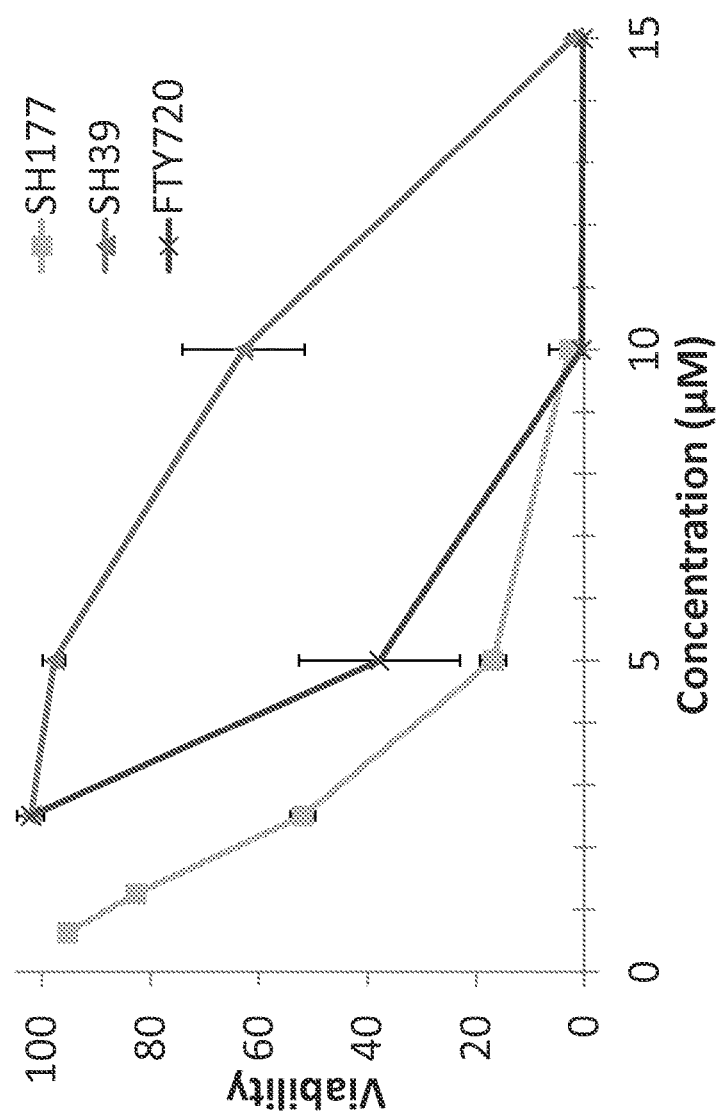

In FIGS. 10e to 10g the efficacy of compound 6 on the BCR-Abl+SupB15 leukemia cell line was studied. As will be described in greater detail below, the effects of the tyrosine kinase inhibitor dasatinib (standard-of-care) and compound 6 are additive. As shown in FIG. 10e when a sub-lethal concentration (1 µM=0.5×IC50) of compound 6 is combined with a maximally active dose of dasatinib (200 nM; based on the fact that 100 and 200 nM dasatinib kill the same way and that 100 nM dasatinib turns off Abl signaling at 1 h), compound 6 enhances cell death. At its IC50 (2 µM), compound 6 kills effectively on its own and killing is enhanced in the presence of dasatinib. FIG. 10f provides a bar graph of data from the 72 h time point on FIG. 10d. While 1 µM compound 6 (=0.5×IC50) does not kill, 2 µM (1×IC50) significantly reduces cell viability at 72 h. When combined with a maximally effective dose of dasatinib (200 nM), 1 µM compound 6 increases cell death. Adding dasatinib to 2 µM compound 6 increases cell death beyond that caused by compound 6 alone.

Finally, in FIG. 10g dose response curves are provided for studies conducted with patient-derived BCR-Abl+ acute lymphoblastic leukemia cells. Viability was measured at 96 h by flow cytometry (vital dye exclusion). Compound 6 is more potent than FTY720 and its enantiomer, compound 39. In conclusion, dasatinib (a successful therapeutic for BCR-Abl positive leukemias that does not, however, cure disease) works better in combination with compound 6, according to embodiments of the invention. In addition, compound 6 kills better than dasatinib when both drugs are used at their maximally active dose.

Figure 10K:
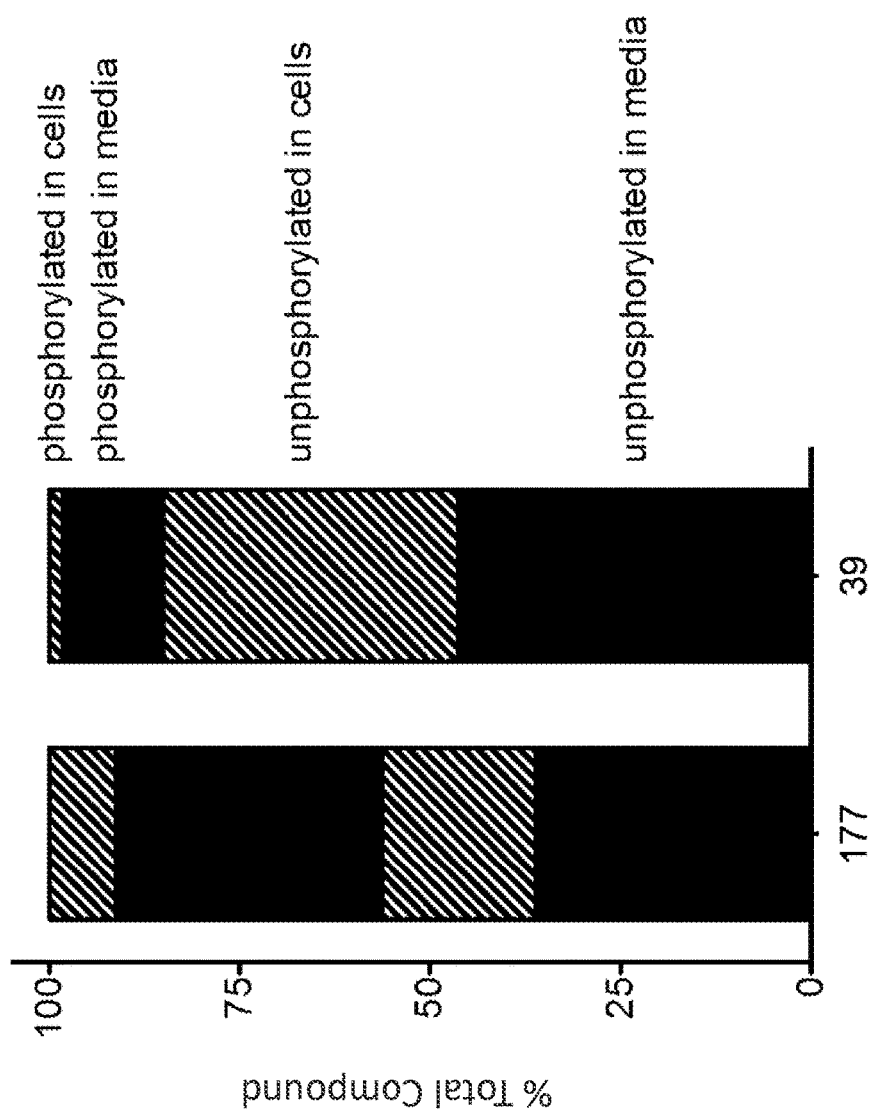
Figure 10I:
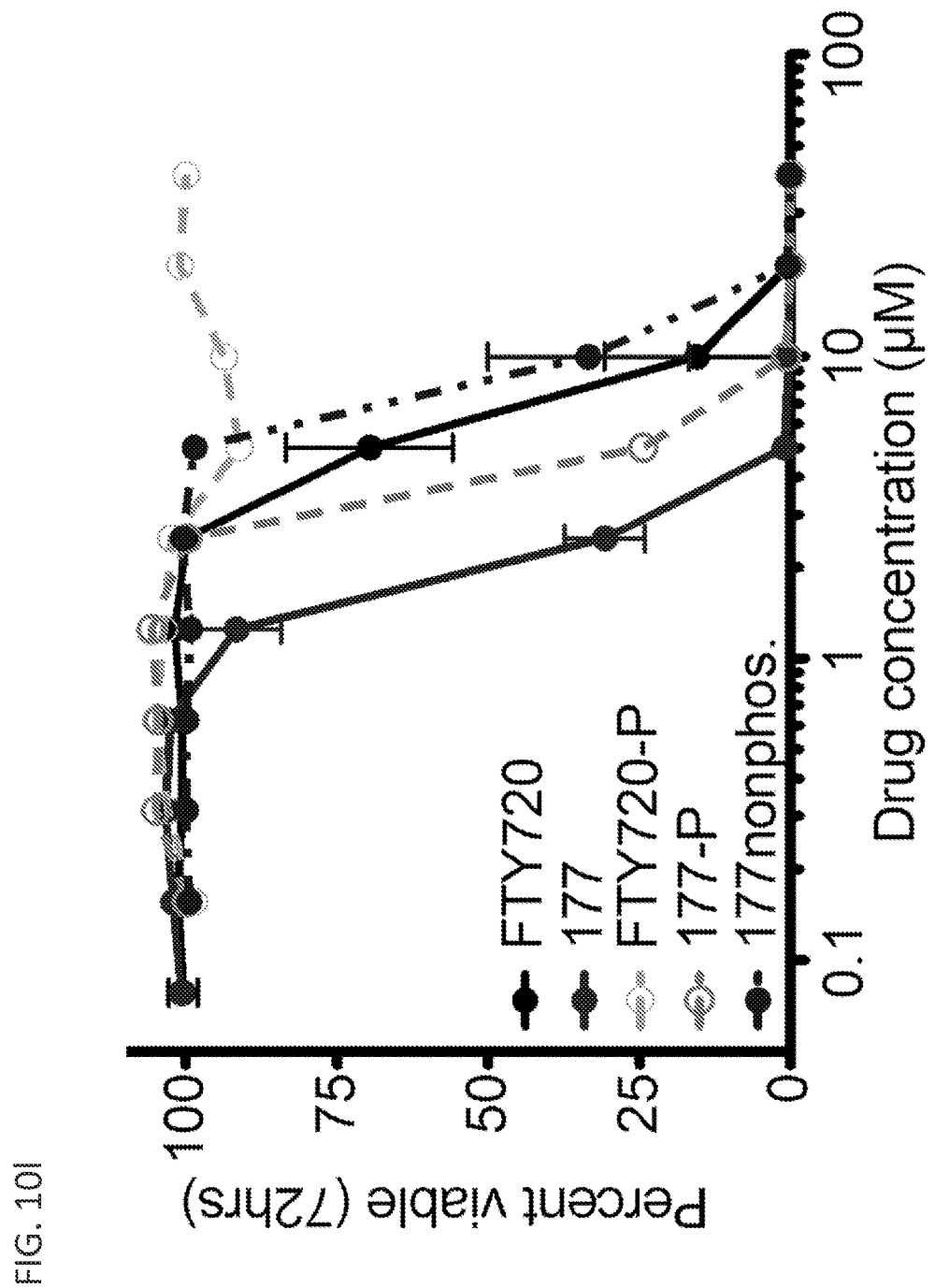

The importance of phosphorylation in the activity of compound 6 was then examined. In this study MEF knock-out lines that show the same differential sensitivity to compound 6 relative to its enantiomers as leukemia cells were used (FIG. 10h). As shown in FIG. 10i, this difference is maintained in SphK1 null MEFs. However, compound 6 no longer shows gain of functional activity in SphK2 null MEFs (FIG. 10j), suggesting that compound 6 is a substrate for SphK2 and its phosphorylation is important for its function, and contributes to its anti-cancer activity. Moreover, as shown in FIG. 10k, although both compound 6 and its enantiomer (labeled 39 in FIG. 10k) are phosphorylated by sphingosine kinase 2 in cells, the phosphorylation of compound 6 is more efficient. A phosphate and a non-phosphorylatable analog of compound 6 were then tested. As shown in FIG. 10l, both kill leukemia cells, but the non-phosphorylatable analog (labeled 177-nonphos) is less effectively than compound 6 suggesting that both the phosphorylated and unphosphorylated forms contribute to the anti-cancer effects.

Figure 10M:
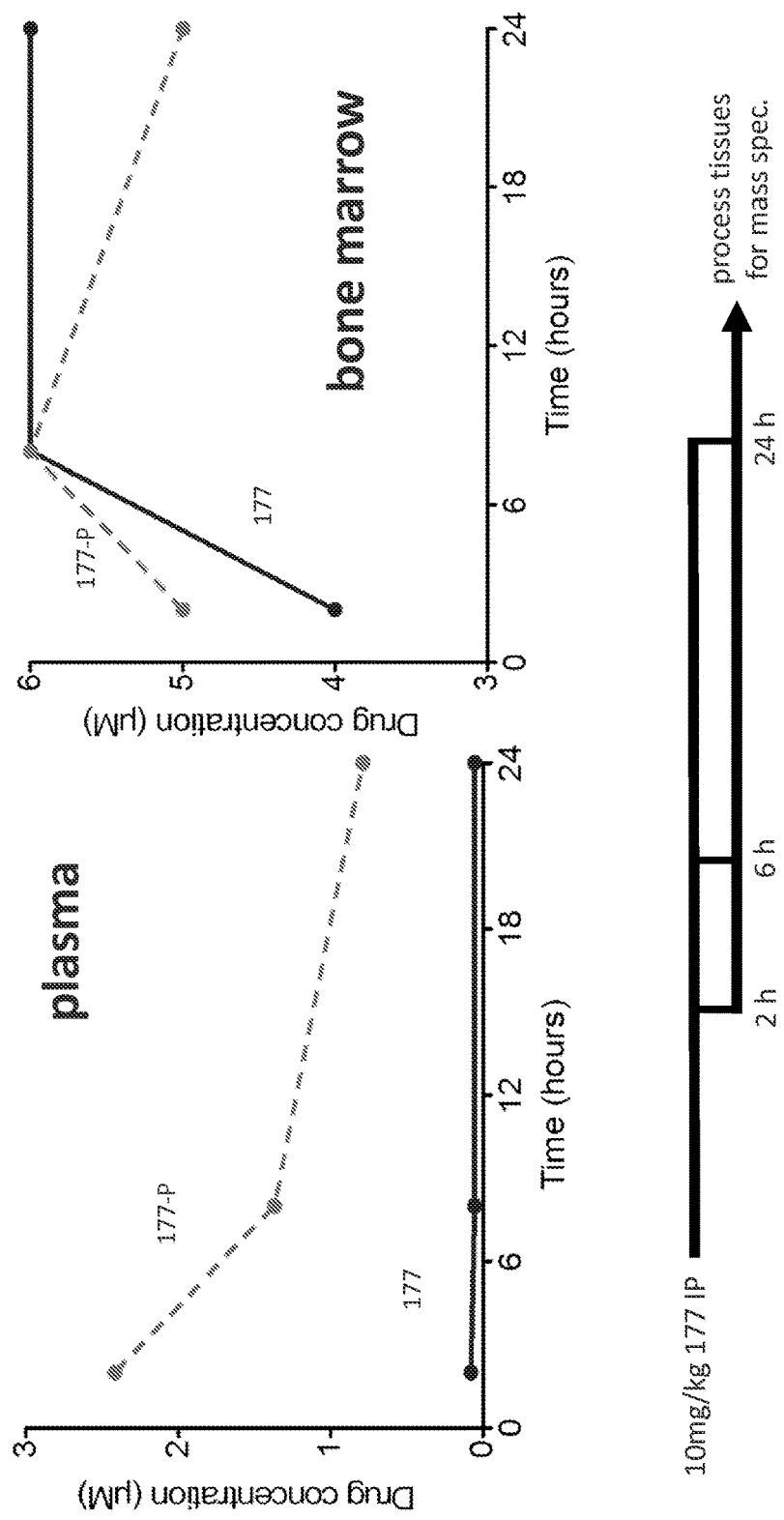

A study was then conducted to examine what happens to compound 6 when administered to animals. Mice were treated with 10 mg/kg doses of compound 6 (i.p.) and then the mice were sacrificed at various time points, then plasma, bone marrow, and spleen tissue were extracted to build curves. As shown in FIG. 10m, the phosphorylated form predominates in plasma (the ratio of phosphorylated to unphosphorylated compound 6 in the plasma is >10:1), but that compound 6 and its phosphorylated form are present at roughly equimolar amounts in bone marrow, which is where disease forms in the leukemia model and seems to be present above 1050 for SupB15s. Indeed, the ratio of phosphorylated to unphosphorylated compound 6 in the spleen and bone marrow is close to 1:1 after i.p. administration. Normalization to total protein suggests that compound 6 accumulates in tissues to higher levels than are present in blood.

Figure 10N:
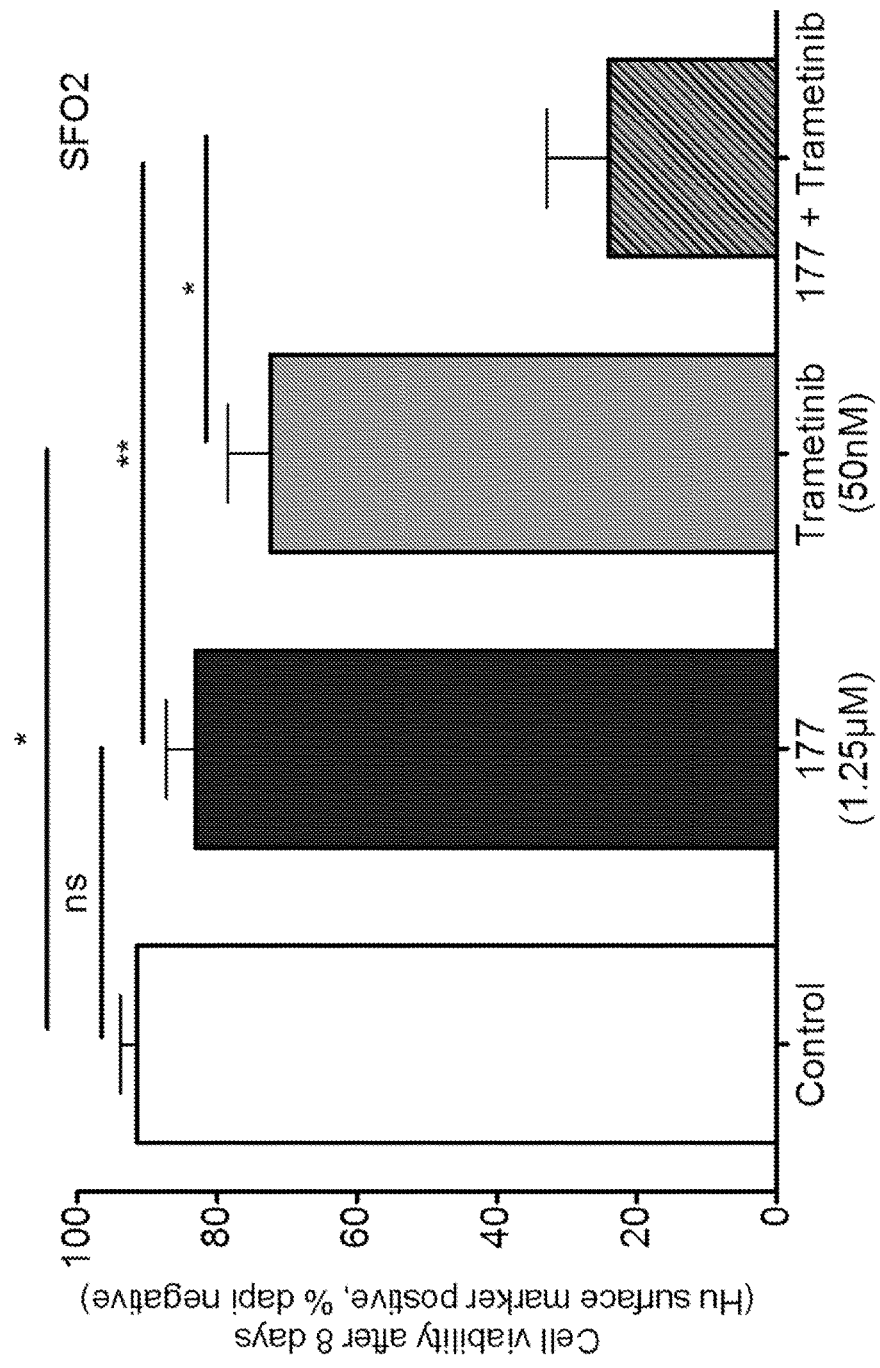
Figure 10O:
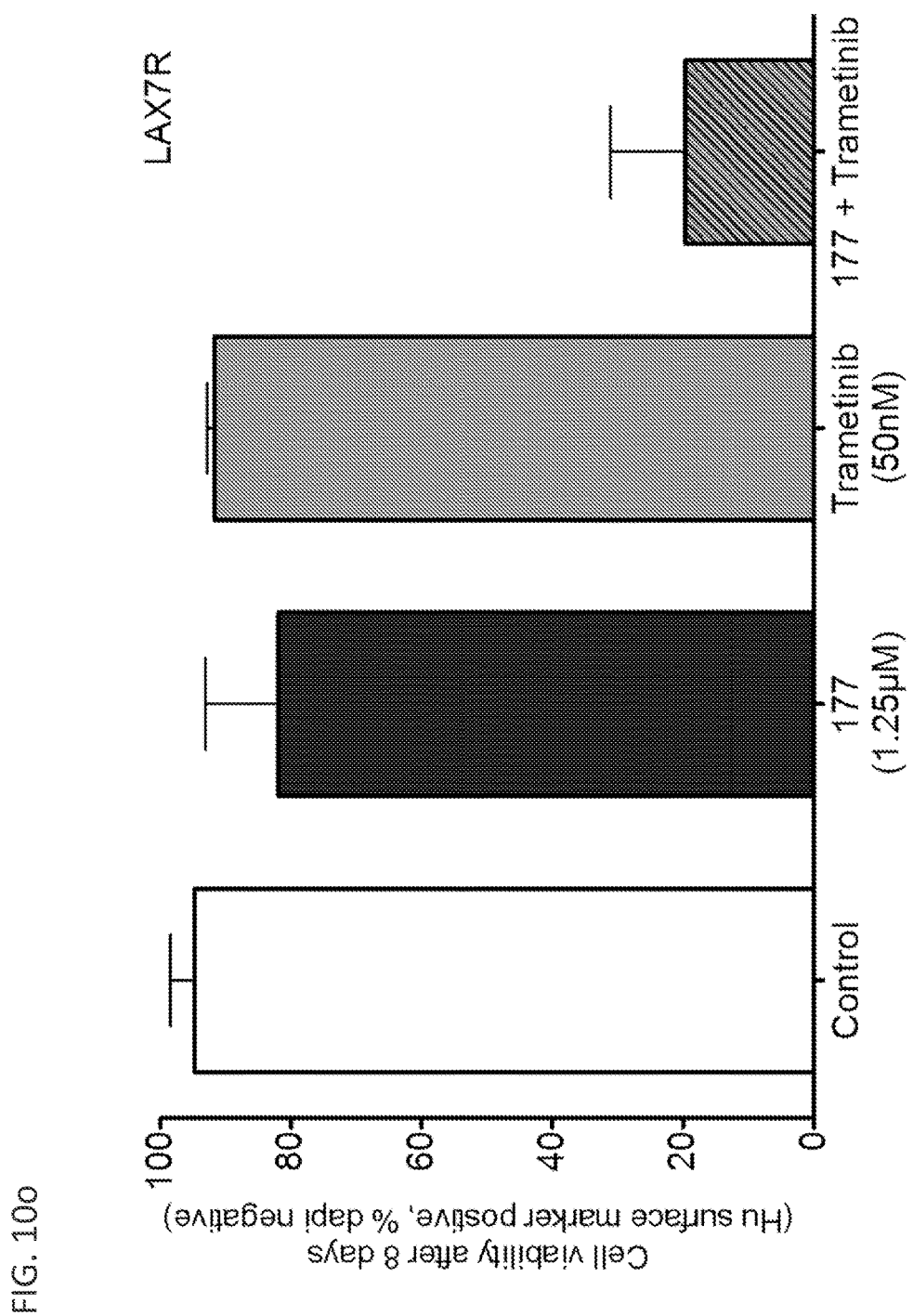

FIGS. 10n and 10o provide data results from a study of the effectiveness of treating BCR-Abl+ SFO2 cells (10n), and also in BCR-Abl− LAX7R cells (10o), which is a late-stage leukemia resistant to chemotherapy. As shown in FIG. 10n, combining a cytostatic concentration of the MEK1 inhibitor trametinib with a cytostatic concentration of compound 6 kills patient-derived leukemia cells without killing the irradiated stromal cell layer. Some BCR-Abl negative patient leukemia samples (FIG. 10o) are sensitive to this drug combination although they are not sensitive to compound 6 as a single agent. Similar to the BCR-Abl negative leukemia results shown in FIG. 10o, the combination of trametinib and compound 6 can kill human colon cancer cells that do not die when treated with compound 6 or trametinib as single agents. These studies suggest that elevated ERK activity confers resistance to compound 6 and that inhibiting MEK, and thus ERK, signaling with trametinib sensitizes BCR-Abl-positive and -negative cancer cells to compound 6.

SUMMARY

FTY720 functions as an immunosuppressant due to its effect on sphingosine-1-phosphate receptors. At doses well above those needed for immunosuppression, FTY720 also has anti-neoplastic actions. It has now been determined that FTY720's anti-cancer activity depends in part on its ability to induce nutrient transporter down-regulation. Embodiments of compounds that trigger nutrient transporter loss but lack FTY720's S1P receptor-related, dose-limiting toxicity are presented that can be used as effective and selective anti-tumor agents. In particular, a series of enantiomerically pure and stereochemically diverse O-substituted benzyl ethers of pyrrolidines were generated and shown to have the ability to kill human leukemia cells. The stereochemistry of the hydroxymethyl was found to be an effective means of tuning the compound activity. Moreover, phosphorylation of this group was shown not to be required for anti-leukemic activity.

DOCTRINE OF EQUIVALENTS

While the above description contains many specific embodiments of the invention, these should not be construed as limitations on the scope of the invention, but rather as an example of one embodiment thereof. Accordingly, the scope of the invention should be determined not by the embodiments illustrated, but by the appended claims and their equivalents.

What is claimed is:
1. A compound of formula

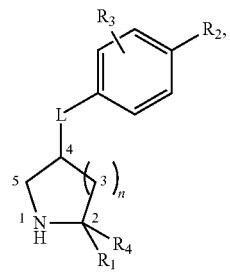

or a pharmaceutically acceptable salt thereof
wherein:

$R_1$ is a group selected from hydrogen, an alkyl chain, $(CH_2)_nOH$, $(CH_2)_nOPO_3^{2-}$ CHOH-alkyl, CHOH-alkyne, and $(CH_2)_nOMe$;

$R_2$ is an aliphatic chain having six to ten carbons;

$R_3$ is one to four substituents selected from hydrogen, halogen, alkyl, alkoxy, azide ($N_3$), ether, $NO_2$, or cyanide (CN);

$R_4$ is a group selected from hydrogen, $CH_2OPO_3^{2-}$ and $CH_2OH$;

L is O—$CH_2$;

Me is an alkyl, alkene or alkyne;

n is an independently selected integer selected from the group of 1, 2, or 3; and wherein the benzyl group through oxygen atom of the linker L is linked to the pyrrolidine ring at either position 3 or 4.

2. The compound of claim 1, wherein the benzyl group through oxygen atom of the linker L is linked to the pyrrolidine ring at position 3.

3. The compound of claim 1, wherein the stereochemistry of the compound is selected from the group consisting of S at position 2 and R at position 4, R at position 2 and S at position 4, R at position 2 and R at position 4, and S at position 2 and S at position 4.

4. The compound of claim 1, wherein R4 is a group selected from $CH_2OH$ or $CH_2OPO_3^{2-}$, and wherein the benzyloxy group attached to the pyrrolidine group is in one of either a cis or trans orientation relative to R4.

5. The compound of claim 1, wherein $R_2$ is $C_8H_{17}$ and $R_1$ is $CH_2OH$.

6. A pharmaceutical comprising a therapeutically effective amount of a compound of formula

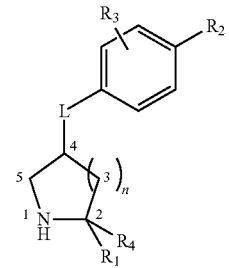

or a pharmaceutically acceptable salt thereof,
wherein:

$R_1$ is a group selected from hydrogen, an alkyl chain, $(CH_2)_nOH$, $(CH_2)_nOPO_3^{2-}$ CHOH-alkyl, CHOH-alkyne, and $(CH_2)_nOMe$;

$R_2$ is an aliphatic chain having six to ten carbons;

$R_3$ is one to four substituents selected from hydrogen, halogen, alkyl, alkoxy, azide ($N_3$), ether, $NO_2$, or cyanide (CN);

$R_4$ is a group selected from hydrogen, $CH_2OPO_3^{2-}$ and $CH_2OH$;

L is O—$CH_2$;

Me is an alkyl, alkene or alkyne;

n is an independently selected integer selected from the group of 1, 2, or 3; and wherein the benzyl group through oxygen atom of the linker L is linked to the pyrrolidine ring at either position 3 or 4.

7. The pharmaceutical of claim 6, wherein the benzyl group through oxygen atom of the linker L is linked to the pyrrolidine ring at position 3.

8. The pharmaceutical of claim 6, wherein the stereochemistry of the compound is selected from the group consisting of S at position 2 and R at position 4, R at position 2 and S at position 4, R at position 2 and R at position 4, and S at position 2 and S at position 4.

9. The pharmaceutical of claim 6, wherein R4 is a group selected from $CH_2OH$ or $CH_2OPO_3^{2-}$, and wherein the benzyloxy group attached to the pyrrolidine group is in one of either a cis or trans orientation relative to R4.

10. The pharmaceutical of claim 6, wherein $R_2$ is $C_8H_{17}$ and $R_1$ is $CH_2OH$.

* * * * *